United States Patent [19]
Schaack

[11] Patent Number: 6,009,189
[45] Date of Patent: Dec. 28, 1999

[54] APPARATUS AND METHOD FOR MAKING ACCURATE THREE-DIMENSIONAL SIZE MEASUREMENTS OF INACCESSIBLE OBJECTS

[76] Inventor: David F. Schaack, 1243 Monte Verde Dr. NE., Albuquerque, N.Mex. 87112

[21] Appl. No.: 08/689,993

[22] Filed: Aug. 16, 1996

[51] Int. Cl.⁶ .................................................. G06K 9/00
[52] U.S. Cl. .................... 382/154; 382/106; 382/201; 382/255; 348/40; 348/42; 348/43; 348/50; 348/51; 348/85; 348/137; 348/142; 702/127; 702/150; 702/152; 702/153
[58] Field of Search .................. 382/201, 106, 382/154, 255; 348/40, 42, 43, 50, 51, 85, 137, 142, 95; 702/127, 150, 152, 153, 158; 356/3

[56] References Cited

U.S. PATENT DOCUMENTS

| | | | |
|---|---|---|---|
| 4,078,864 | 3/1978 | Howell | 356/171 |
| 4,207,594 | 6/1980 | Morris et al. | 358/107 |
| 4,651,311 | 3/1987 | Owen et al. | 367/147 |
| 4,702,229 | 10/1987 | Zobel | 128/4 |
| 4,721,098 | 1/1988 | Watanabe | 128/4 |
| 4,820,043 | 4/1989 | Diener | 356/241 |
| 4,825,259 | 4/1989 | Berry, Jr. | 356/241 |
| 4,837,615 | 6/1989 | Boshier | 358/100 |
| 4,895,431 | 1/1990 | Tsujiuchi et al. | 350/320 |
| 4,935,810 | 6/1990 | Nonami et al. | 358/98 |
| 4,969,736 | 11/1990 | Slotwinski et al. | 356/4.5 |
| 5,070,401 | 12/1991 | Salvati et al. | 358/107 |
| 5,243,665 | 9/1993 | Maney et al. | 382/8 |
| 5,417,210 | 5/1995 | Funda et al. | 128/653.1 |
| 5,424,836 | 6/1995 | Weise et al. | 356/376 |
| 5,432,543 | 7/1995 | Hasegawa et al. | 348/45 |
| 5,432,895 | 7/1995 | Myers | 395/119 |
| 5,573,492 | 11/1996 | Dianna et al. | 600/117 |
| 5,575,754 | 11/1996 | Konomura . | |
| 5,594,543 | 1/1997 | de Groot et al. | 356/5.09 |

OTHER PUBLICATIONS

Sabry F. El–Hakim et al; Multicamera . . . engineering; Sep. 193; pp. 2201–2215.
N. Oda et al; "Estimation . . . sequence"; 1993; 85–92.
Yi–Ping Hung; "Three . . . Approach"; May 1990.

*Primary Examiner*—Jose L. Couso
*Assistant Examiner*—Kanji Patel
*Attorney, Agent, or Firm*—Robert W. Becker & Associates

[57] ABSTRACT

Spatial locations of individual points on an inaccessible object are determined by measuring two images acquired with one or more cameras which can be moved to a plurality of positions and orientations which are accurately determined relative to the instrument. Once points are located, distances are easily calculated. In distinction to prior art, which uses a fixed separation of camera viewpoints, this new system offers smaller errors, measurement over a larger range of object distances, and measurement of distances which cannot be contained in a single camera view. Random errors are minimized by use of an optimum measurement geometry. Systematic errors are minimized by use of a complete and robust set of calibration procedures. A standard measurement procedure automatically obtains the optimum measurement geometry. A least squares calculation uses all of the image location and calibration data to derive the true three dimensional positions of the selected object points. This calculation is taught explicitly for any camera geometry and motion. In preferred embodiments, the image locations of selected object points are determined by alignment of video cursors with the video images of those points. In certain of the preferred embodiments, the camera is a standard, side-looking rigid borescope, enabling this improved measurement system to be retrofit to existing remote inspection systems at minimum cost. In other preferred embodiments, the measurement system is implemented in either a rigid borescope or in a flexible endoscope.

35 Claims, 35 Drawing Sheets

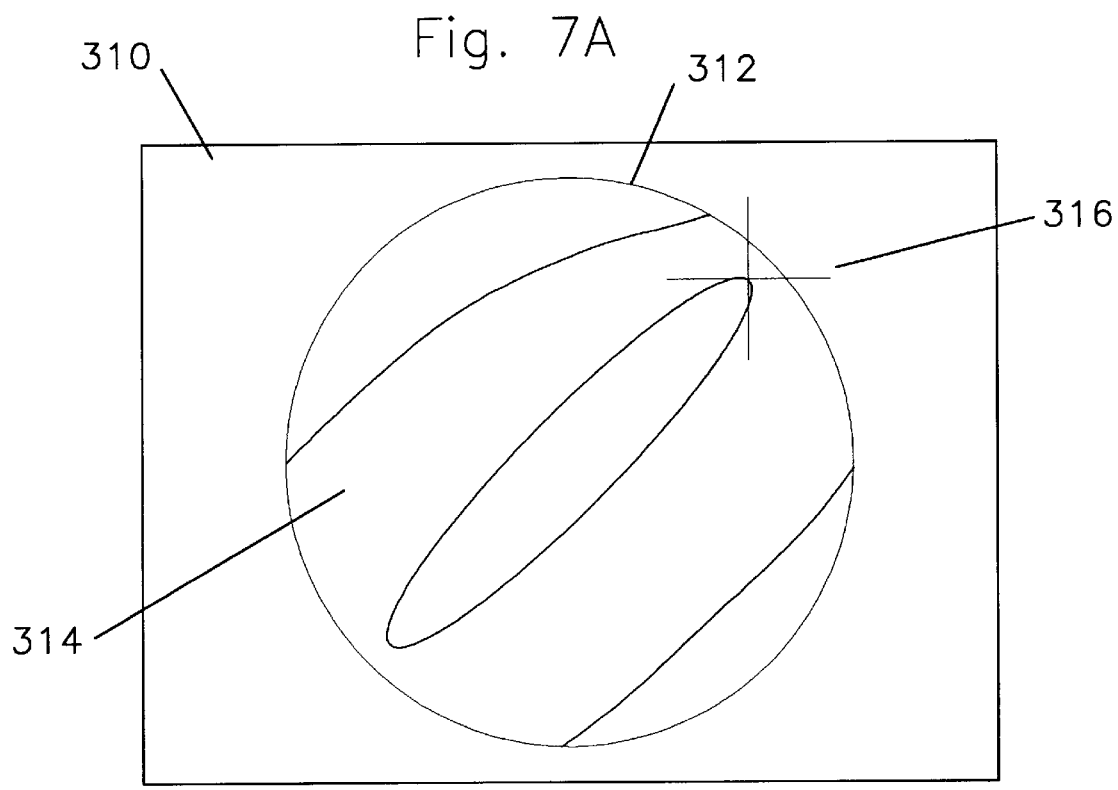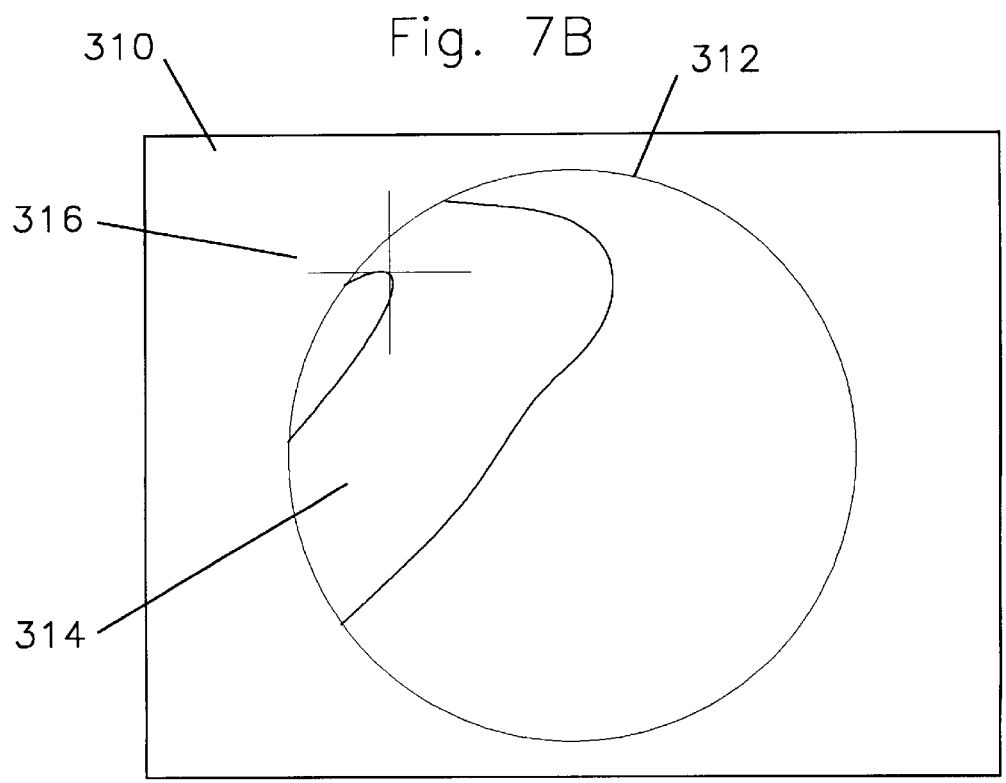

Note: Distances d and r do not necessarily lie in the plane of this figure.

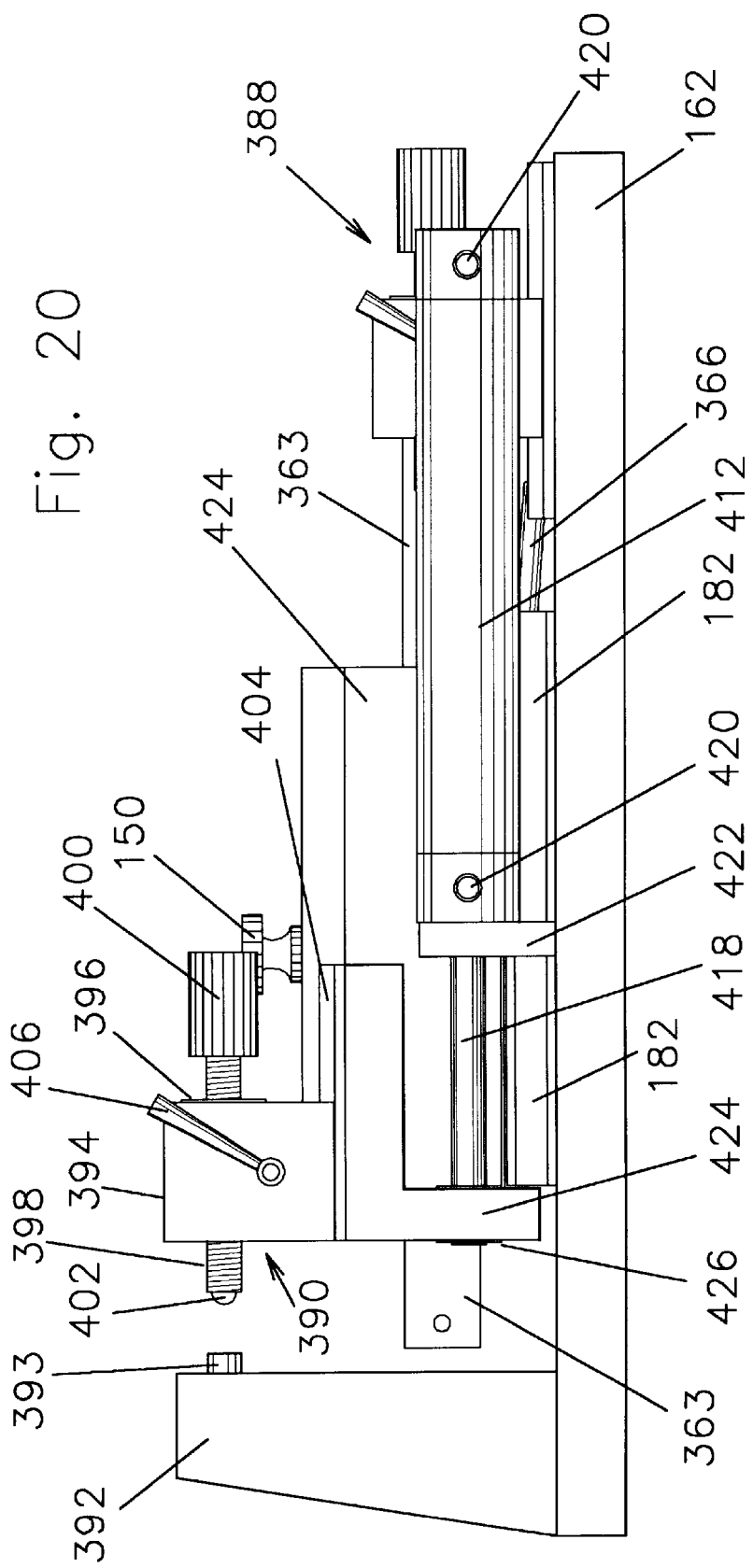

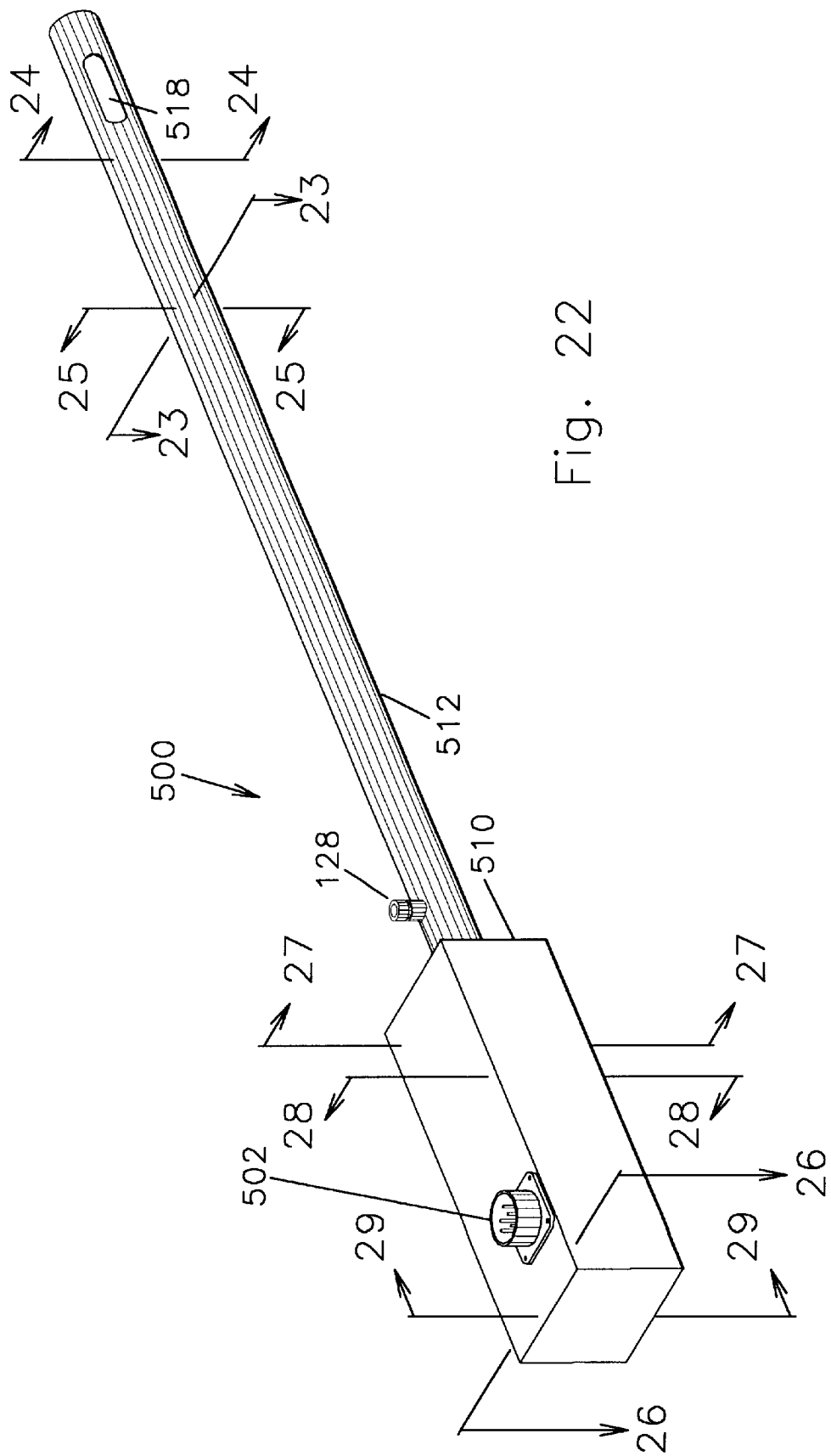

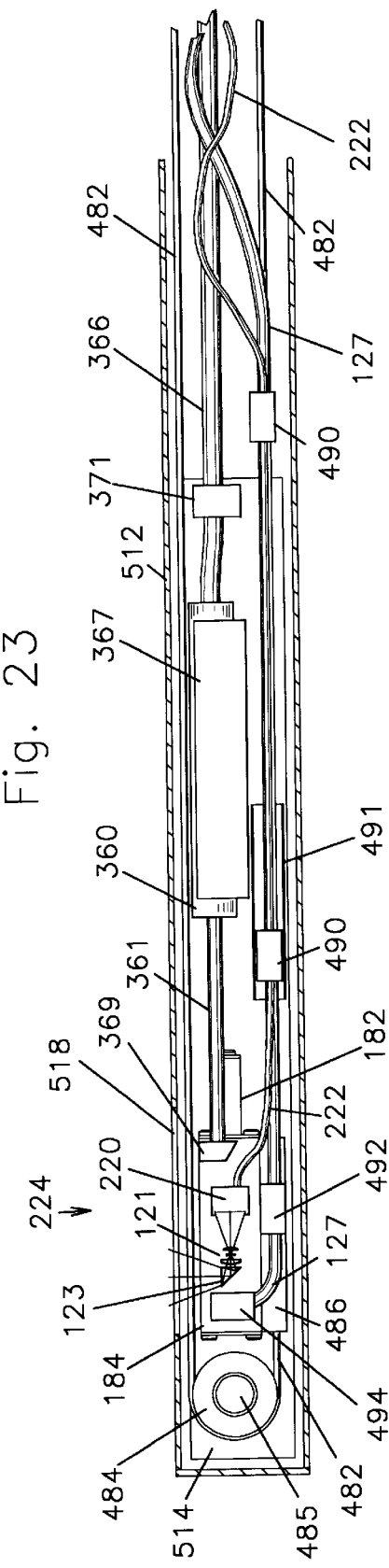
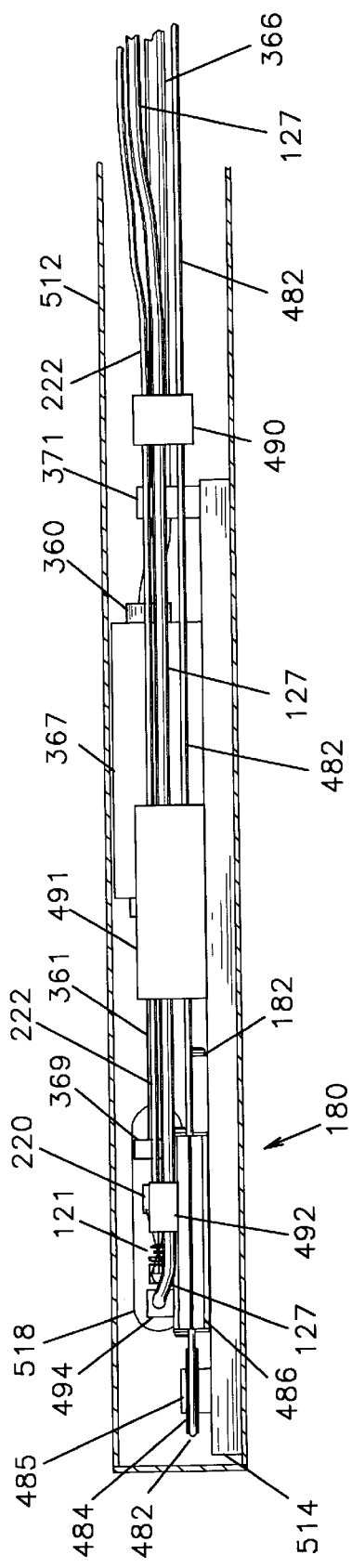

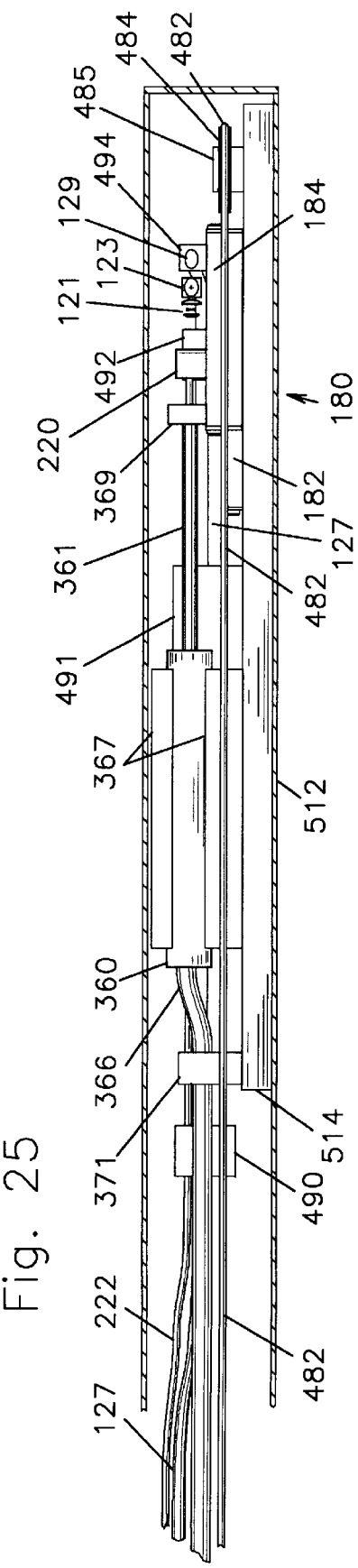
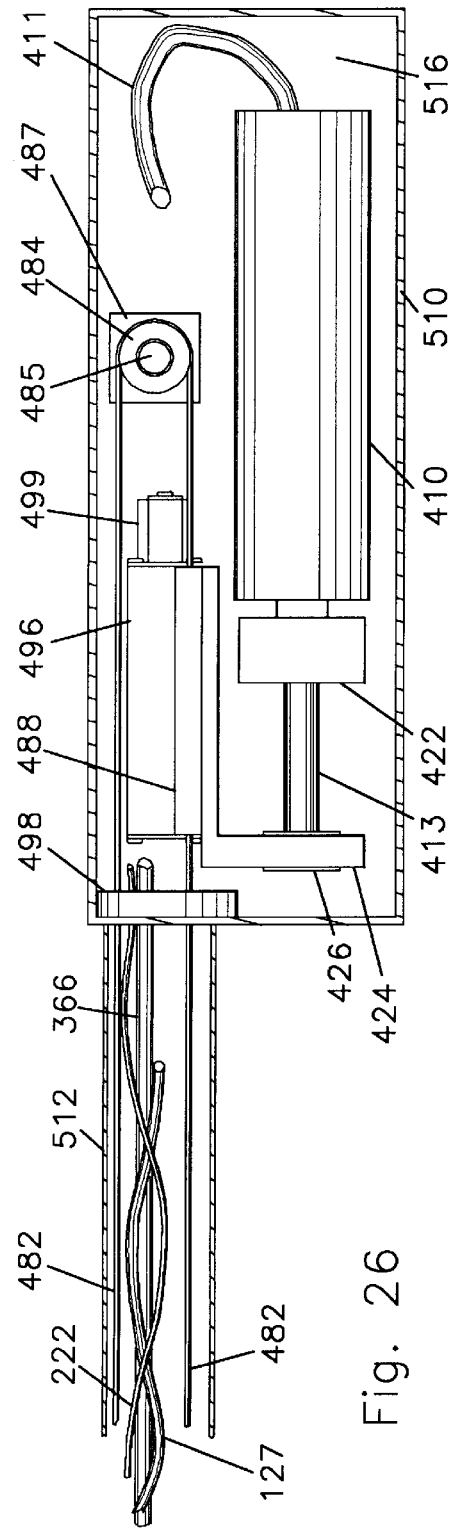
Fig. 25
Fig. 26

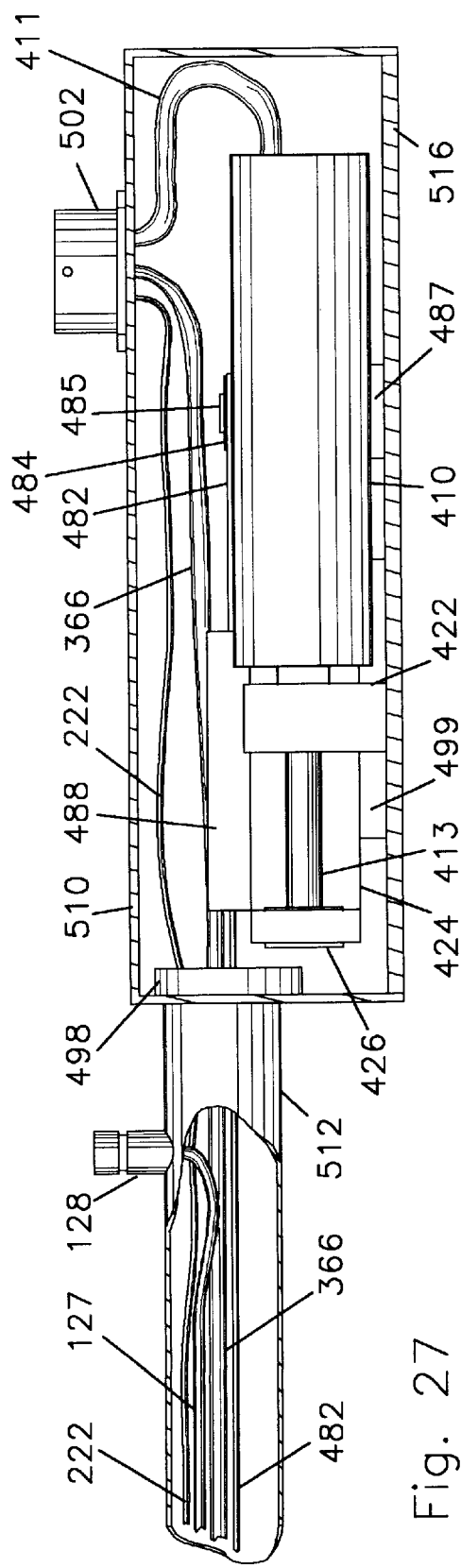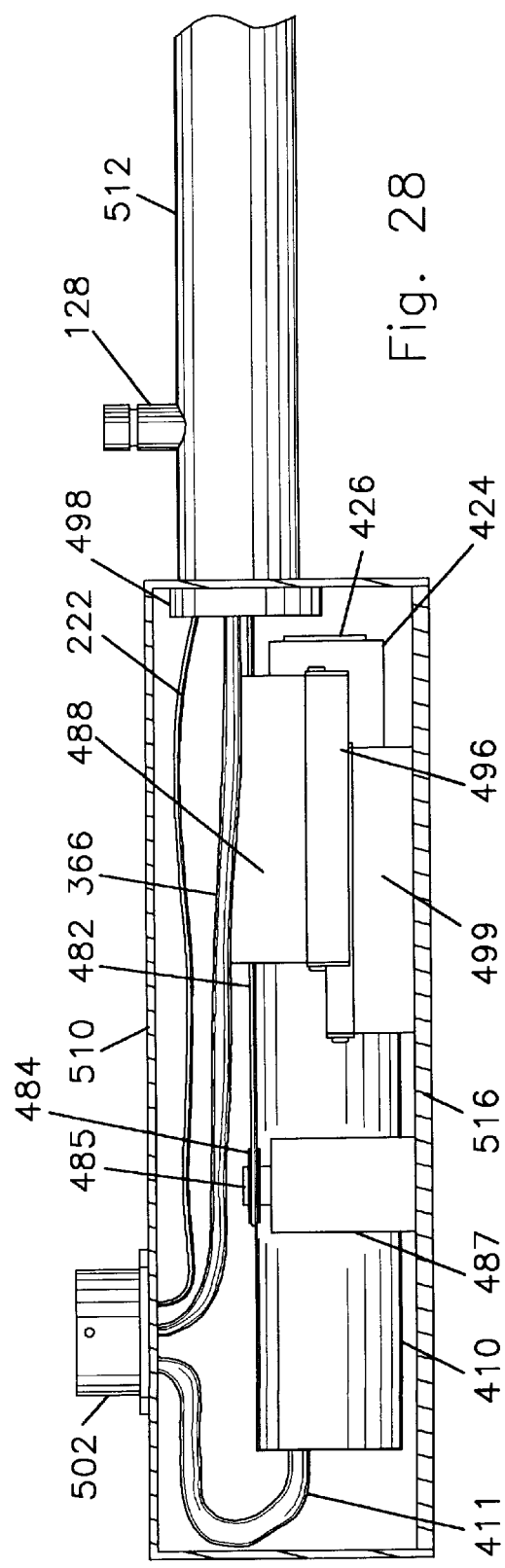

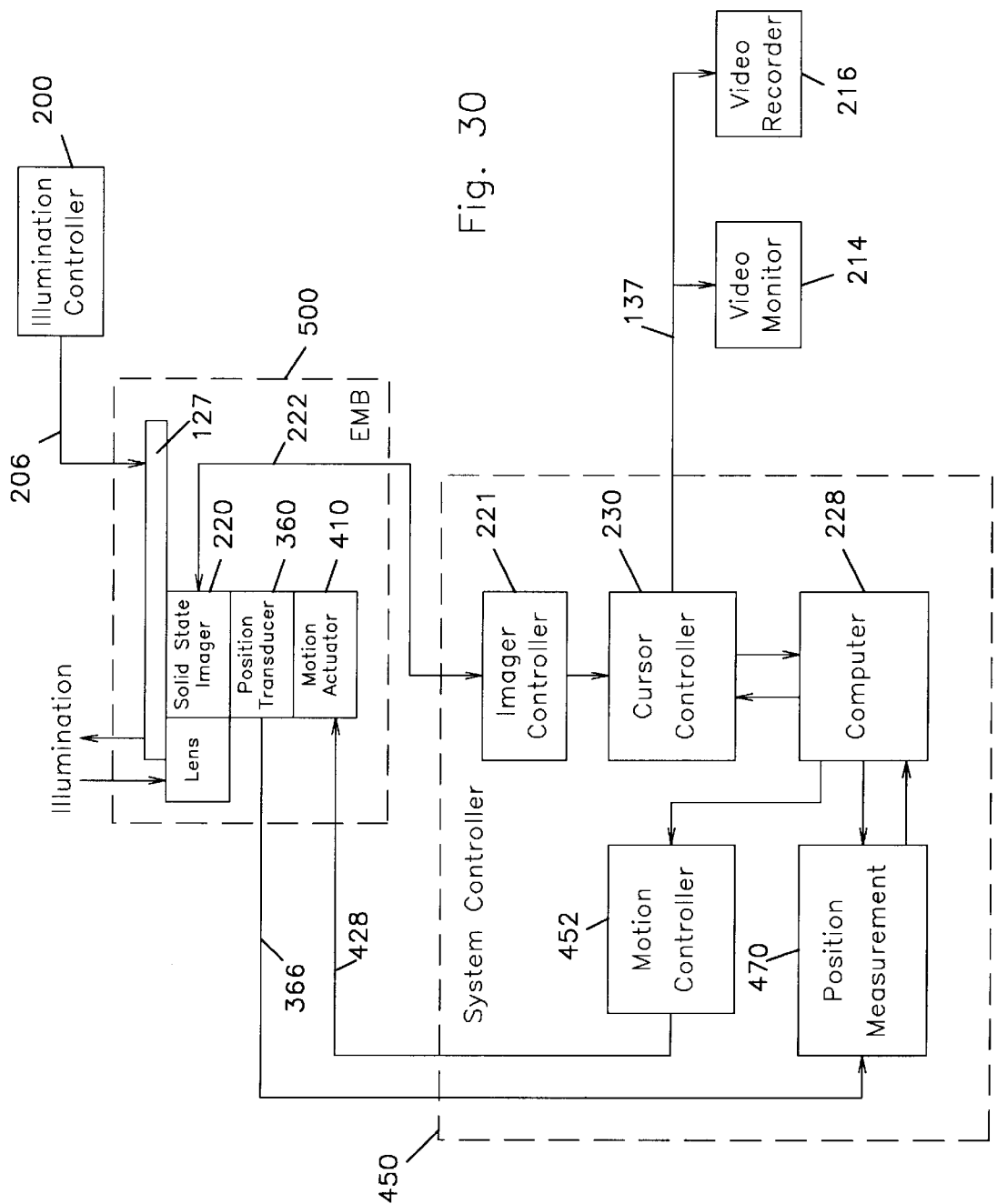

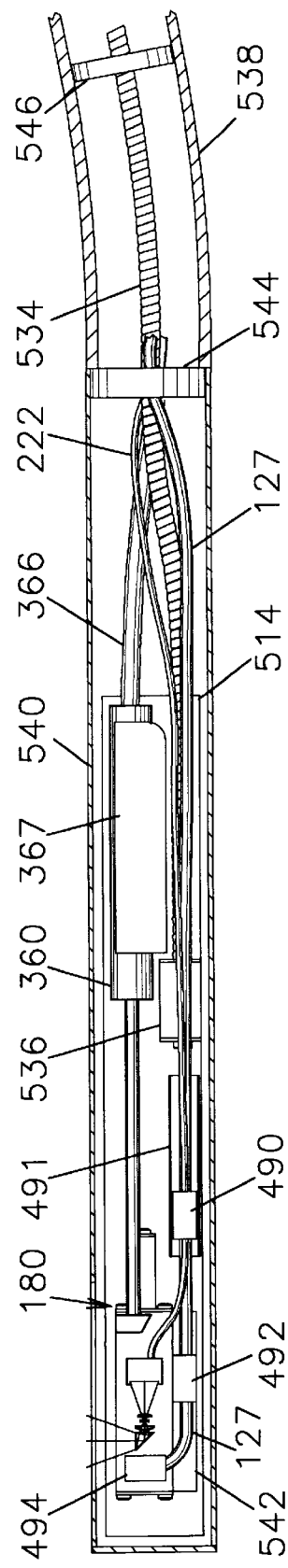
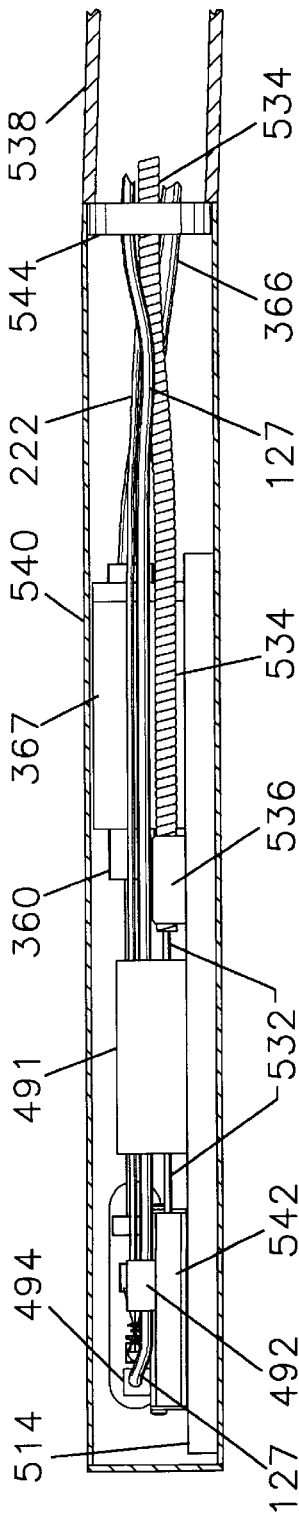

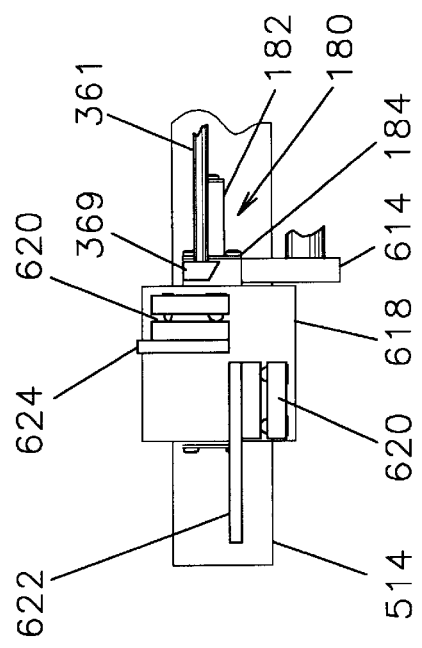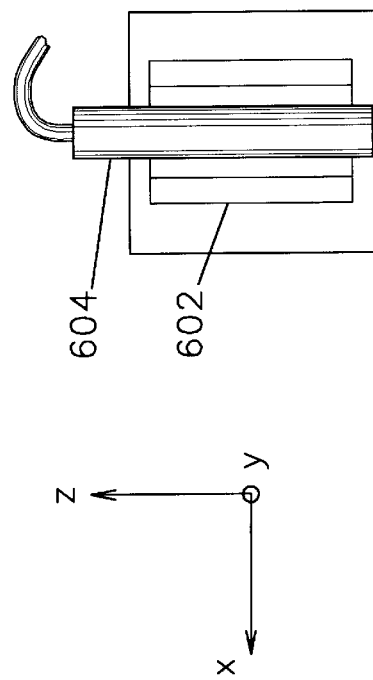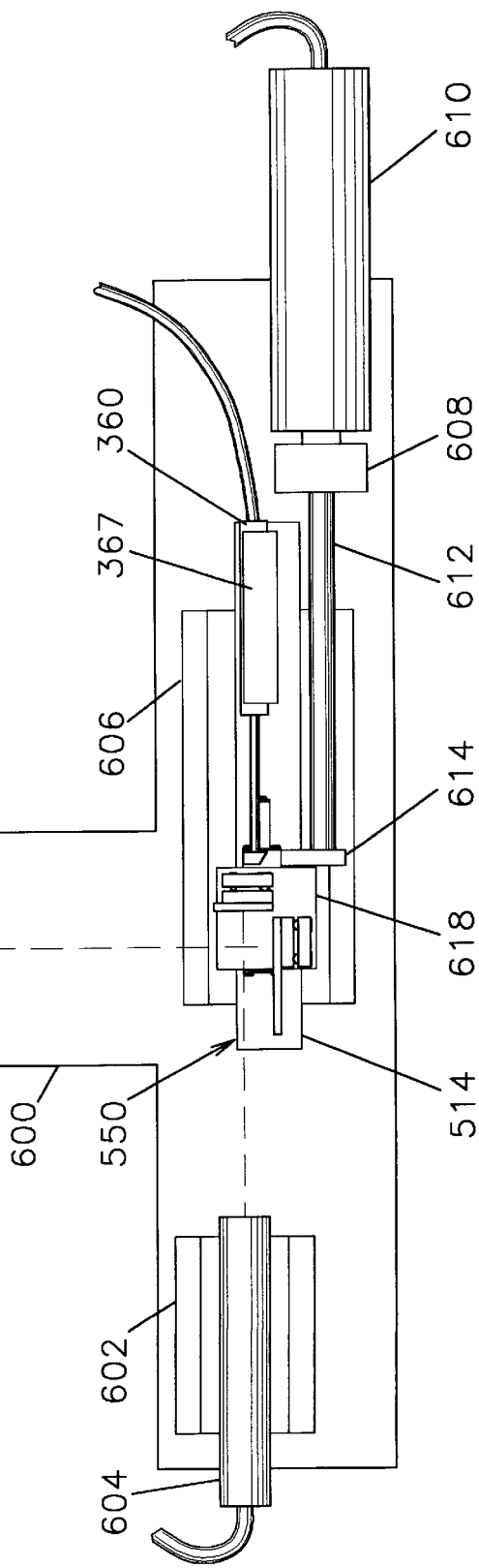

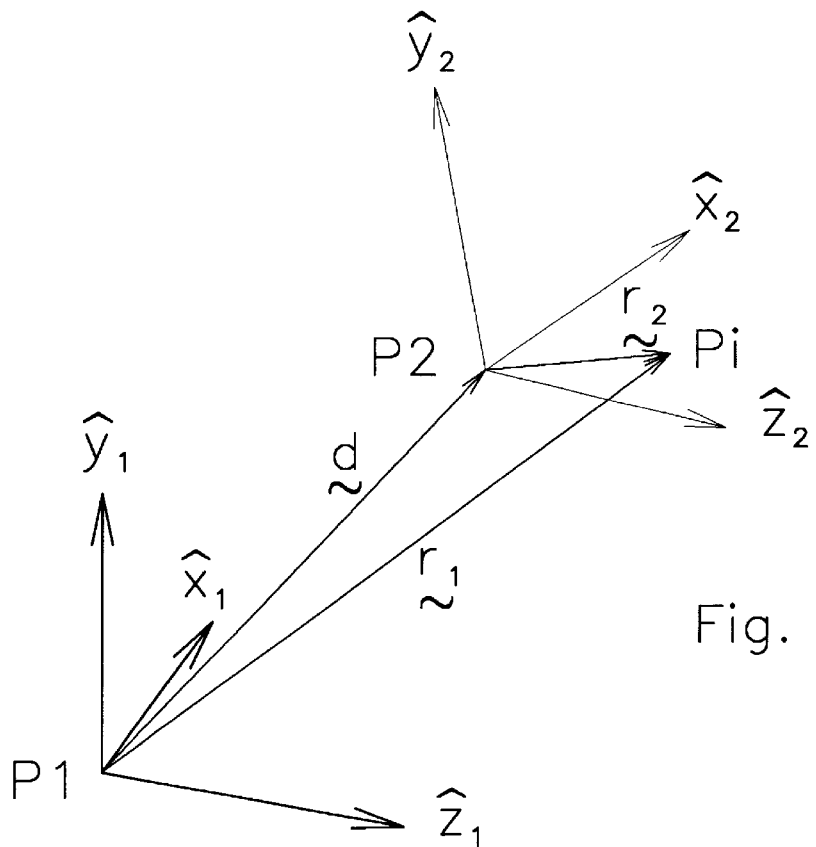
Fig. 43
Fig. 44
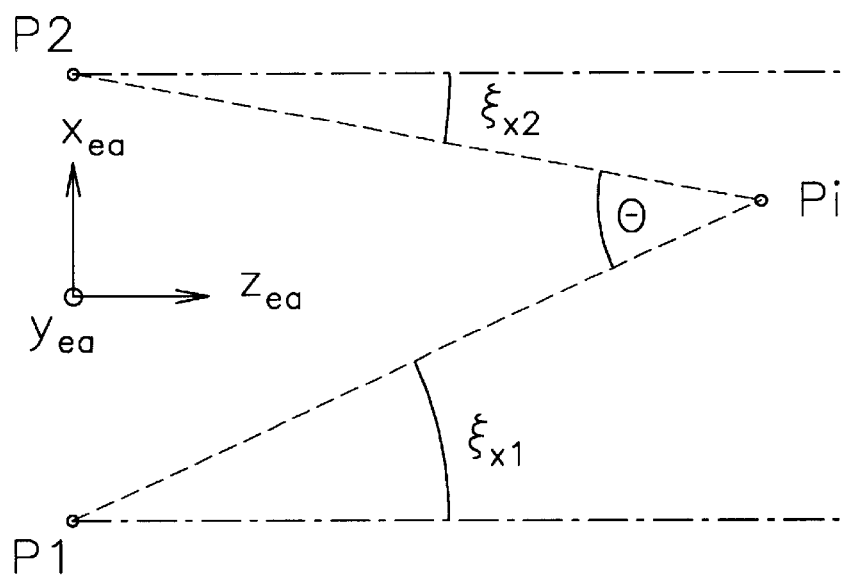

APPARATUS AND METHOD FOR MAKING ACCURATE THREE-DIMENSIONAL SIZE MEASUREMENTS OF INACCESSIBLE OBJECTS

BACKGROUND—FIELD OF THE INVENTION

This invention relates to optical metrology, specifically to the problem of making non-contact dimensional measurements of inaccessible objects which are viewed through an endoscope.

BACKGROUND—PRIOR ART

A. Introduction

In the past several decades, the use of optical endoscopes has become common for the visual inspection of inaccessible objects, such as the internal organs of the human body or the internal parts of machinery. These visual inspections are performed in order to assess the need for surgery or equipment tear down and repair; thus the results of the inspections are accorded a great deal of importance. Accordingly, there has been much effort to improve the art in the field of endoscopes.

Endoscopes are long and narrow optical systems, typically circular in cross-section, which can be inserted through a small opening in an enclosure to give a view of the interior. They almost always include a source of illumination which is conducted along the interior of the scope from the outside (proximal) end to the inside (distal) end, so that the interior of the chamber can be viewed even if it contains no illumination. Endoscopes come in two basic types; these are the flexible fiberscopes and the rigid borescopes. Fiberscopes are more versatile, but borescopes can provide higher image quality, are less expensive, are easier to manipulate, and are thus generally preferred in those applications for which they are suitable.

While endoscopes (both fiberscopes and borescopes) can give the user a relatively clear view of an inaccessible region, there is no inherent ability for the user to make a quantitative measurement of the size of the objects he or she is viewing. There are many applications for which the size of an object, such as a tumor in a human body, or a crack in a machine part, is a critically important piece of information. Thus, there have been a number of inventions directed toward obtaining quantitative size information along with the view of the object through the endoscope.

A particular illustrative application is presented by the needs of aircraft engine operators. In-service inspection of aircraft turbine engines is an important part of aviation safety. Typically, these inspections are required every 200 to 300 hours of engine operation. As part of the inspection procedure, endoscopes are used to determine visually the integrity of engine internal components such as compressor and turbine blades, engine linings, and combustor cans. The types of problems that inspectors look for are missing components, fatigue fractures, and foreign object impact damage.

Side-looking borescopes are used for most of these inspections, as opposed to flexible fiberscopes, because they are well suited to the geometry of these engines, as well as because of the other advantages listed previously.

If a defect, such as a crack, a pit, or a nick, is detected, it is necessary to determine its size, because the engine can be left in service only if the defect is smaller than a critical size defined by the engine manufacturer or the air carrier.

The problem is that the accuracy to which the size of defects can be determined is poor with the currently used techniques. Part of the reason is that the magnification at which the defect is being viewed through the borescope is unknown. The other part of the problem is that the defects occur on surfaces which are curved in three dimensions, and the view through the borescope is strictly two-dimensional.

Many concepts have been proposed and patented for addressing the need to make quantitative measurements through endoscopes (both borescopes and fiberscopes). Only some of these concepts address the need to make the measurement in three dimensions. Few of these concepts have been shown to provide a useful level of measurement accuracy at a practical cost.

There are currently being marketed only a very few endoscopic measurement systems, and their cost is much higher than most of the aircraft inspection market can tolerate. As a result, the actual day to day determination of the size of internal engine defects is still often done by making crude estimates, rather than attempting to make a quantitative measurement.

B. The Necessity of and Requirements for Making Non-Contact Dimensional Measurements Probably the simplest approach to obtaining quantitative object size information is to attach a physical scale to the distal end of the endoscope, and to place this scale in contact with the object to be measured. U. S. Pat. No. 4,721,098 to Watanabe, and U.S. Pat. No. 4,825,259 to Barry, are examples of this approach. The problems with this are that it is often not possible to insert the scale through the available access hole, that the objects of interest are almost never flat and oriented in the correct plane so that the scale can lie against them, that it is often not possible to manipulate the end of the endoscope into the correct position to make the desired measurement, and that it is often not permissible to touch the objects of interest.

These problems have driven work toward the invention of non-contact measurement techniques. A number of such techniques have been developed based on different physical principles. The present invention is based on the principle of optical perspective, and more fundamentally, on the principle of triangulation.

Before reviewing the prior art related to the present invention, it will be useful to briefly discuss the requirements that must be met by any truly quantitative dimensional measurement system based on a fiberscope or a borescope. These requirements have until now not been met by any system of which I am aware.

To make an accurate non-contact measurement of an object viewed through an endoscope, a number of problems must be solved. First, and most important, the magnification of the object changes rapidly as the distance between the object and the optics at the distal end of the endoscope changes. Thus, in order to determine the magnification, this distance must be determined. Second, the object of interest will generally not be oriented perpendicular to the optical axis of the scope; thus, the orientation at which the object lies must be determined. Third, any distortion of the view due either to the endoscope's optical system or any associated viewing hardware, such as a television camera and/or monitor, must be corrected for in the measurement. (Endoscope optical systems almost always have a large amount of distortion.) Fourth, one must address the need for inherent measurement precision and accuracy. That is, all sources of error in the measurement made with a particular system must be evaluated and minimized to the extent allowed by available technology and by cost requirements. Only by evaluating these errors is it possible to determine how their effects can best be minimized through optimum system design.

Nothing is more important to a system of metrology than the accuracy of the measurements it produces. In my view, this proposition has not been given proper consideration in the prior art. Almost without exception, the approach taken has been to suggest a measurement technique without any examination, much less a comprehensive examination, of the measurement accuracy that can be achieved with the suggested technique.

C. Non-Contact Measurements Using Triangulation and Perspective

What I mean by "use of perspective" is the use of two or more views of an object, obtained from different viewing positions, for dimensional measurement of the object. By "dimensional measurement", I mean the determination of the true three-dimensional (height, width, and depth) distance between two or more selected points on the object.

To perform a perspective dimensional measurement, the apparent positions of each of the selected points on the object are determined in each of the views. This is the same principle used in stereoscopic viewing, but here I am concerned with making quantitative measurements of object dimensions, rather than obtaining a view of the object containing qualitative depth cues. As I will teach, given sufficient knowledge about the relative locations, orientations and imaging properties of the viewing optical systems, one can then determine the locations of the selected points in a measurement coordinate system. Once these locations are known, one then simply calculates the desired distances between points by use of the well-known Pythagorean Theorem.

Perspective is related to and based on triangulation, but triangulation is also the principle behind making any measurement of distance using the measurement of angles.

The earliest related art of which I am aware is described in U.S. Pat. No. 4,207,594 to Morris and Grant. The basic approach of this work is to measure the linear field of view of a borescope at the object, then scale the size of the object as measured with video cursors to the size of the field of view as measured with the same cursors. The linear field of view is measured by determining the difference in borescope insertion depth between alignment of the two opposite edges of the field of view with some selected point on the object.

The major problems with this approach are that the three subsidiary requirements for an accurate measurement are not met. This technique cannot determine the depth of the object. In fact, the patent specifies that the user has to know the angle that the plane of the object makes with respect to the plane perpendicular to the borescope line of sight. This information is almost never available in any practical measurement situation. In addition, the technique assumes that there is no distortion, so that the resulting measurement will always be in error from that source as well. The teachings of this patent do not include any discussion of the precision and accuracy of the measurements that can be made with it.

In U.S. Pat. No. 4,702,229, Zobel describes a rigid borescope free to slide back and forth between two fixed positions inside an outer mounting tube, to measure the dimensions of an object. As with Morris and Grant, Zobel does not use the principle of perspective, and thus discusses only the measurement of a flat object, oriented perpendicular to borescope line of sight. Zobel's teachings also fail to address any of the other three requirements for accurate measurements. For instance, with realistic tolerances on the straightness and circularity of the envelope of the borescope, and on the inner bore of the enclosing tube, the repeatability of the borescope position is likely to be poor. This means that the repeatability of the measurement will also be poor.

U.S. Pat. No. 4,820,043 to Diener describes a measurement scope after Zobel (U.S. Pat. No. 4,702,229) with the addition of an electronic transducer on the measurement scale, an instrumented steering prism at the distal end, and a calculator. The principle is that once the distance to the object is determined by the translation of the borescope proper according to Zobel, then the object size can be determined by making angular size measurements with the steerable prism. Again, there is no teaching of the necessity of determining the depth of the object, the distortion of the optical system, and the limits to the precision and accuracy.

U.S. Pat. No. 4,935,810 to Nonami and Sonobe shows explicitly a method to measure the true three-dimensional distance between two points on an object by using two views of the object from different perspectives. They use two cameras separated by a fixed distance mounted in the tip of an endoscope, where both cameras are aligned with their optical axes parallel to the length of the endoscope. This patent does teach a method for correction for a particular type and amount of optical distortion, but this distortion model is unrealistically simple for most endoscope optical systems. Nonami and Sonobe do not discuss the effects of any errors other than operator blunders.

In an attempt to minimize the effects of operator blunders, this patent teaches the production and use of a "guide line" which is used to enforce a certain geometrical relationship between the apparent locations of a point to be measured as viewed from the two perspective positions. In my view, as I will argue later, the use of this "guide line" is actually harmful to the goal of making accurate measurements.

The first three patents listed above do not teach one how to determine the depth of an object, while the final one does. All four of these patents assume that the measurement system is accurately built to a particular geometry. This fact by itself is a significant flaw, since none of these patents teach one how to achieve this perfect geometry. If one attempts to use the technique taught by Nonami and Sonobe, for instance, one must either independently develop a large body of techniques to enable one to build a system accurately to the required geometry, or one must accept measurements of poor accuracy. It should not be surprising that there have been no commercial products based on any of these patents.

A considerably different approach to perspective measurements is represented by two additional patents, which are included here primarily for completeness.

U.S. Pat. No. 4,895,431 to Tsujiuchi, Ohyama, Honda, Badique, and Kikuchi describes a number of ways to mathematically process two images obtained from different positions to derive object contour information. The two images are obtained by bending the end of a fiberscope. The technique assumes a simple linear relationship between the bend angle of the fiberscope and the offset of the nodal point of the optical system to estimate the geometrical relationship of the images. The image processing begins by correcting for distortion, then doing correlations over a series of smaller and smaller sub-images. The patent teaches that one can thereby derive full three-dimensional position data in the overlap region between the images.

The problem with this approach for accurate dimensional measurement is that the bending of the end of a fiberscope is subject to a number of difficult to correct mechanical errors that make its feasibility questionable. In addition, even if the mechanical accuracy problems could be solved, the cost would be extremely high.

U.S. Pat. No. 5,432,543 to Hasegawa, Ohyama, Yamaguchi, and Nonami is an improvement to U.S. Pat. No.

4,895,431, discussed above. The new approach is to estimate the relative positions of the imaging optical system and the object in addition to the previous estimation of the 3D contour of the object, all by using sophisticated image processing. This patent teaches the use of a more general geometry for defining the measurement than do any of the earlier ones. However, the device still requires an absolute calibration of the magnitude of the motion of the endoscope tip, and the patent teaches nothing about how this might be done. The patent even suggests that the system could be used without this calibration by imaging a scale along with the object. That is, this technique returns to the idea of the use of a physical scale to be compared to the object, in order to determine the size of the object.

In one embodiment Hasegawa, et. al. use a rigid borescope mounted on a precision 3D positioner to obtain the many images necessary to their processing system. This would eliminate much of the systematic error to which their system is subject. However, such a system would probably be even more expensive than the one described in U.S. Pat. No. 4,895,431.

SUMMARY OF THE INVENTION

The prior art in this area, while extensive, has been lacking in one or more of the requirements for providing accurate dimensional measurements, especially at a cost that can be borne by industrial users. The present invention resolves these problems and offers additional advantages as well.

It is a first object of this invention to provide a method and apparatus that allow a user to make a truly accurate dimensional measurement. By "truly accurate", I mean that the level of accuracy is limited only by the technology of mechanical metrology and by unavoidable errors made by the most careful user.

It is a second object of this invention to provide a method and apparatus that allow a user to make a usefully accurate measurement at low cost. By "usefully accurate", I mean that the accuracy of the measurement is adequate for the purposes of most common industrial applications. By "low cost", I mean that the user can add this measurement capability to his or her existing remote visual inspection capability with a lower incremental expenditure than is required with the prior art.

It is a third object of this invention to provide a method and apparatus that allow a user to make dimensional measurements over a wider range of measurement conditions than is possible with the prior art.

It is a fourth object of this invention to provide a measurement method that is flexible enough so that it can be used with special purpose hardware to make accurate dimensional measurements in special or unusual situations.

Accordingly, my invention addresses the limitations of the prior art by making innovations in four major areas:

1. I teach the use of a variable geometry apparatus, such that the geometry of the perspective measurement can be adjusted by the user to be optimum for each specific measurement to be performed. This variable geometry is implemented through the use of one or more moving cameras.

2. I teach the use of a complete set of robust calibration procedures, which removes the need for the measurement system to be built accurately to a specific geometry, and also removes any need for the camera(s) to be built accurately to specific optical characteristics. Use of my calibration procedures also enables one to use measurement systems built with special geometries that are particularly suited to unique or unusual measurement problems.

3. I teach the use of apparatus with a high degree of repeatability in the motion of the camera. Once calibration is handled correctly, the repeatability of the camera motion becomes one of the fundamental limits to the error in the measurement.

4. I teach the use of a data processing algorithm which is capable of incorporating all of the calibration data into the measurement, and which also makes optimum use of the available measurement data.

In more detail, with my invention perspective dimensional measurements of an object of interest are made with the use of one or more moving cameras. For each point on the object to be located, two different views of the object are examined. These two views are obtained from camera viewing positions which are separated by a known physical distance that I call the perspective baseline. The use of at least one moving camera enables the perspective baseline to be changed to best suit each different object, or portion of an object, to be measured.

I show that in general there is an optimum perspective baseline. This optimum perspective baseline is such that the angle subtended at a point of interest on the object by the perspective baseline is substantially the same, independent of the position of the point of interest with respect to the two camera viewing positions.

In distinction to the prior art in perspective dimensional measurements, in which the perspective baseline has always been fixed, this new system has three extremely important and non-obvious advantages. The first advantage is that the random errors in the measurement are much smaller. The second advantage is that there is no minimum distance at which measurements can be made. The third advantage is that measurements can be made which are simply impossible to make when the distance between the camera viewing positions is fixed.

I teach two modes of perspective distance measurement. A first measurement mode has some similarities to the perspective measurement taught by the prior art, but my variable perspective baseline enables the user to achieve the first two of the advantages listed above. A second measurement mode is unique to my system, and it provides the user with the third advantage, as well as the first two.

With my system, unlike the prior art, the measurement hardware does not need to be built perfectly to a specific geometry. Instead, I teach how to calibrate the geometry of the hardware, and how to take that actual geometry into account in the measurement process. This ability to handle a general measurement geometry means that a perspective dimensional measurement can be made with any arbitrary motion of the camera(s) and that the camera motion can be selected to be optimum for the purposes of each specialized application. It also means that accurate measurements can be made with systems that are relatively inexpensive.

The complete set of calibration procedures I teach includes three different types of calibration. In optical calibration, the characteristics of each camera, when used as a precision image forming device, are correctly determined. In alignment calibration, the position(s) and orientation(s) of the camera(s) with respect to the motion(s) are determined. Finally, in motion calibration, any errors in the actual motion(s) of the camera(s), as compared to the ideal motion(s), are determined.

In the preferred embodiments of my system, the motion of a single camera is constrained to lie along a substantially straight line. The straight line motion is provided by the use of a linear translation stage, while the position of the camera along its line of motion is determined with either a micrometer or a linear position transducer.

In certain of the preferred embodiments, the camera is chosen to be a standard, substantially side-looking, rigid video borescope. Together with my calibration techniques, these embodiments allow the user to make accurate dimensional measurements using the standard video borescope equipment that he or she already owns, something that is not possible using the prior art.

In the preferred embodiments, at each viewing position the image formed by the camera is displayed on a video monitor, and image position measurements are made by moving cursors which are superimposed on the video signal to coincide with one or more selected points on the image of the object. This system is simple to add to existing video borescope equipment, and its performance is at least as good as a more expensive digital video system would be.

With the preferred embodiments, the optimum perspective baseline is automatically obtained simply by adjusting the position of the camera so that the object point(s) of interest appear(s) substantially on one side of the field of view of the camera at the first camera position, and substantially on the other side of the field of view at the second camera position.

In my system, I teach a data processing algorithm which combines all of the measured image position data, together with all of the calibration data, to calculate a least squares estimate of the position of the point of interest in the measurement coordinate system. This is an advantage over certain of the prior art which explicitly teaches that one should discard some of the image position data, and is an advantage over all of the prior art, none of which is capable of incorporating the calibration data.

Further objects, advantages, and features of my system will become apparent from a consideration of the following description and the accompanying schematic drawings.

DESCRIPTION OF THE DRAWING

FIG. 7 shows two views of the video monitor as seen by the user during the first stage of a second distance measurement procedure.

FIG. 20 is a left side elevation view of the mechanical portion of a second embodiment of the invention.

FIG. 22 is a perspective view of a third embodiment of the invention.

FIG. 23 is a plan view of the internal structures of the distal end of the third embodiment.

FIG. 24 is a left side elevation view of the internal structures of the distal end of the third embodiment.

FIG. 25 is a right side elevation view of the internal structures of the distal end of the third embodiment.

FIG. 26 is a plan view of the internal structures of the proximal end of the third embodiment.

FIG. 27 is a left side elevation view of the internal structures of the proximal end of the third embodiment.

FIG. 28 is a right side elevation view of the internal structures of the proximal end of the third embodiment.

FIG. 30 is a block diagram of the electronics of the third embodiment.

FIG. 31 is a plan view of the internal structures of the distal end of a fourth embodiment.

FIG. 32 is a left side elevation view of the internal structures of the distal end of the fourth embodiment.

FIG. 39 illustrates the process of calibration of rotational errors of the translation stage used in the third and fourth embodiments.

FIG. 39A shows an enlarged view of the components mounted to the translation stage during the calibration process depicted in FIG. 39.

FIG. 43 shows a general relationship between the viewing coordinate systems at the two viewing positions.

FIG. 44 shows the definition of the error analysis coordinate system. The angle Θ is the angle subtended at the point of interest by the distance between the viewing positions.

List of Reference Numerals

Figure 1:
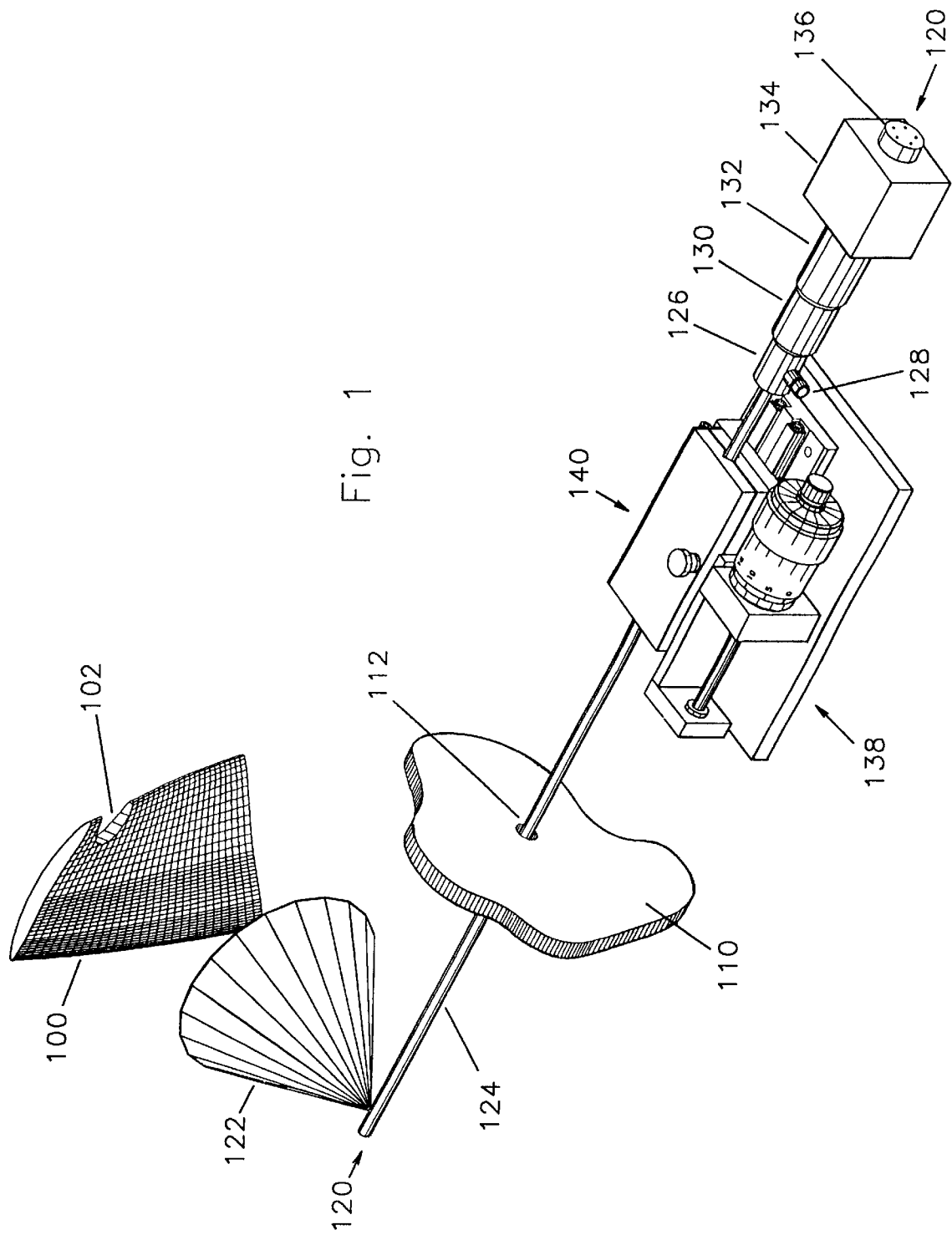
FIG. 1 is a perspective view of the mechanical portion of a first embodiment of the invention and its use in a typical measurement situation.

100 Object Under Inspection
102 Damage or Feature of Interest
110 Enclosure Wall
112 Inspection Port
120 Video Borescope
121 Objective Lens
122 Field of View
123 Prism
124 Lens Tube
126 Illumination Interface Adapter
127 Illumination Fiber Bundle
128 Fiber Optic Connector
129 Fiber Output Surface
130 Focusing Ring
132 Video Adaptor
134 Video Camera Back
135 Camera Control Cable
136 Camera Connector
137 Video Cable
138 Borescope Positioning Assembly (BPA)
140 Borescope Clamp
142 Lower V-Block
144 Upper V-Block
146 Resilient Layer
148 Hinge
150 Clamping Screw List of Reference Numerals -continued 162 Baseplate
166 Micrometer Mounting Block
168 Micrometer
170 Extension Shaft
172 Distance Scale
174 Actuator Arm
176 Bushing
178 Micrometer Drum
180 Translation Stage
182 Fixed Base
184 Moving Table
186 Roller Slides
200 Illumination Controller
202 Illumination Cable
206 Fiber Optic Cable
212 Camera Controller
214 Video Monitor
216 Video Recorder
220 Solid State Imager
221 Imager Controller
222 Imager Cable
224 Miniature Video Camera
228 Computer
230 Cursor Controller
310 Video Screen
312 Borescope Apparent Field of View
314 Object Image
316 Cursor A
318 Cursor B
360 Linear Position Transducer
361 Transducer Operating Rod
362 Linear Scale Body
363 Scale Body Mounting Bracker
364 Scale Read Head
365 Read Head Mounting Bracket
366 Position Transducer Cable
367 Transducer Mounting Bracket
369 Transducer Attachment Bracket
371 Transducer Cable Clamp
388 Rearward Stop Positioner
390 Forward Stop Positioner
392 End Stop
393 End Stop Insert
394 Adjusting Nut Bracket
396 Fixed Nut
398 Adjusting Screw
400 Adjusting Screw Knob
402 Adjusting Screw Tip
404 Dovetail Slide
406 Bracket Position Locking Handle
407 Locking Cam
410 Motion Actuator
411 Actuator Cable
412 Air Cylinder
413 Actuator Output Shaft
418 Extension Rod
420 Air Port
422 Actuator Mounting Bracket
424 Actuator Attachment Bracket
426 Actuator Attachment Bushing
428 Actuator Cable Assembly
440 Stop Pin Hole
450 System Controller
452 Motion Controller
470 Position Measurement Block
482 Positioning Cable
484 Positioning Pulley
485 Pulley Mounting Shaft
486 Distal Motion Clamp
487 Pulley Support Bracket
488 Proximal Motion Clamp
490 Distal Cable Stabilizer Clamp
491 Distal Stabilizer Slot
492 Distal Fiber Clamp
494 Fiber End Clamp
496 Proximal Motion Stage
498 Bulkhead
499 Proximal Stage Support Bracket -continued List of Reference Numerals 500 Electronic Measurement Borescope (EMB)
502 Electronic Connector
510 Proximal Housing
512 Borescope Probe Tube
514 Distal Baseplate
516 Proximal Baseplate
518 View Port
532 Positioning Wire
534 Positioning Wire Sheath
536 Distal Sheath Clamp
538 Flexible Endoscope Envelope
540 Distal Rigid Housing
542 Distal Positioning Wire Clamp
544 Distal End Cable Clamp
546 Cable Centering Member
550 EMB Translation Stage Subassembly
600 Stage Calibration Baseplate
602 Collimator V-Block
604 Electronic Autocollimator
606 EMB Subassembly V-Block
608 Actuator Mounting Block
610 Stage Calibration Actuator
612 Actuator Operating Rod
614 Stage Operating Arm
618 Mirror Platform
620 Mirror Mount
622 Longitudinal Mirror
624 Transverse Mirror

DESCRIPTION OF A FIRST EMBODIMENT

FIG. 1 shows a view of the mechanical portion of a basic embodiment of the present invention and its use in a typical measurement situation. In FIG. 1, an object 100 with a damaged area or feature of interest 102 is being viewed with a video borescope system 120. Object 100 is completely enclosed by an enclosure 110. In FIG. 1 only a small portion of the wall of enclosure 110 is shown. The borescope has been inserted through an inspection port 112 in the wall of enclosure 110.

The borescope is supported by and its position is controlled by a mechanical assembly that I call the borescope positioning assembly (BPA), which is denoted by 138 in FIG. 1.

Several features of video borescope system 120 are shown in FIG. 1 to enable a better understanding of my invention. The configuration shown is meant to be generic, and should not be construed as defining a specific video borescope to be used with my invention.

Conical field of view 122 represents the angular extent of the field visible through the borescope. The small diameter, elongated lens tube 124 comprises the largest portion of the length of the borescope. The remainder of the borescope is comprised successively of an illumination interface adapter 126, a focusing ring 130, a video adapter 132, and a video camera back or video sensor 134. Video camera back 134 represents every element of a closed circuit television camera, except for the lens. Video adapter 132 acts to optically couple the image formed by the borescope onto the image sensing element of video camera back 134 as well as serving as a mechanical coupling.

Illumination adapter 126 provides for the connection of an illumination fiber optic cable (not shown) to the borescope through a fiber optic connector 128. The illumination (not shown) exits lens tube 124 near the apex of field of view cone 122 to illuminate objects contained within cone 122.

A camera connector 136 connects video camera back 134 to its controller (not shown) through a cable which is also not shown.

The portion of BPA 138 which directly supports the borescope is a clamp assembly 140, which clamps lens tube 124 at any convenient position along its length, thereby supporting the weight of borescope 120 and determining its position and orientation. BPA 138 is itself supported by a structure which is attached to enclosure 110 or to some other structure which is fixed in position with respect to object 100. This support structure is not part of the present invention.

Figure 2:
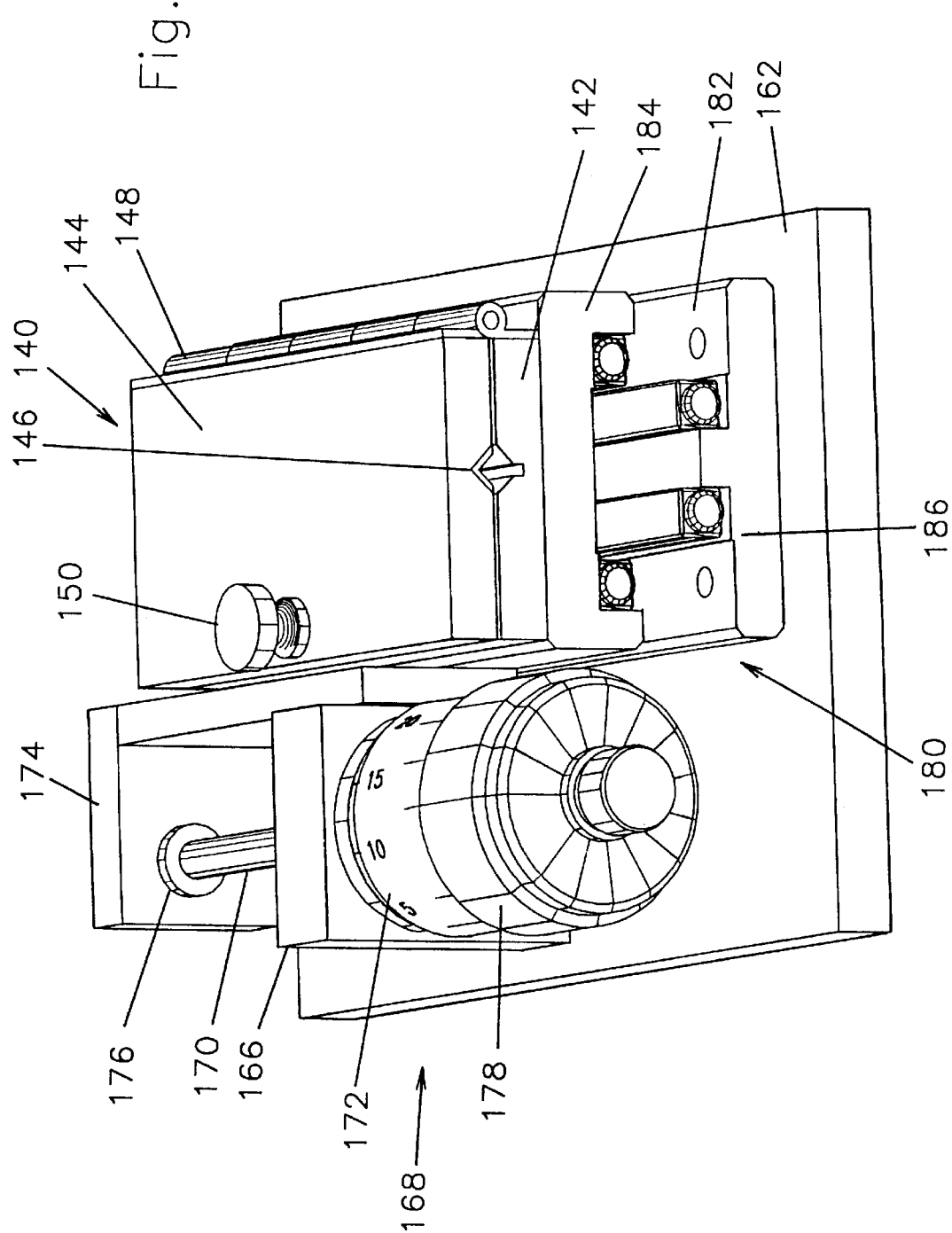
FIG. 2 is a detailed perspective view of the mechanical portion of the first embodiment of the invention.

BPA 138 is shown in more detail in FIG. 2. Lens tube 124 has been removed from clamp 140 in this view for clarity. Clamp 140 is comprised of a lower V-block 142, an upper V-block 144, a hinge 148, and a clamping screw 150. The upper V-block is lined with a layer of resilient material 146, in order that the clamping pressure on the lens tube 124 can be evenly distributed over a substantial length of the tube.

Lower V-block 142 is attached to moving table 184 of a translation stage or slide table 180. Translation stage 180 is a standard component commercially available from several vendors, and it provides for a smooth motion of moving table 184 which is precisely constrained to a straight line. Translation stage 180 consists of moving table 184 and a fixed base 182, connected by crossed roller bearing slides 186. Fixed base 182 is attached to a BPA baseplate 162.

The bearings in translation stage 180 could also be either ball bearings or a dovetail slide. Such stages are also commercially available, and are generally considered to be less precise than those using crossed roller bearings, though they do have advantages, including lower cost. Translation stage 180 could also be an air bearing stage, which may offer even more motion accuracy than does the crossed roller bearing version, although at a considerable increase in system cost and complexity.

Also attached to BPA baseplate 162 is a micrometer mounting block 166. Mounting block 166 supports a micrometer 168. Micrometer 168 has an extension shaft 170, a rotating drum 178, and a distance scale 172. As drum 178 is rotated, a precision screw inside the micrometer rotates inside a precision nut, thus changing the distance between the end of extension shaft 170 and mounting block 166. Of course, micrometer 168 could be a digital unit, rather than the traditional analog unit shown.

Micrometer extension shaft 170 is connected to an actuator arm 174 through a bushing 176. Actuator arm 174 is mounted to moving table 184. Bushing 176 allows for a slight amount of non-parallel motion between micrometer extension shaft 170 and moving table 184, at the cost of allowing some backlash in the relative motions of table 184 and shaft 170. Micrometer scale 172 can be read to determine the position of moving table 184 within its range of motion.

Figure 3:
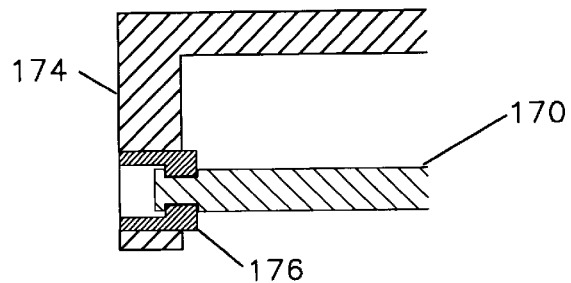
FIG. 3 is a cross-sectional view of a portion of the structure shown in FIG. 2.

FIG. 3 shows a detailed view of bushing 176 and the interface between micrometer extension shaft 170 and actuator arm 174. Shaft 170 is captured within bushing 176 so that arm 174 will follow position changes of shaft 170 in either direction, with the previously mentioned small amount of backlash.

Figure 4:
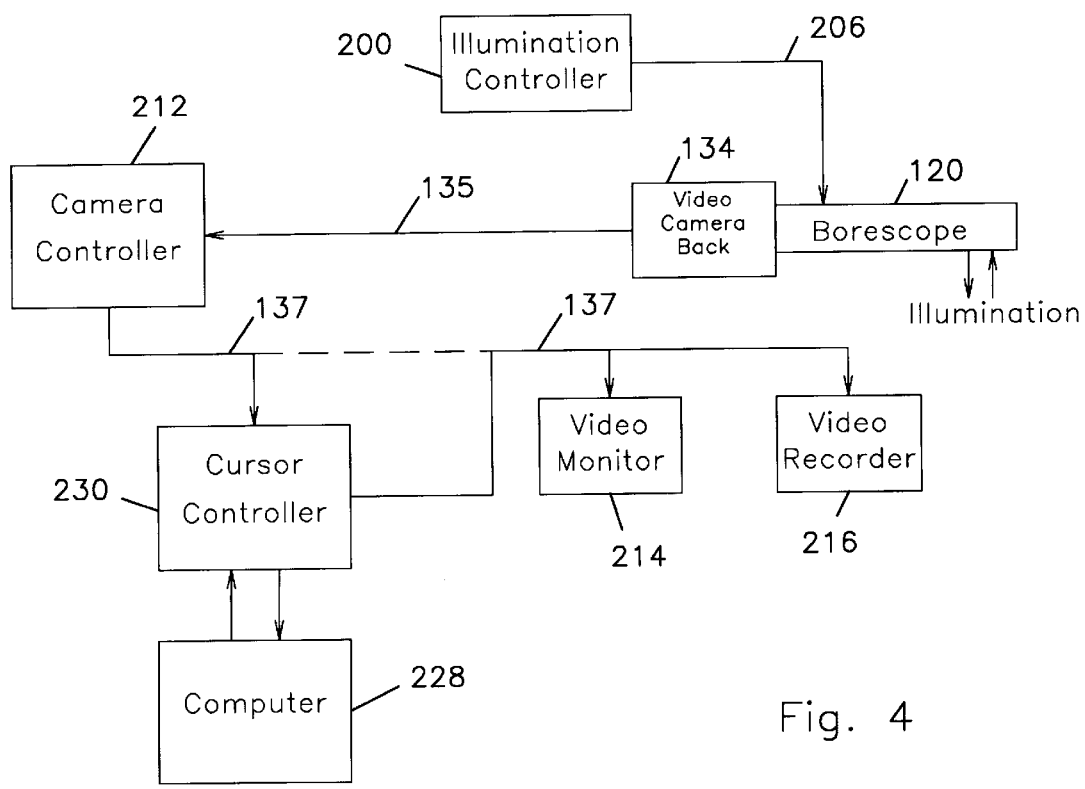
FIG. 4 is a block diagram of the electronics of the first embodiment of the invention.

FIG. 4 shows a block diagram of the electronic portion of the first embodiment. FIG. 4 represents the electronics of a standard, known borescope video system except for the addition of a cursor controller 230 and a computer 228. In FIG. 4, an illumination controller 200 is connected to the borescope through a fiber optic cable 206 as has previously been described. Video camera back 134 is connected to camera controller 212 through camera control cable 135 as has also been described. For the known system, the video signal out of the camera controller is connected to a video monitor 214 and, optionally, to a video recorder 216, through a video cable 137 as shown by the broken line in FIG. 4. For the present invention, the video signal from camera controller 212 is instead sent to cursor controller 230. The video signal as modified by cursor controller 230 is then supplied to video monitor 214 and to video recorder 216. Use of video recorder 216 is optional, though its use makes it possible for the user to repeat measurements or to make additional measurements at some later time, without access to the original measurement situation, as described below.

Figure 5:
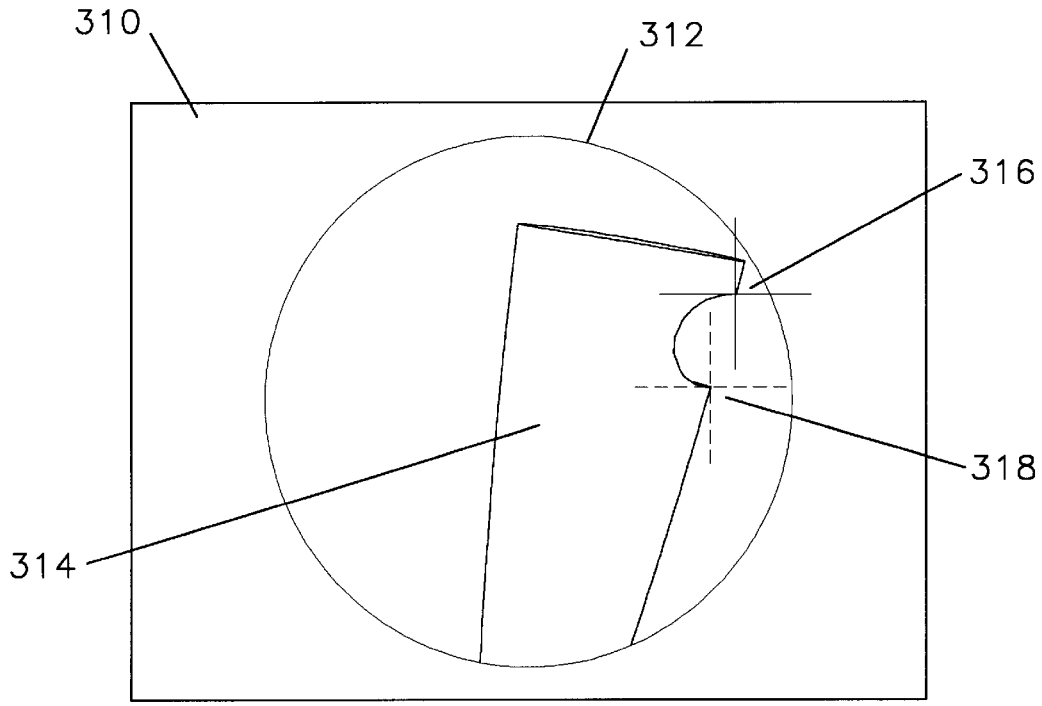
FIG. 5 is a view of the video monitor as seen by the user during the first stage of a first distance measurement procedure.

FIG. 5 shows a view of the video monitor as seen by the user. On video screen 310 there is seen a circular image of the borescope field of view, which I call the apparent field of view, 312. Inside apparent field of view 312 is shown an image of the object under inspection 314. Superimposed on video screen 310, and hence on image 314, are a pair of cross-hairs, fiducial marks, or cursors, 316 (Cursor A) and 318 (Cursor B). According to my invention, these cursors can be moved to any portion of the video screen, and can be adjusted in length, brightness, and line type as required for best alignment with points of interest on image 314. Note that these cursors do not need to be cross-hairs; other easily discernible shapes could also be produced and be used as well.

The generation of video cursors is well known by those familiar with the art, so is not part of this invention.

The functions of cursor controller 230 are controlled by computer 228 (FIG. 4). Computer 228 has a user interface that allows manipulation of the cursor positions as desired. It also provides a means for the user to indicate when a given cursor is aligned appropriately, so that an internal record of the cursor position can be made. It provides means for the user to input numerical data as read from micrometer scale 172. In addition, computer 228 contains software which implements algorithms to be described which combine these numerical data appropriately to derive the true three dimensional distance between points selected by the user. Finally, computer 228 provides a display means, whereby the distance(s) determined is (are) displayed to the user. Clearly, this display could be provided directly on video screen 310, a technology which is now well known, or it could be provided on the front panel or on a separate display screen of computer 228.

Operation of the First Embodiment

As discussed previously for the prior art, the view of the object shown in FIG. 5 has the problem that it is a two-dimensional projection of a three-dimensional situation. Clearly the combination of cursor controller 230 and computer 228 is capable of making relative measurements of the apparent size of features on object image 314, as is well known. But, because there is no information on distance, and because the distance may vary from point to point in the image, there is no way to determine the true dimensions of object feature 102 from image 314.

Figure 6:
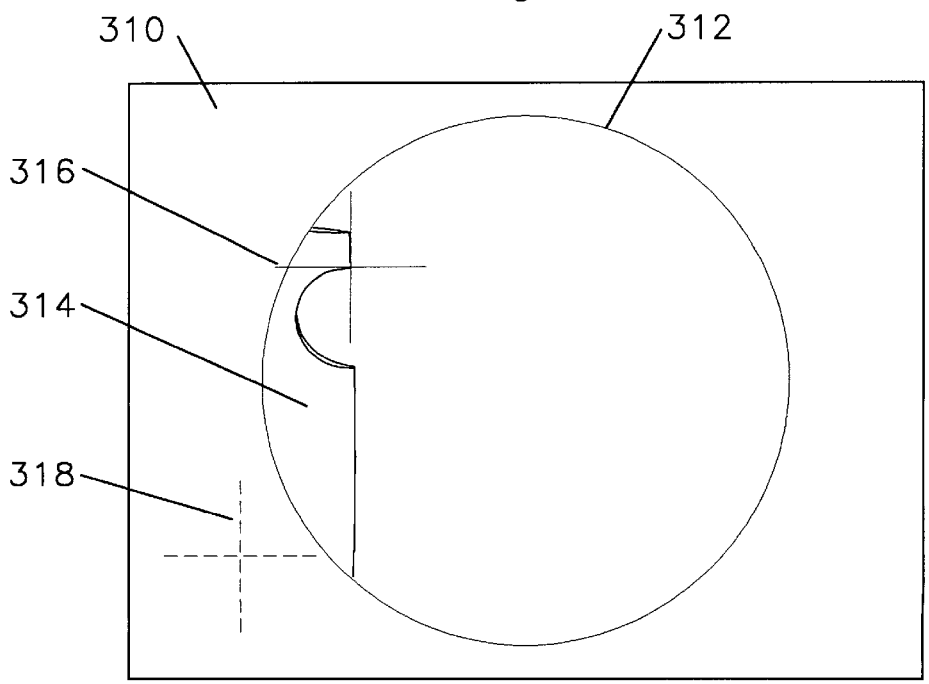
FIG. 6 is a view of the video monitor as seen by the user during the second stage of a first distance measurement procedure.

The solution offered by my invention is to obtain a second view of the object as shown in FIG. 6. This second view is obtained by translating video borescope 120 a known distance along an accurate straight line path using BPA 138 described above. This technique has several important and non-obvious advantages over the prior art, as will be shown.

The following discussion of the operation of my invention assumes that it is the distance between two points on the object which is to be determined. As will become clear, it is straightforward to extend the measurement process to as many points as desired. In the case of more than two points, the distances between all other points and one particular reference point could be determined by the process described below. Additionally, the distances between all of the points taken as pairs could be determined from the same data gathered during this process.

I will now outline a first mode of distance measurement operation. As was shown in FIG. 5, to begin the process the borescope is aligned with the object to produce a view where the points of interest are located substantially on one side of the field of view. In that view, cursor A (316) and cursor B (318) are aligned with the two points of interest, respectively, as shown in FIG. 5. When the cursors are aligned correctly, the user indicates this fact through the user interface of computer 228, and computer 228 records the locations of cursors A and B. The user also then enters the position of moving table 184 as indicated on micrometer distance scale 172.

Using micrometer 168, the user then repositions the borescope to obtain a second view of object 100. As shown in FIG. 6, the user selects a second position of the borescope to bring the points of interest to substantially the other side of the borescope FOV as compared to where they were in the first view. The cursors are then once again used to locate the positions of the points of interest, cursor A for point A and cursor B for point B. In FIG. 6, Cursor B (318) is shown temporarily moved to an out of the way position to avoid the possibility of confusion when the user is aligning cursor A with Point A. The user has the option of aligning and recording the cursor positions one at a time, if desired. When the cursors are positioned correctly, or when each cursor is positioned, if they are being used one at a time, the user indicates that fact through the user interface of computer 228. The user then enters the new position of moving table 184 as indicated on micrometer distance scale 172.

With the data entered into computer 228, (two cursor position measurements for each point of interest and two borescope position measurements) the user then commands the computer to calculate and display the true three dimensional distance between the points which were selected by the cursors. The computer combines the measured data with calibration data to determine this distance in a software process to be described further below. The calibration data can be obtained either before the measurement or after the measurement, at the option of the user. In the latter case, computer 228 will store the acquired data for future computation of the measured distance. Also, in the case of post-measurement calibration, the user has the option of directing computer 228 to use preliminary or previously obtained calibration data to provide an approximate indication of the distance immediately after the measurement, with the final distance determination to depend on a future calibration.

The measurement process just outlined is that expected to be the one most generally useful and convenient. However, there is no requirement to use two separate cursors to determine the apparent positions of two points on the object, because one cursor would work perfectly well as long as the cursor position data for each point of interest are kept organized properly. In addition, it may be that the distances between more than a single pair of points is desired. In this case, there are just more data to keep track of and nothing fundamental has changed.

Figure 8A:
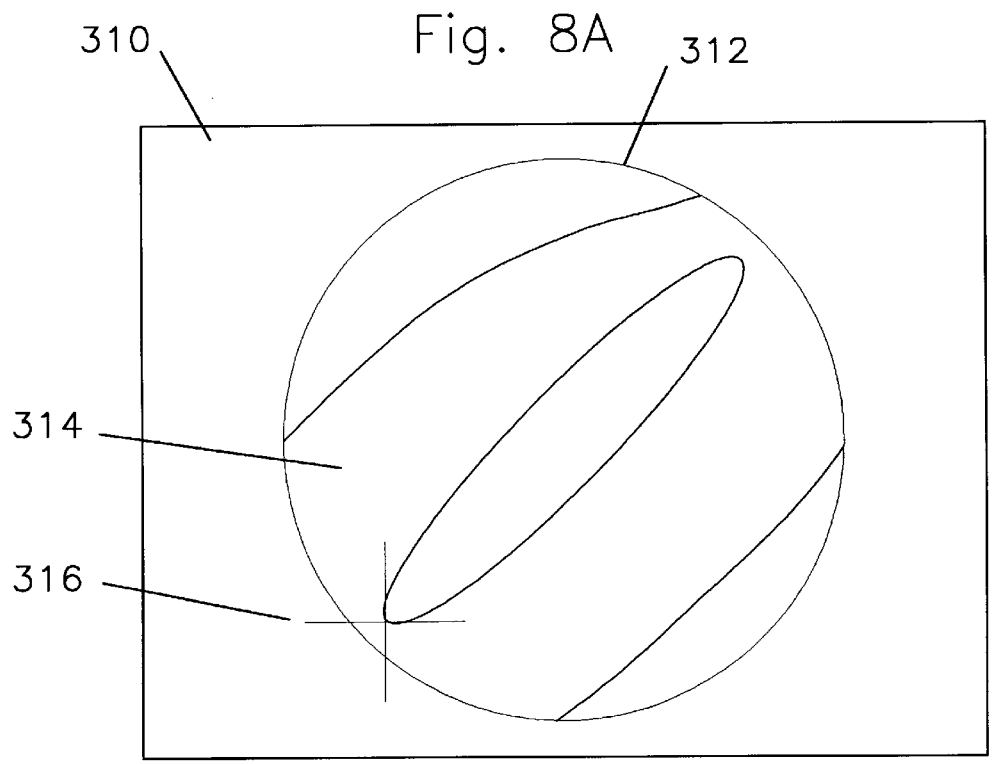
FIG. 8 shows the two views of the video monitor as seen by the user during the second stage of a second measurement procedure.
Figure 8B:
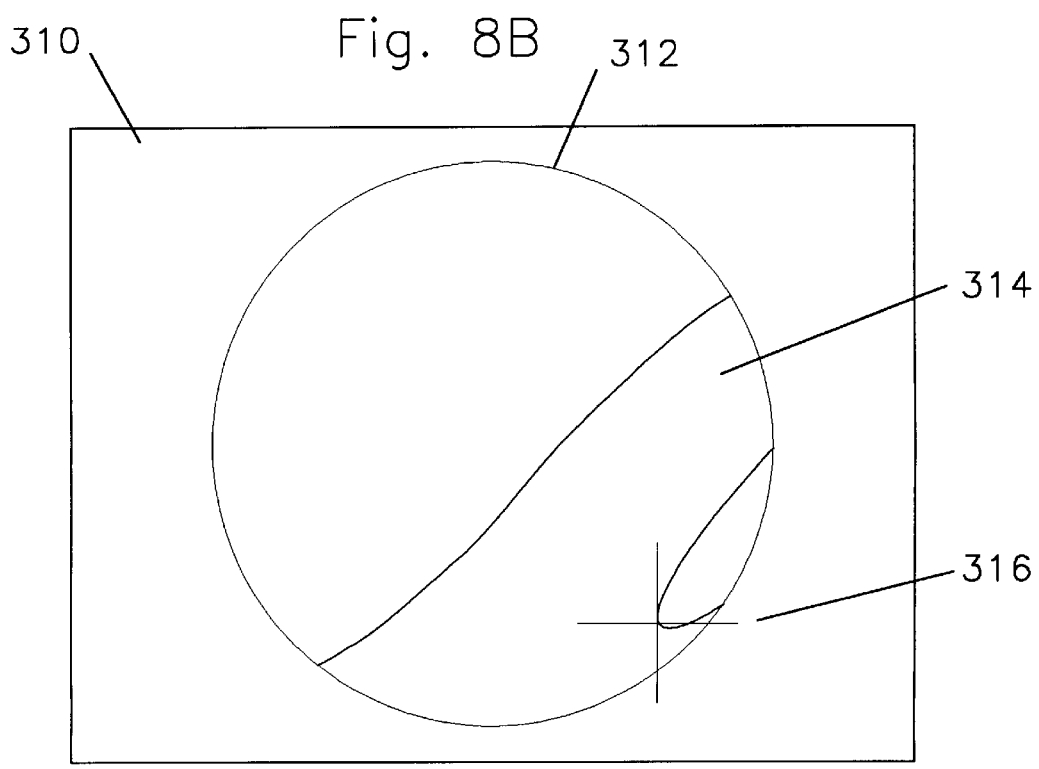

I now outline a second mode of distance measurement operation. Consider measurement of the distance between two points which are so far apart that both points cannot lie on substantially the same side of apparent field of view 312. FIGS. 7 and 8 show an example of this situation, where the three-dimensional distance between the two ends of an elliptical feature is to be determined. FIGS. 7A and 7B show the two steps involved in the determination of the three dimensional location of the first end of the elliptical feature. FIGS. 8A and 8B show the two steps involved in the determination of the three dimensional location of the second end of the elliptical feature. In this mode of distance measurement, a point of interest on the object is first brought to a location on one side of apparent field of view 312 and a cursor is aligned with it. The cursor position and micrometer position data are then stored. The view is then changed to bring the point of interest to the other side of apparent field of view 312, and the cursor position and micrometer position data are once again stored. This same process is carried out sequentially for each point of interest on the object. After all of the cursor and micrometer position data are gathered, the computer is instructed to calculate the desired distances between points.

Note that in this second mode of distance measurement operation, the two points of interest could be located so far apart that they could not both be viewed at the same time. In this case the measurement still could be made. That is, there is no requirement that the distance to be measured be completely containable within apparent field of view 312. The only limit is that two suitable views of each point be obtainable within the translation range of BPA 138. This is a capability of my invention that was not conceived of by any of the prior art, and is not possible using any of that art.

In detail, the process of making a measurement of the distance between two points, both of which are contained within a relatively small portion of apparent field of view 312 as shown in FIGS. 5 and 6, (I call this measurement mode 1) is made up of the following steps:

1. A specific area of interest on object image 314 is located in apparent field of view 312 by sliding and rotating borescope 120 inside borescope clamp 140.
2. Borescope clamp 140 is locked with clamping screw 150 to secure the position and orientation of the borescope with respect to BPA 138.
3. Micrometer drum 178 is rotated to select a first view of the object, with both points of interest located substantially on one side of apparent field of view 312, such as that shown in FIG. 5. The approximate position of the micrometer as read from scale 172 is noted.
4. Micrometer drum 178 is rotated to select a second view of the object, such as that shown in FIG. 6. This step insures that a suitable view is, in fact, obtainable within the range of motion of micrometer 168, and that, for instance, the view is not blocked by intervening objects.
5. Micrometer drum 178 is then rotated back again to approximately the position selected for the first view. At this point, the rotation of the micrometer is again reversed so that the micrometer is being rotated in the direction that is necessary to move from the first view to the second view. After a sufficient reverse rotation to ensure that the backlash of bushing 176 has been taken up, the micrometer rotation is halted. This is now the selected viewing position for the first view.
6. Cursors 316 and 318 are then aligned with the selected points on object image 314 using the user interface provided by computer 228.
7. When each cursor is aligned correctly, computer 228 is commanded to store the cursor positions. The cursors can be aligned and the positions stored either sequentially, or simultaneously, at the option of the user.
8. The user reads micrometer scale 172 and enters the reading into the computer with the user interface provided.
9. Micrometer drum 178 is now carefully rotated in the direction necessary to move from the position of the first view to the position of the second view. This rotation stops when the user judges the second view to be satisfactory for the purposes of the measurement desired, such as that shown in FIG. 6.
10. The user repeats steps 6, 7, and 8.
11. The user commands the computer to calculate and display the true three-dimensional distance between the points selected by the cursors in steps 6 and 10. If desired, the computer can be commanded to also display the absolute positions of each of the two points. These absolute positions are defined in a coordinate system to be described below.

In detail, the process of making a measurement of the distance between two points, when they cannot both be contained within a relatively small portion of the apparent field of view 312 as shown in FIGS. 7 and 8, (I call this measurement mode 2) is made up of the following steps:

1. Computer 228 is instructed to command cursor controller 230 to produce a single cursor. While it is not absolutely necessary to use a single cursor, I believe that the use of a single cursor helps avoid unnecessary confusion on the part of the user.
2. The user adjusts micrometer 168 to approximately the midpoint of its range by rotating drum 178.
3. A specific area of interest on object image 314 is located in apparent field of view 312 by sliding and rotating borescope 120 inside borescope clamp 140. The two points of interest are identified, and the borescope is positioned so that the center of apparent field of view 312 is located approximately equidistant between the two points of interest.
4. Borescope clamp 140 is locked with clamping screw 150 to secure the position and orientation of the borescope with respect to BPA 138.
5. Micrometer drum 178 is rotated to select a first view of the first point of interest. The first view is selected so that the point of interest is located substantially on one side of apparent field of view 312, such as that shown in FIG. 7A. The approximate position of the micrometer as read from scale 172 is noted.
6. Micrometer drum 178 is rotated to select a second view of the first point. The second view is selected so that the point of interest is located substantially on the other side of apparent field of view 312 from where it was in the first view, such as that shown in FIG. 7B. This step insures that a suitable view is, in fact, obtainable within the range of motion of micrometer 168, and that, for instance, the view is not blocked by intervening objects.
7. Steps 5 and 6 are repeated for the second point of interest, as depicted in FIGS. 8A and 8B. This step ensures that suitable views are, in fact, obtainable for the second point of interest with the borescope alignment chosen in step 3.
8. Micrometer drum 178 is then rotated to approximately the position selected for the first view of the first point of interest (Step 5). At this point, the user makes sure that the micrometer is being rotated in the same direction that is necessary to move from the first view to the second view of the first point of interest. After a sufficient rotation to ensure that the backlash of bushing 176 has been taken up, the micrometer rotation is halted. This is now the selected position for the first view of the first point of interest.

9. The cursor is then aligned with the first point of interest on object image 314 using the user interface provided by computer 228.
10. When the cursor is aligned correctly, computer 228 is commanded to store the cursor position.
11. The user reads micrometer scale 172 and enters the reading into the computer with the user interface provided.
12. Micrometer drum 178 is now carefully rotated in the direction necessary to move from the position of the first view to the position of the second view. This rotation stops when the user judges the second view to be satisfactory for the purposes of the measurement desired.
13. The user repeats steps 9, 10, and 11.
14. Micrometer drum 178 is rotated to obtain the first view of the second point of interest, which was selected during step 7. The user repeats step 8 for this first view of the second point of interest.
15. The user repeats steps 9 to 13 for the second point of interest.
16. The user commands the computer to calculate and display the true three-dimensional distance between the points. If desired, the computer can be commanded to also display the absolute positions of each of the two points, in the coordinate system to be defined below.

I have repeatedly emphasized that the user should position the points of interest first on one side of apparent field of view 312, then to the other side, during the measurement process. The reasons for and the importance of this will be explained below, and at greater length in a section entitled "Error Analysis; How to Achieve the Best Measurement Precision". In short, this part of the procedure ensures that the optimum conditions for measurement precision, hence accuracy, are obtained automatically.

It should be clear that once such a measurement has been carried out, if video recorder 216 (FIG. 4) were used to make a record of the measurement, then the recording could be played back and additional measurements could be made at a later time. In this case one would simply attach the video output of recorder 216 to the video input of cursor controller 230. There then would be seen a record of the previous measurement process, as shown in FIGS. 5 and 6 or 7 and 8. There would be seen two sets of cursors, one set that was recorded and a second set that would be under current user control. The confusion between these cursors could be eliminated by selecting different cursor parameters (length, brightness, and/or line type) for the viewing of the record than were used by the original measurement. Provided only that a permanent record had been made of the micrometer reading for each viewing position in the original measurement, it would be quite feasible to make additional measurements on the object, after the fact. This might be used, for instance, as a quality control measure, to check measurements that are questioned for some reason.

It should also be clear that the measurement process and mechanical hardware I have defined could be used with borescopes other than video borescope 120 as I have described it. For instance, the video borescope could be implemented with a tiny video camera and lens located at the distal end of a rod or tube without changing this invention at all. In such an "electronic borescope" there would be no need of a lens train to conduct the image from the distal end to the proximal end. While flexible electronic endoscopes built this way are currently available, I am not aware of a rigid borescope like this. However, when one considers that optical components keep getting more expensive while solid state imagers keep getting less expensive and that the resolution of solid stage imagers keeps increasing, it seems likely that electronic borescopes will be used at some future time, especially in the longer lengths, where the optical performance of ordinary borescopes is degraded. (I will later describe an electronic measurement borescope; here I am speaking of an electronic borescope that contains no inherent measurement capability.)

This invention could also be used with a visual borescope, that is, one with no video at all, requiring only that the borescope eyepiece contains an adjustable fiducial mark with a position readout (a device commonly called a "filar micrometer"). Such an embodiment of the invention, while feasible, would have the strong disadvantage of requiring the manual transcription of fiducial position data, which would be a source of errors. It also would have the disadvantage of requiring the user to perform a delicate and precise task, namely accurately aligning the fiducial mark with a selected point on the image of the object, while under the physical stress of looking through the borescope. (In general the borescope would be located at a position awkward for the user). And, of course, such a visual measurement borescope would not be a standard component, unlike the video borescope I have discussed.

It is also clear that the video system could be a digital video system as well as the analog system I have discussed. That is, the video signal could be digitized into discrete "pixels" with a video "frame grabber" and all video processing could be done digitally. Such systems are well known in the art, but have little advantage and considerable cost disadvantage compared to the system I have described for the simple measurement task I have defined.

In the measurement processes that have just been described, the experimental data obtained are four image position coordinates ($x'_{im1}$, $x'_{im2}$, $y'_{im2}$) for each object point of interest and the reading of the micrometer at each viewing position. Computer software combines these measured quantities, together with calibration data, in an optimum way to determine the distance between the two points of interest. I now explain this process, with reference to FIGS. 9 and 10. This explanation uses some higher mathematics which the interested reader will find fully explained in the section entitled "Theory of Operation".

Figure 9:
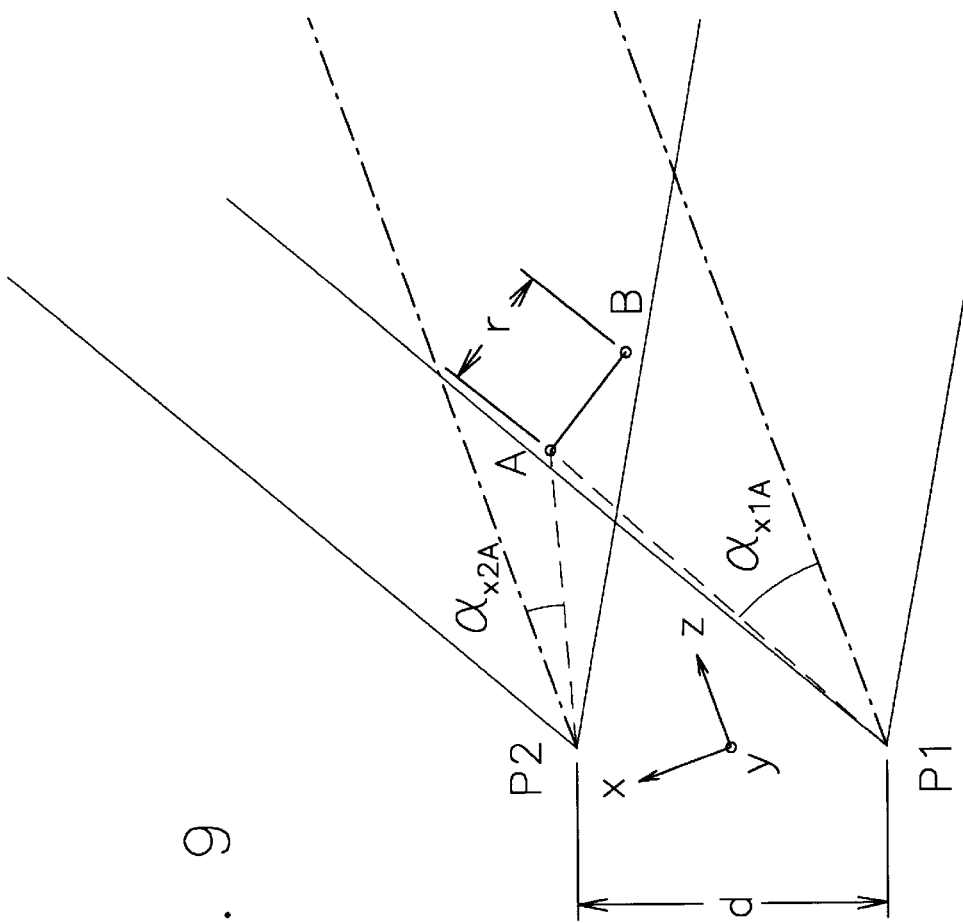
FIG. 9 depicts a first mode of the dimensional measurement process taught by the present invention.

I begin by discussing measurement mode 1. In FIG. 9 two points of interest, A and B, are viewed from two camera positions, P1 and P2. The fields of view of the camera at the two positions are indicated by the solid lines emanating from P1 and P2, while the camera optical axes are denoted by the dot-dash lines. Dashed lines indicate schematically the angles at which point A is viewed from both positions. Similar lines are omitted for the views of point B to keep the Figure uncluttered.

Figure 10:
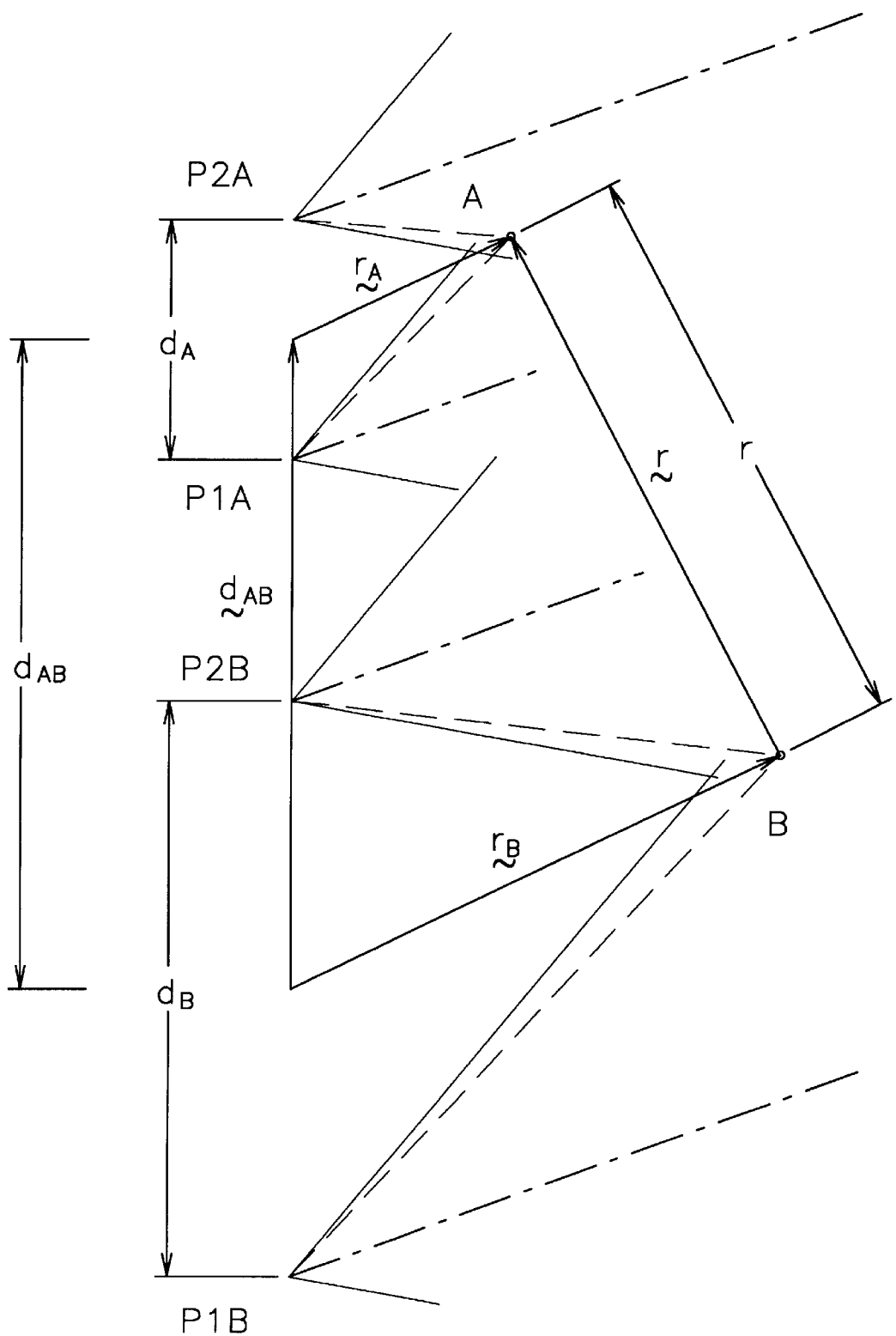
FIG. 10 depicts a second mode of the dimensional measurement process taught by the present invention.

Notice that I have generalized the discussion from the use of a moving rigid borescope to the use of a moving camera. The camera in FIGS. 9 and 10 represents the function of the complete video borescope system 120 as shown in FIG. 1. Of course, the camera in FIGS. 9 and 10 could be any other type of camera or imaging system as well.

The distance between P1 and P2 is d, and is simply calculated from the experimental data as $d=l_2-l_1$, where $l_1$ and $l_2$ are the micrometer readings at viewing positions P1 and P2 respectively. I call the distance d the perspective baseline. A Cartesian coordinate system is set up with its origin midway between P1 and P2. This coordinate system is aligned with the coordinate axes defined by the camera at position P1, that is, the x coordinate is aligned with the x axis of the camera and likewise for y and z. The camera z axis is defined to be the camera's optical axis.

FIG. 9 is drawn in the plane of the x and z coordinates I have just defined. A vector drawn from P1 to P2 is not necessarily contained in this plane, and neither are the points of interest A and B. In other words, the dimensions d and r are not necessarily contained in the plane of FIG. 9.

Because I use an accurate translation stage to translate the camera (borescope) between P1 and P2 in this first embodiment, the camera coordinate axes at P2 are aligned with the camera coordinate axes at P1 to a high degree of accuracy.

To determine the distance between A and B, my measurement technique first separately determines the location of each point in the coordinate system shown in FIG. 9. Once the locations of the points are known the desired distance is calculated from the Pythagorean theorem as:

$$r = \sqrt{(x_A - x_B)^2 + (y_A - y_B)^2 + (z_A - z_B)^2} \quad (1)$$

Considering now the determination of the location of either one of the points, the data processing begins by correcting the measured image position data for distortion. As I discuss further in the calibration section, I use the term distortion to refer to any deviation of the image position from the position that it would have if the camera were perfect. This is a much more general definition than is often used, where the term refers only to a particular type of optical field aberration.

Of course, this distortion correcting step is performed only if the distortion is large enough to affect the accuracy of the measurement, but this will be the case when using any standard borescope or almost any other type of camera to perform the measurement.

As is further described in the calibration section, one can write the image position coordinates as:

$$x_{im} = x'_{im} - f_{Dx}(x'_{im}, y'_{im})$$

$$y_{im} = y'_{im} - f_{Dy}(x'_{im}, y'_{im}) \quad (2)$$

where $(x'_{im}, y'_{im})$ are the experimental measurements and $(x_{im}, y_{im})$ are the distortion corrected versions. The same equation applies to the data at both camera positions, that is, both $x'_{im1}$ and $x'_{im2}$ are subjected to the same correction function $f_{Dx}$ and both $y'_{im1}$ and $y'_{im2}$ are corrected with $f_{Dy}$. The distortion correction functions $f_{Dx}$ and $f_{Dy}$ are determined in a calibration process which is described in the calibration section. This calibration process is known in the art.

Next, the data are scaled by the inverse of the effective focal length of the combined optical-video system. That is, the data $(x_{im1}, y_{im1}, x_{im2}, y_{im2})$ are multiplied by a factor necessary to generate the equivalent true values of the tangent of the viewing angles:

$$\tan(\alpha_{x1}) = -x_{im1}/i$$

$$\tan(\alpha_{y1}) = -y_{im1}/i \quad (3)$$

and likewise for the other two measurements for this point on the object from position P2. The equivalent focal length, i, is preferably determined in the same calibration process as is the distortion, as will be described later in the calibration section.

As the next step in the data processing, two data vectors, which I call the visual location vectors, are formed from the scaled, distortion corrected image position measurements. These data vectors are:

$$a_{v1} = \begin{bmatrix} \tan(\alpha_{z1}) \\ \tan(\alpha_{y1}) \\ 1 \end{bmatrix} \text{ and } a_{v2} = \begin{bmatrix} \tan(\alpha_{z2}) \\ \tan(\alpha_{y2}) \\ 1 \end{bmatrix} \quad (4)$$

A displacement vector is also formed by placing the perspective baseline (the measured distance between viewing positions P1 and P2) as the first element of a vector:

$$d_b = \begin{bmatrix} d \\ 0 \\ 0 \end{bmatrix} \quad (5)$$

I call vector $d_b$ the perspective displacement.

The perspective displacement is then transformed to the viewing coordinate system defined by the camera at P1 (that is, a coordinate system parallel to (x, y, z) defined above) by multiplication of $d_b$ by a pair of 3×3 rotation matrices $R_y$ and $R_z$:

$$d_{v1} = R_z R_y R_b \quad (6)$$

The multiplications in Equation (6) are standard matrix multiplications of, for instance, a 3×3 matrix with a 3×1 vector. Rotation matrices $R_y$ and $R_z$ describe the effects of a rotation of the coordinate system about the y axis and about the z axis respectively. They are each defined in a standard way as a function of a single rotation angle. The definitions of the rotation matrices, and the calibration process for determination of the rotation angles, is described later in the calibration and theory of operation sections. The alignment calibration process that I define there to determine these rotation angles is new.

The visual location vectors defined in Equation (4) are used to form two 3×2 data matrices:

$$C = [a_{v1} a_{v2}] \text{ and } D = [a_{v1} - a_{v2}] \quad (7)$$

The left pseudo-inverse of data matrix D is then calculated as:

$$D^{LI} = (D^T D)^{-1} D^T \quad (8)$$

where $D^T$ is the transpose of matrix D. Since the matrix product $D^T D$ is a 2×2 matrix, the inverse of that product can be calculated explicitly, as shown in the theory of operation. Thus, the software process outlined here for the measurement calculation requires nothing more sophisticated than straightforward additions, subtractions, multiplications, and divisions.

The location of the point being determined is then calculated as:

$$r_m = \begin{bmatrix} x \\ y \\ z \end{bmatrix} = \frac{1}{2} C D^{LI} d_{v1} = \frac{1}{2} [a_{v1} \; a_{v2}] [a_{v1} - a_{v2}]^{LI} d_{v1} \quad (9)$$

In the theory of operation, I show that Equation (9) is the least squares solution for the location of the point. The process ending with the calculation expressed in Equation (9) is performed for the data obtained on points A and B in turn, and then Equation (1) is used to calculate the desired distance between points A and B:

Measurement mode 2 is depicted in FIG. 10. Here there are up to a total of four viewing positions used. Point of interest A is viewed from positions P1A and P2A with perspective baseline $d_A$, while point B is viewed from P1B and P2B with perspective baseline $d_B$. The experimental data obtained during the mode 2 measurement process are the four image point coordinates for each of the points A and B, and the four viewpoint positions along the camera motion axis $l_{1A}$, $l_{2A}$, $l_{1B}$ and $l_{2B}$. Note that two of the viewing positions could be coincident, so that a total of three different viewing positions would be used, and this mode would still be distinct from mode 1.

Vectors $r_A$ and $r_B$ are determined using the perspective baselines $d_A = l_{2A} - l_{1A}$ and $d_B = l_{2B} - l_{1B}$ as has just been described for measurement mode 1. The distance between the coordinate origins for the measurements of A and B is then calculated as:

$$d_{AB} = \frac{1}{2}(l_{1A} + l_{2A} - l_{1B} - l_{2B}) \tag{10}$$

Next, vector $d_{AB}$ in the camera coordinate system is calculated as:

$$d_{AB} = R_z R_y \begin{bmatrix} d_{AB} \\ 0 \\ 0 \end{bmatrix} \tag{11}$$

Finally, the desired distance r is calculated as:

$$r = |r| = |d_{AB} + r_A - A - r_B| = \sqrt{r^T r} \tag{12}$$

where the vertical lines indicate the magnitude (length) of a vector.

It will be clear to a reader who studies the prior art that none of the prior art systems have the ability to measure the distance between points which cannot both be contained in a single camera view (my measurement mode 2). It may not be clear to that reader that the measurement process I have described as measurement mode 1 differs significantly from the processes taught by the related prior art. To help the reader understand the significance of my invention I now compare my measurement more closely to the prior art.

Figure 11:
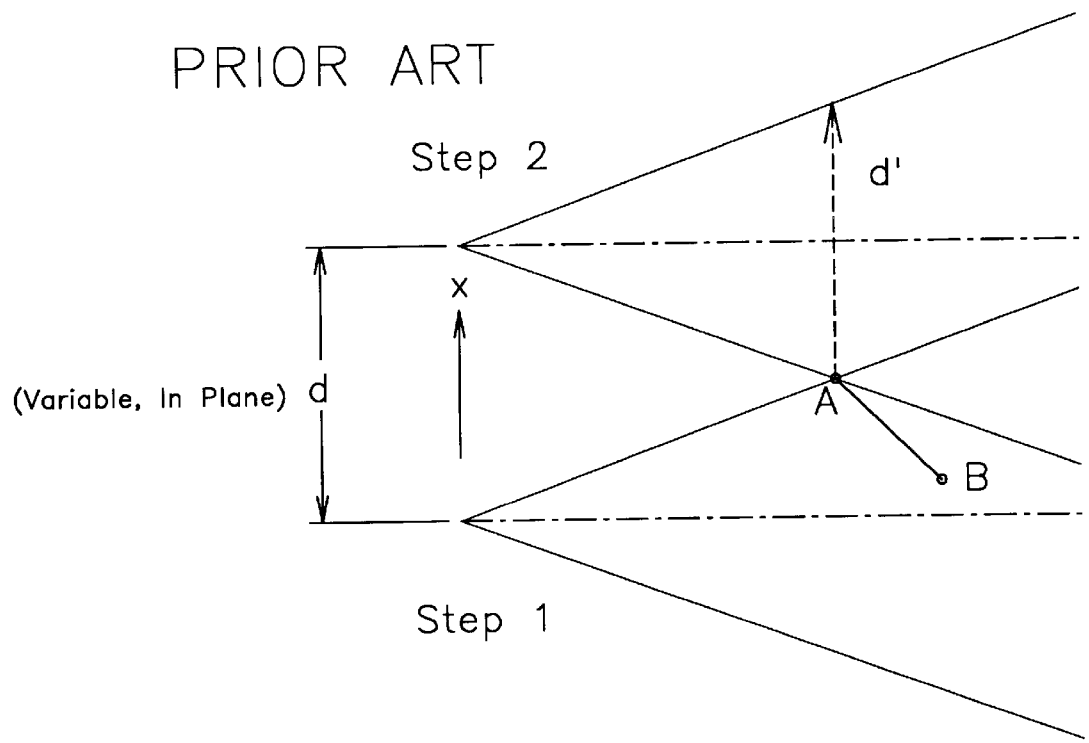
FIG. 11 depicts the first two steps of the dimensional measurement process taught in U.S. Pat. No. 4,207,594.
Figure 12:
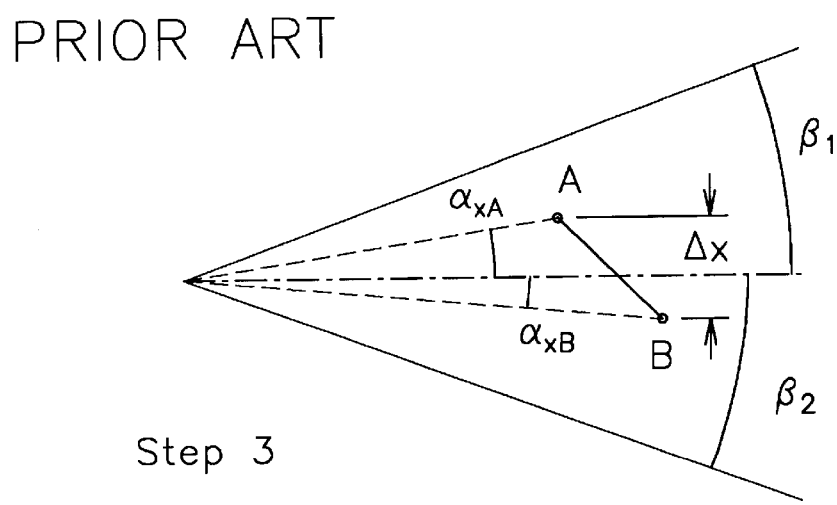
FIG. 12 depicts the third step of the dimensional measurement process taught in U.S. Pat. No. 4,207,594.

FIGS. 11 and 12 depict the measurement process taught by Morris and Grant in U.S. Pat. No. 4,207,594. Their measurement consists of a three-step process, the first two steps of which are depicted in FIG. 11. As in previous figures, two points of interest on the object are denoted by A and B. In the first step of the process, a selected one of the points is brought to one edge of the camera field of view by moving the camera along axis x. In the second step the same point on the object is brought to the other edge of the field of view by further advancing the camera along x. The distance d between the two positions of the camera is determined as part of this second step. This distance is considered equal to the linear size of the field of view at the object point, that is, d'=d.

The dimensional measurement step taught by Morris and Grant is depicted in FIG. 12. Here the relative angular sizes of the object and the field of view are determined. The measurement calculation is then:

$$\Delta x = \frac{d'(\tan(\alpha_{xA}) - \tan(\alpha_{xB}))}{\tan(\beta_1) - \tan(\beta_2)} \tag{13}$$

$$\Delta y = \frac{d'(\tan(\alpha_{yA}) - \tan(\alpha_{yB}))}{\tan(\beta_1) - \tan(\beta_2)}$$

where angles are defined to be positive if measured counter-clockwise from the optical axis and negative if measured clockwise from the optical axis. Equation (13) is expressed in terms of tangent of angles because it is the tangent which is proportional to position on the camera focal plane (in the absence of distortion).

It is important to realize that it is only the component of the distance between A and B projected on a plane perpendicular to the optical axis of the camera which can be determined by this technique. I have previously mentioned that the lack of correction for distortion means that even this projected distance will be in error.

Figure 13:
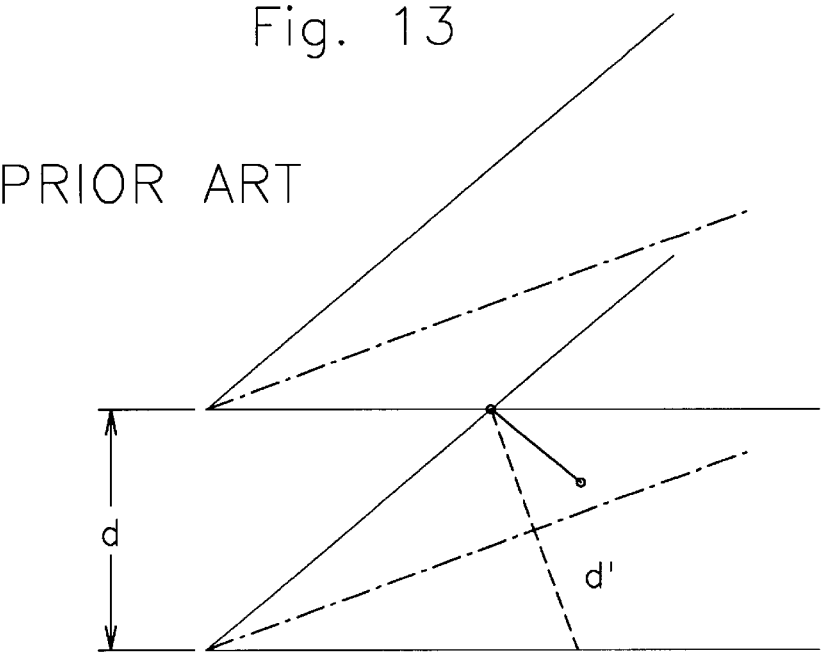
FIG. 13 shows a disadvantage of the measurement process taught in U.S. Pat. No. 4,207,594.

FIG. 13 shows an additional disadvantage of the technique of Morris and Grant. Here, the camera is not oriented with its optical axis perpendicular to the motion of the camera. In this case distance d is not equal to d' so that the size of the field of view at the object is not determined correctly. Thus this technique is restricted to the case where the optical axis of the camera is oriented perpendicular to the motion of the camera.

Figure 14:
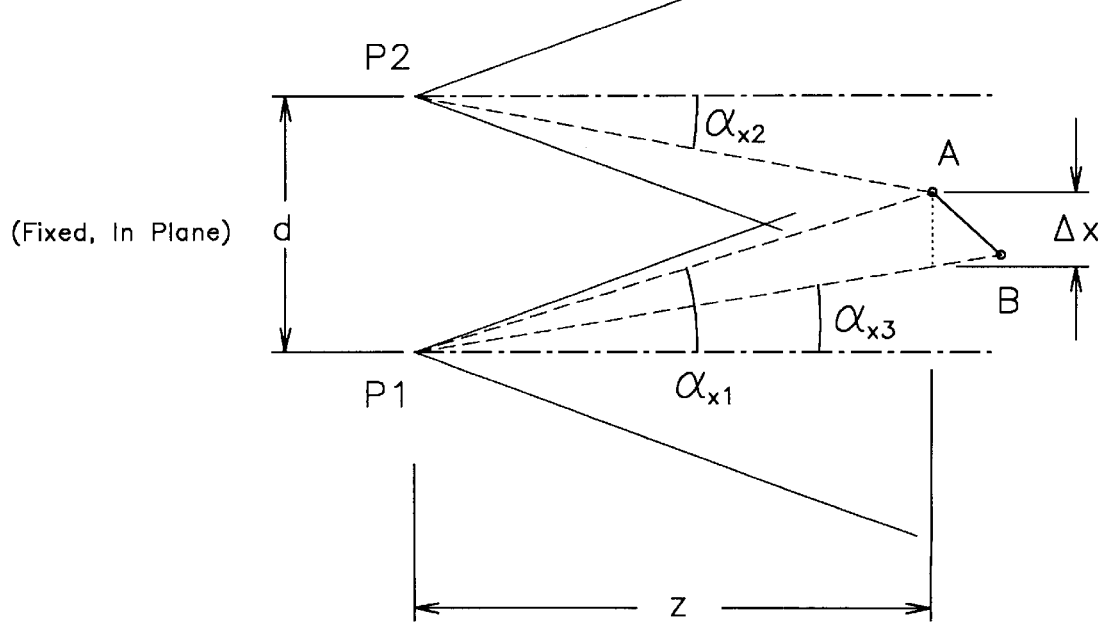
FIG. 14 depicts the dimensional measurement process taught in U.S. Pat. No. 4,702,229.

FIG. 14 depicts the measurement process taught by Zobel in U.S. Pat. No. 4,702,229 and used by Diener in U.S. Pat. No. 4,820,043. Here, the camera is moved a fixed distance between P1 and P2. However, only one point on the object is viewed from both positions of the camera. Although neither Zobel nor Diener give any measurement equations, it seems clear that what they mean to do is to determine the distance to the object point that was viewed from both P1 and P2. For the situation shown, this distance is:

$$z = \frac{d}{\tan(\alpha_{x1}) - \tan(\alpha_{x2})} \tag{14}$$

Given the distance, Zobel then makes object size measurements by:

$$\Delta x = z(\tan(\alpha_{x1}) - \tan(\alpha_{x3})) \tag{15}$$

There would be a similar equation for $\Delta y$, but Zobel shows only measurements being made along a single axis. Just as with Morris and Grant, Zobel determines only the projected components of the distance between the two points.

Figure 15:
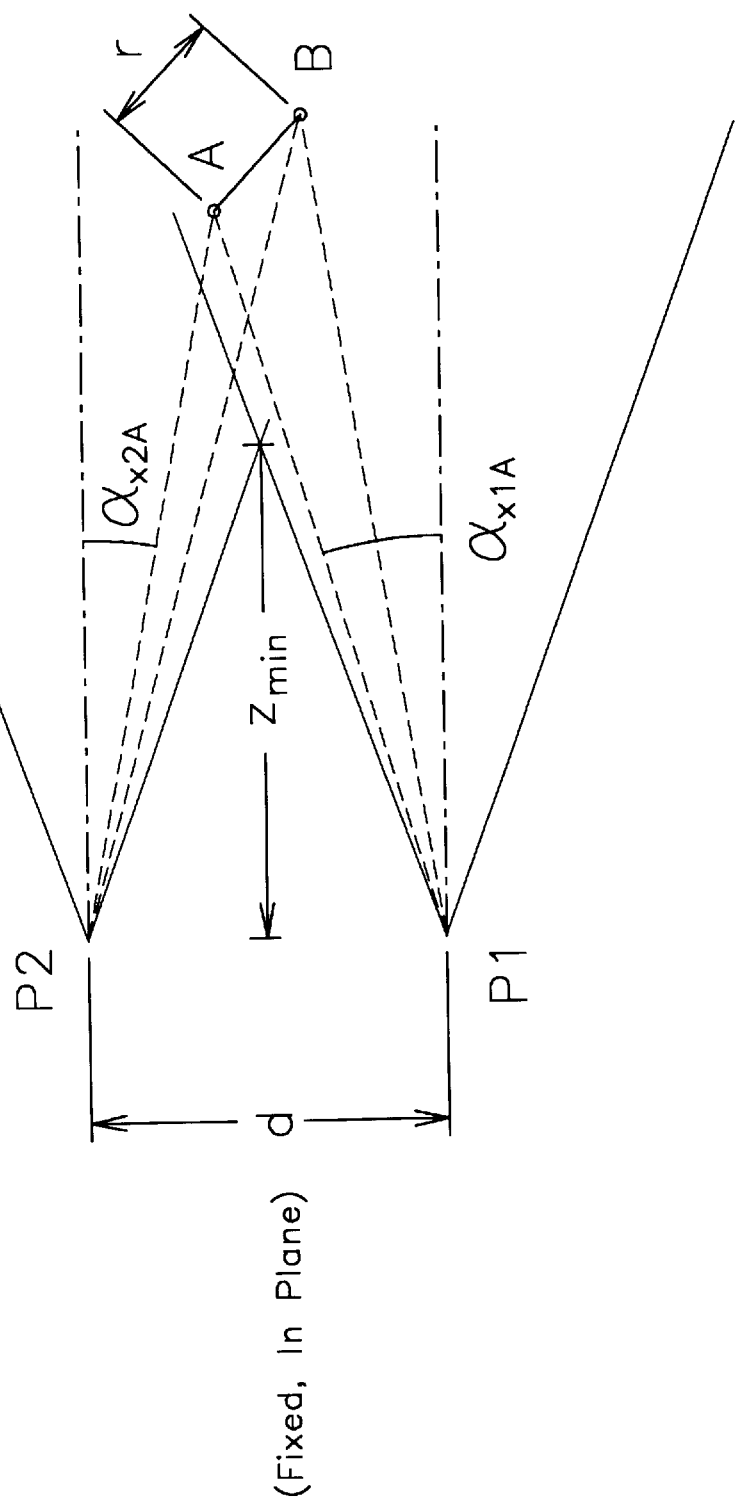
FIG. 15 depicts the dimensional measurement process taught in U.S. Pat. No. 4,935,810.

FIG. 15 depicts the measurement taught by Nonami and Sonobe in U.S. Pat. No. 4,935,810. Two cameras separated by a fixed distance d view both points A and B. Here both points A and B are measured at both positions P1 and P2, so that a perspective measurement of all three components of the object distance is made.

The teachings of Nonami and Sonobe will give accurate results only when both cameras are aligned perfectly perpendicular to the perspective baseline d, and when the x axes of the cameras are aligned perfectly along the perspective baseline (that is, d is constrained to lie in the plane of FIG. 15). In addition, the two cameras must be identical in distortion and effective focal length, and the distortion must be only a particular kind and amount of optical aberration.

Additionally, these inventors specifically teach that only three of the four available angular measurements should be used for each point location determination. Their measurement equations are:

$$x = \left(\frac{z}{2}\right)(\tan(\alpha_{x1}) + \tan(\alpha_{x2})) \qquad (16)$$

$$y = z\tan(\alpha_{y1})$$

$$z = \frac{d}{\tan(\alpha_{x1}) - \tan(\alpha_{x2})}$$

The three dimensional location of each of the points A and B are determined according to Equations (16) and then the distance between the points is calculated with Equation (1).

As I show in the error analysis, with the fixed perspective baseline taught by Nonami and Sonobe, the error in the distance measurement due to error in the determination of the angles is proportional to the square of the distance z. An additional disadvantage is that with the fixed perspective baseline, there is a minimum distance for which measurements can be made, shown as $z_{min}$ in FIG. 15.

In my measurement system, I teach how to make the measurement for any arbitrary camera alignment with respect to the displacement between viewing positions P1 and P2. This arbitrary camera alignment has two components. As was shown in FIG. 9, one component of misalignment is that the camera optical axis need not be oriented perpendicular to the motion of the camera.

The second component of arbitrary camera misalignment is the orientation of the perspective displacement with respect to the camera x axis. In FIG. 9, this is expressed as the perspective displacement not being constrained to lie in the plane of the Figure.

The physical source of this second misalignment can be understood by examining FIG. 1. In FIG. 1, video camera back 134 must have a specific rotational orientation with respect to borescope field of view 122 in order for the camera x axis to be aligned with the perspective displacement. But, the rotational alignment of video camera back 134 with respect to field of view 122 is not something that is controlled or even monitored in a standard video borescope.

For both of these reasons, it is only my measurement system, with its ability to use an arbitrary camera alignment in the perspective measurement, that can make the measurement with a standard, off the shelf, video borescope.

Now, as I will explain later in the error analysis, in order to achieve the most precise measurements possible, the user should prepare the borescope before making measurements by rotating video camera back 134 about the axis of borescope 120 so that the horizontal video direction of camera back 134 is approximately aligned to the plane in which the optical axis of field of view 122 lies. (This assumes that there is no additional rotation of the image about the optical axis inside the borescope). In order to obtain the error reducing properties of this alignment, it is not necessary that it be very accurate. Thus, this preparatory alignment is not a formal part of the measurement procedure, or of the calibration of the borescope. In any case, my calibration procedure determines the precise level of misalignment, and my data processing procedures take it into account in the measurement.

In addition, as I show in the error analysis, with my variable perspective baseline, d, the measurement error is proportional to the distance, z, rather than to the square of the distance in the case of Nonami and Sonobe. This very significant reduction in the error is shown graphically for a particular case in FIG. 52.

Figure 52:
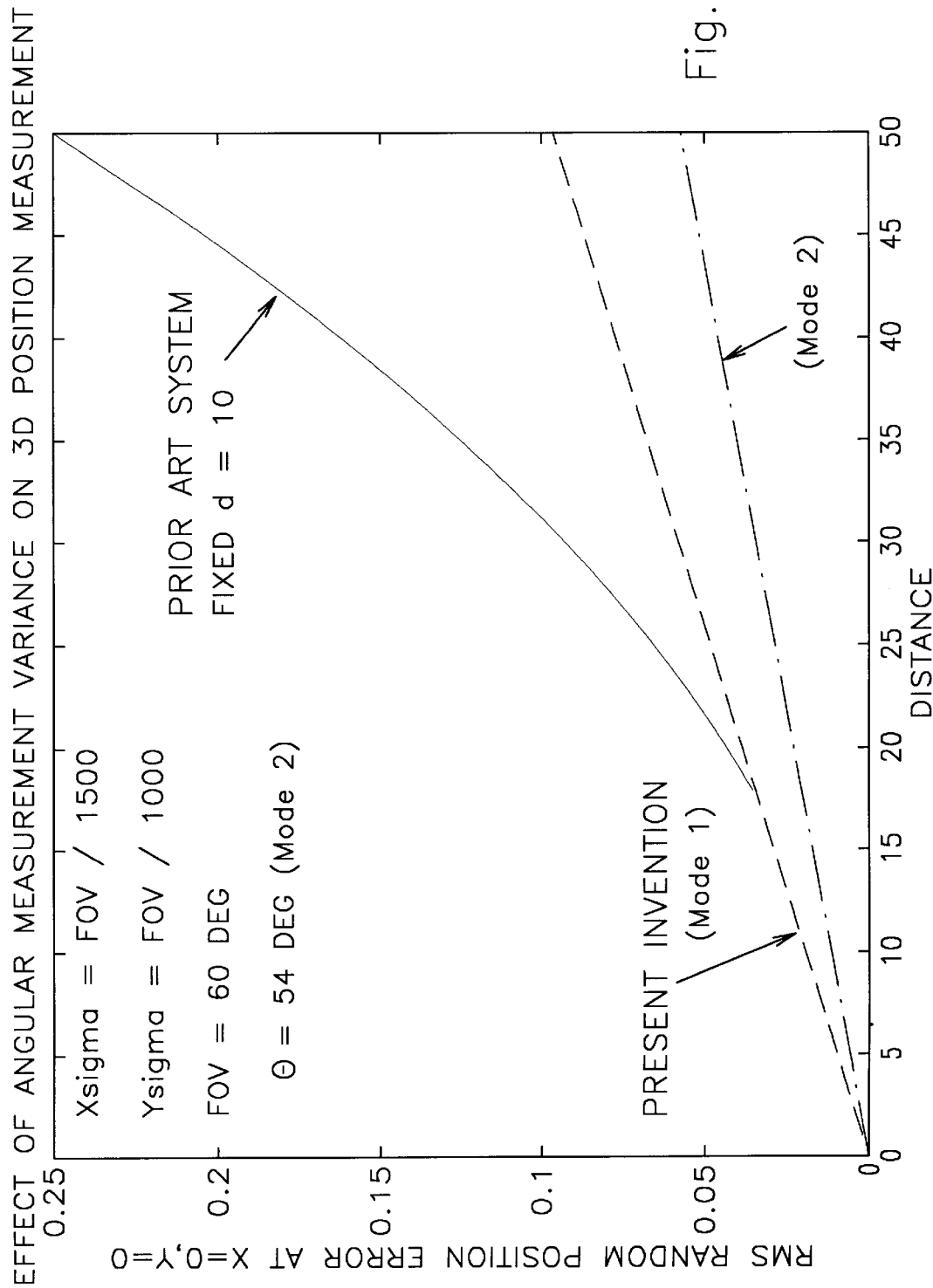
FIG. 52 shows a comparison of the RMS position error made with my invention to the same error made with a fixed perspective baseline system, under similar conditions.

In FIG. 52, fixed and variable baseline systems are compared on an equal footing, as explained below in the sub-section entitled "The random error in variable and fixed baseline linear camera motion systems". In the Figure, the performance of a fixed baseline system with d=10 is shown as a solid line. This line begins at a distance of 17, because that is the minimum measurement distance with the assumed parameters. The two measurement modes that I teach have no minimum measurement distance, and the error is much reduced as compared to the fixed baseline system.

As I will explain in the error analysis, measurement mode 2 can have a lower error than does measurement mode 1 because the points of interest can be brought to an optimum apparent angular position in each of the views, whereas the apparent angular positions chosen for the points in measurement mode 1 is necessarily a compromise. Of course, it is clear from FIG. 52 that it is much more important that the perspective baseline be variable (compare my mode 1 performance to the prior art) than it is that the perspective baseline be chosen to be exactly the optimum value (compare the performance of mode 1 to mode 2).

As another distinction between my system and the prior art, I teach that it is important not to throw away the second angular measurement in y, so that my measurement Equations (9), expressed for the same restricted system geometry as specified by Nonami and Sonobe, reduce to (compare to Equation (16)):

$$x = \left(\frac{z}{2}\right)(\tan(\alpha_{x1}) + \tan(\alpha_{x2})) \qquad (17)$$

$$y = \left(\frac{z}{2}\right)(\tan(\alpha_{y1}) + \tan(\alpha_{y2}))$$

$$z = \frac{d}{\tan(\alpha_{x1}) - \tan(\alpha_{x2})}$$

DESCRIPTION OF A SECOND EMBODIMENT

Figure 16:
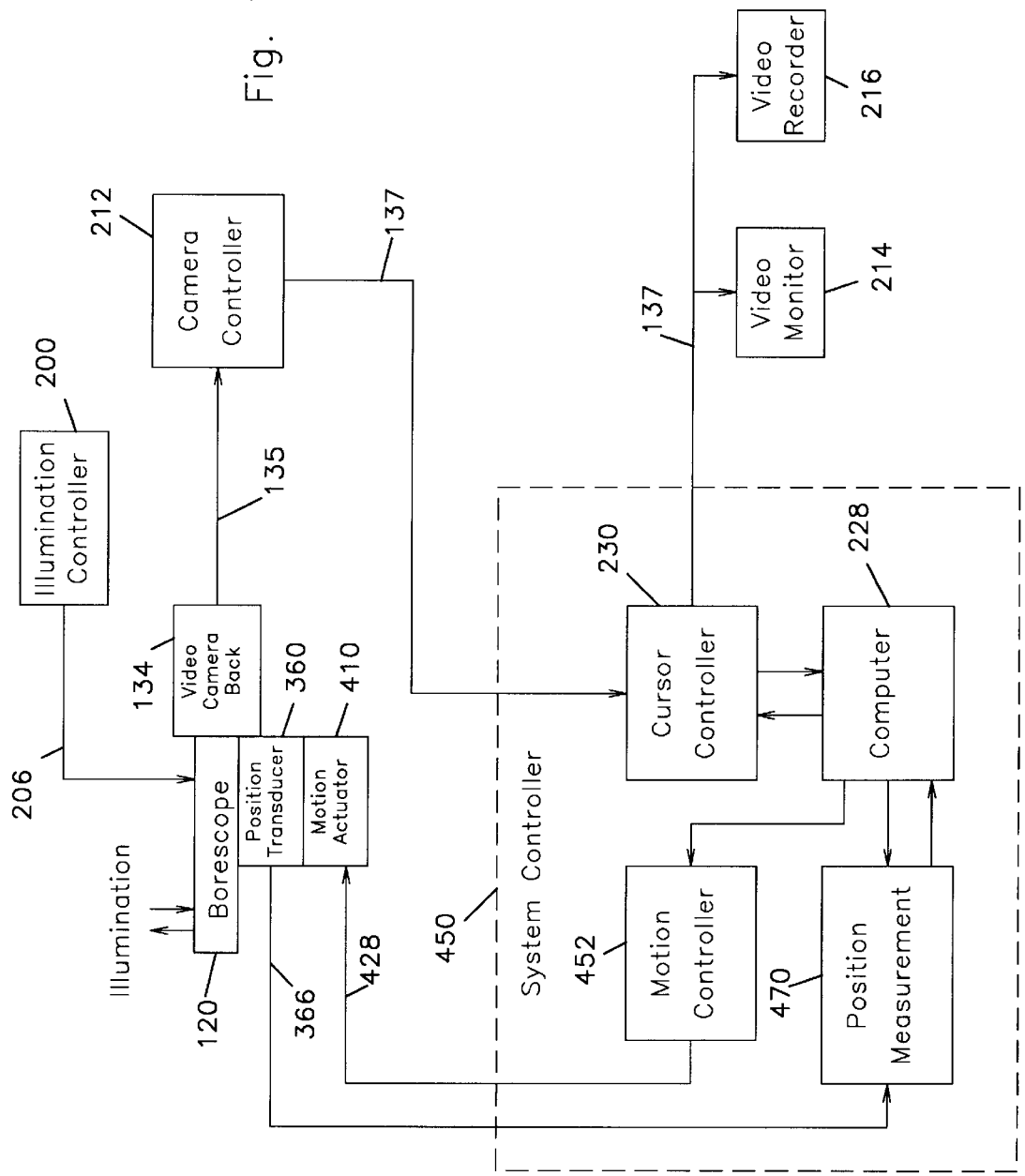
FIG. 16 is a block diagram of the electronics of a second embodiment of the invention.

FIG. 16 shows a block diagram of the electronic portion of a second embodiment of my invention. The new elements added as compared to the first embodiment are a position transducer 360, a motion actuator 410, a motion controller 452 and a position measurement block 470. The latter two blocks are combined with cursor controller 230 and computer 228 into a block called the system controller 450. Position transducer 360 is connected to position measurement block 470 by a position transducer cable 366. Motion actuator 410 is connected to motion controller 452 with an actuator cable assembly 428.

This second embodiment of the electronics could be built with the capability of completely automatic operation of the position of borescope 120. That is, borescope 120 could be positioned anywhere within the range of travel of translation stage 180 (FIG. 2) under control of computer 228 upon operator command. In this case, the user would only have to command some initial position for translation stage 180, then align and clamp borescope 120 appropriately as described above for the operation of the first embodiment, and then never have to touch any of the mechanical hardware again during the measurement process. The two viewing positions, P1 and P2, as described previously, would be selected by the user by moving stage 180 under computer control.

Such automatic positioning of borescope 120 could be closed-loop positioning. That is, the computer would position the borescope by moving the borescope until a particular desired position was indicated by the combination of transducer 360 and position measurement block 470.

In fact, the same commercial vendors who supply translation stages often supply complete positioning systems which combine a translation stage with the motion control and position measurement blocks shown in FIG. 16. Most often these systems use an actuator comprising an electric motor, either a dc motor or a stepping motor, driving a precision lead screw. That is, the actuator is essentially a motorized micrometer. Clearly, there are a number of different actuators and position transducers that can be used in any such system.

What I consider the best mode for implementing this second embodiment of the invention is somewhat different than the system I have just described. I believe that a system can be built at lower cost and be at least as convenient to operate if it is built as I will now describe. Since the primary use of the mechanical subsystem is to move borescope 120 (FIG. 1) back and forth between two positions, this embodiment is directed toward making that process simple and quick. Generally speaking, it takes a long time for a motor driven translation stage to move between positions spaced a significant distance apart.

Figure 19:
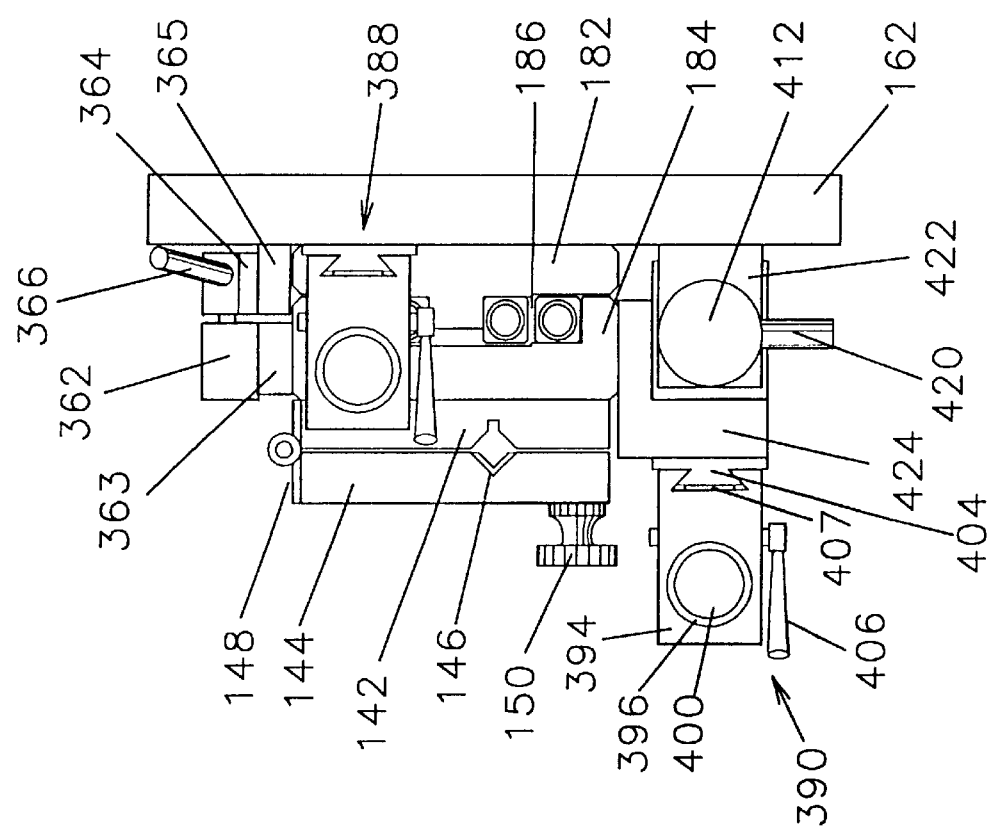
FIG. 19 is a rear view of the mechanical portion of a second embodiment of the invention.
Figure 17:
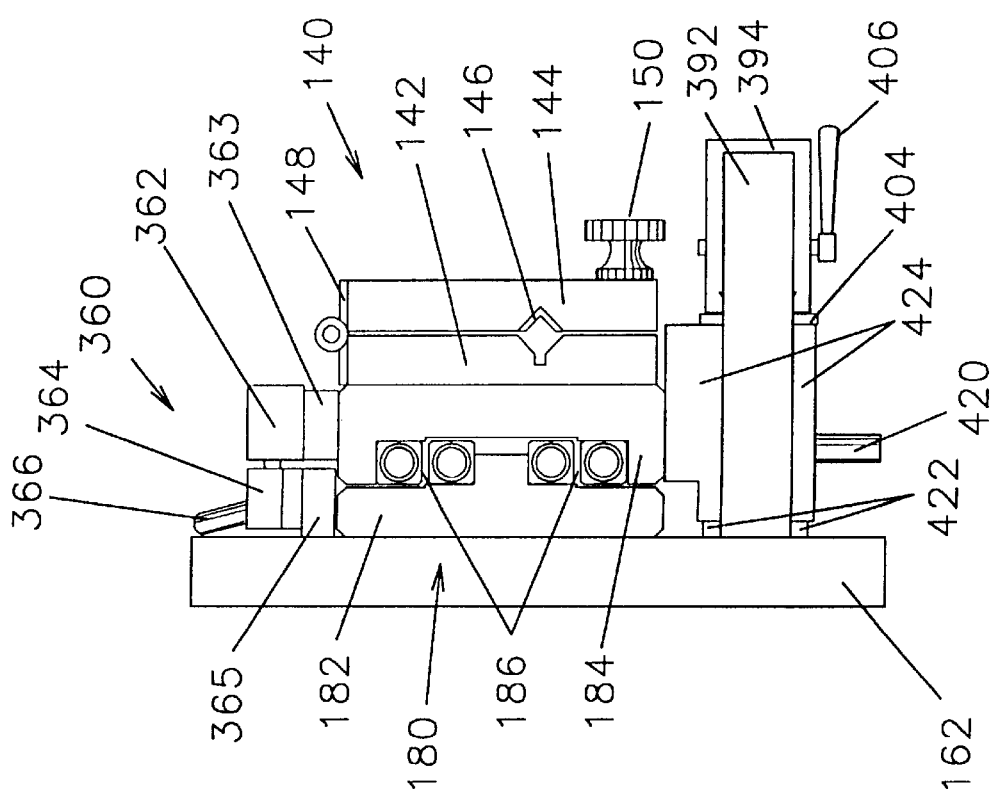
FIG. 17 is a front view of the mechanical portion of a second embodiment of the invention.
Figure 18:
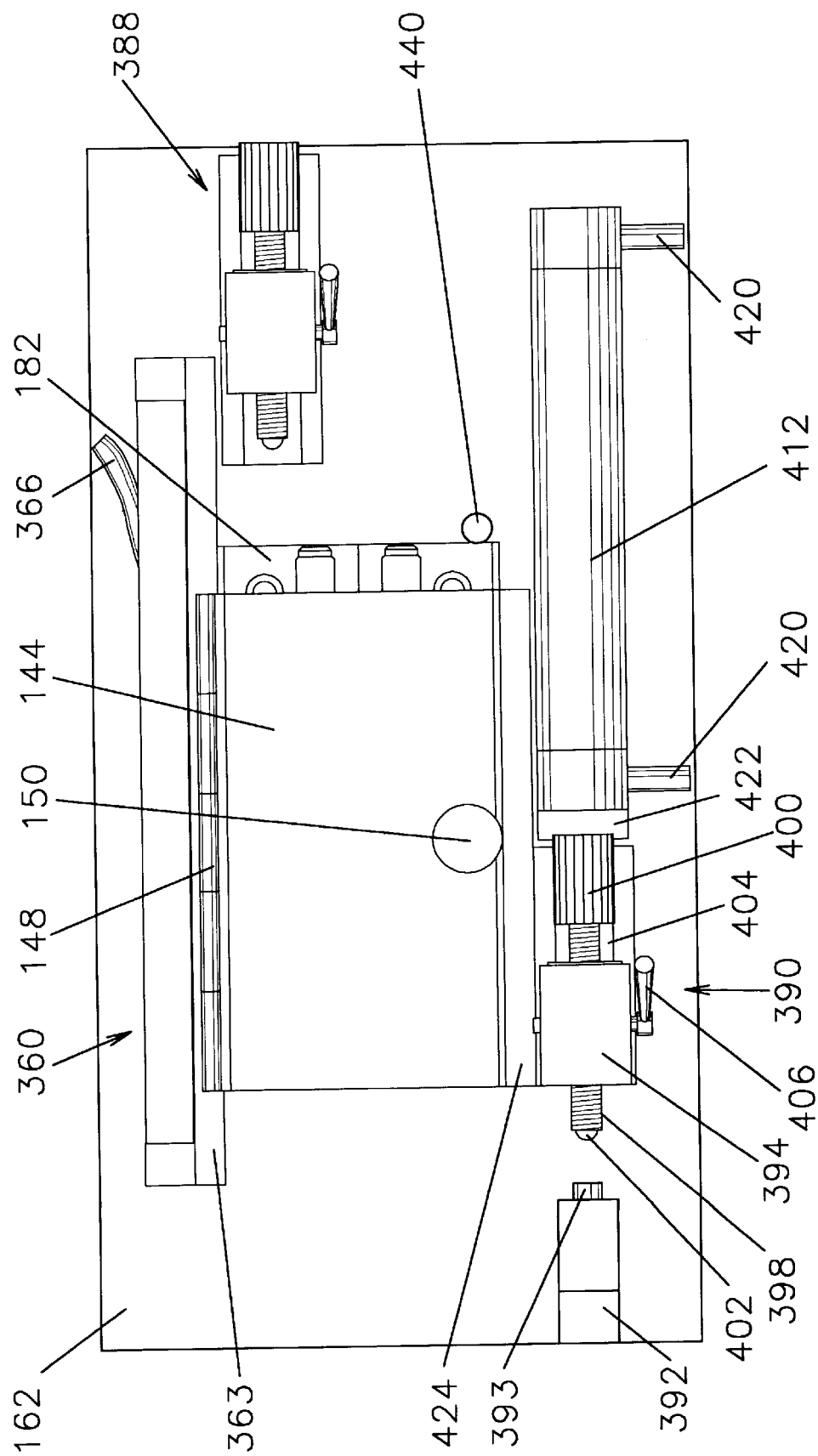
FIG. 18 is a plan view of the mechanical portion of a second embodiment of the invention.
Figure 21:
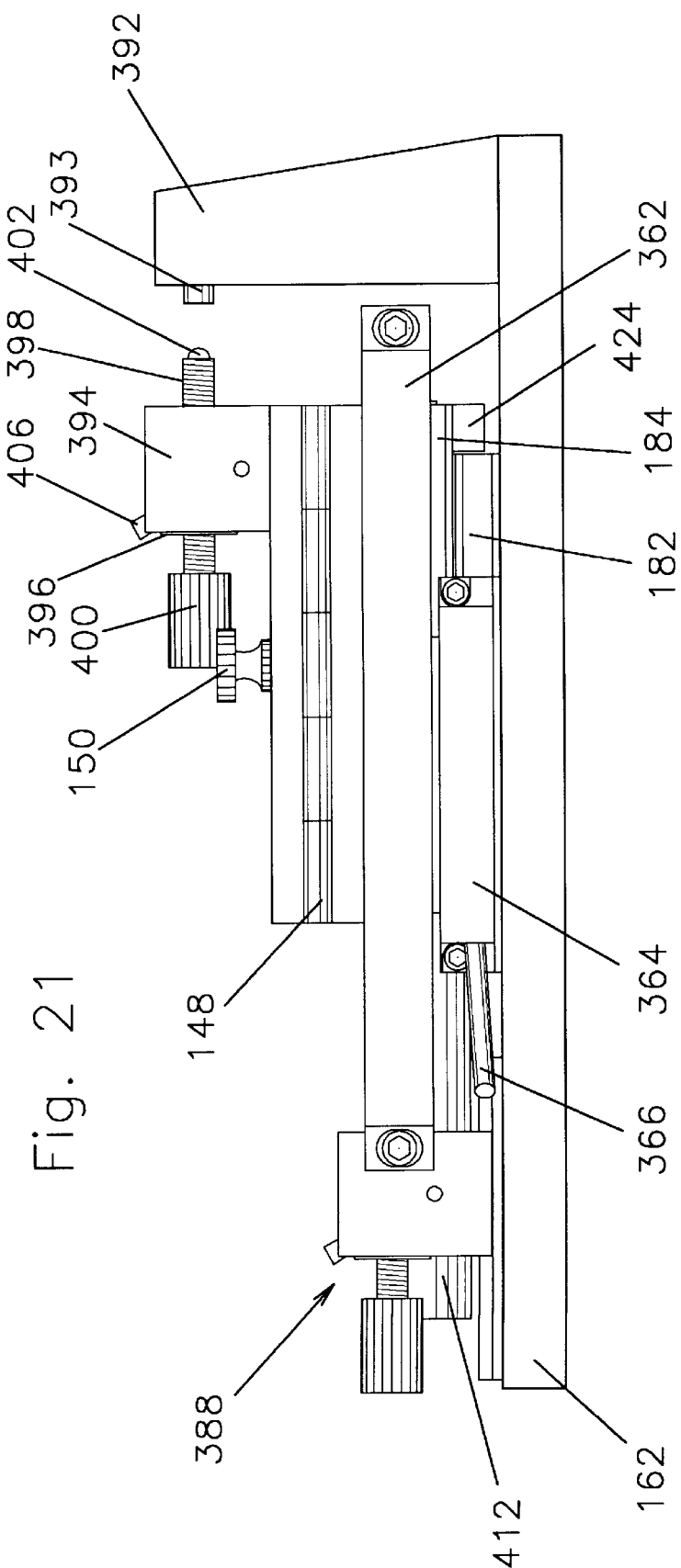
FIG. 21 is a right side elevation view of the mechanical portion of a second embodiment of the invention.

The second embodiment of BPA 138 is shown in FIGS. 17 through 21. FIG. 17 is a front view, FIG. 18 is a top view, FIG. 19 is a rear view, while FIGS. 20 and 21 are left and right side views respectively.

The same borescope clamp assembly 140 as was used in the first embodiment is also used in this second embodiment. As before, lens tube 124 has been removed from clamp 140 in these views for clarity. Clamp 140 is comprised of a lower V-block 142, an upper V-block 144, a hinge 148, and a clamping screw 150. The upper V-block is lined with a layer of resilient material 146, for the same reason given in the description of the first embodiment.

Also, just as in the first embodiment, lower V-block 142 is attached to the moving table 184 of a translation stage or slide table 180. The translation stage consists of a moving table 184 and a fixed base 182, connected by crossed roller bearing slides 186. Fixed base 182 is attached to a BPA baseplate 162.

The differences between this second embodiment of BPA 138 and the first embodiment are contained in the methods by which moving table 184 is positioned and how its position is determined. In this second embodiment an air cylinder 412 is mounted to an actuator mounting bracket 422 which is in turn mounted to baseplate 162. Air cylinder 412, which is shown best in FIG. 20, has two air ports 420 and an extension rod 418. Air hoses (not shown) are connected to ports 420 and are contained within actuator cable assembly 428 which was shown on the block diagram, FIG. 16. The air hoses convey air pressure from motion controller 452 (FIG. 16). Extension rod 418 is connected to an actuator attachment bracket 424 through an actuator attachment bushing 426. Bracket 424 is fastened to moving table 184 as is best shown in FIGS. 18 and 19.

On the other side of the moving table/borescope clamp assembly from air cylinder 412 is mounted a linear position transducer 360. Position transducer 360 consists of a linear scale body 362 and a scale read head 364, which are attached to each other as an integral assembly, but which are free to move with respect to one another within limits along one direction. Attached to read head 364 is a position transducer cable 366 which connects to system controller 450 as was shown in FIG. 16. Scale body 362 is mounted to moving table 184 through a scale body mounting bracket 363. Read head 364 is mounted to BPA baseplate 162 through a read head mounting bracket 365.

Attached to the upper side of actuator attachment bracket 424 is a dovetail slide 404. Mounted on dovetail slide 404, as best shown in FIGS. 18 and 20, is an adjusting nut bracket 394. Bracket 394 contains a fixed nut 396 which in turn contains an adjusting screw 398. Adjusting screw 398 has an adjusting screw knob 400 and an adjusting screw tip 402 disposed at opposite ends of its length. Bracket 394 also contains a bracket position locking handle 406. Locking handle 406 is connected to a locking cam 407 mounted inside bracket 394. Locking cam 407 is shown only in FIG. 19.

Dovetail slide 404 and adjusting nut bracket 394 and the items contained therein form a subassembly known as the forward stop positioner 390. An exactly similar assembly called the rearward stop positioner 388 is mounted to the BPA baseplate behind translation stage fixed base 182. Rearward stop positioner 388 is best shown in FIGS. 18, 19 and 21.

Depending on the position of moving table 184, adjusting screw tip 402 of adjusting screw 398 of forward stop positioner 390 can contact end stop insert 393 of end stop 392 as best shown in FIGS. 18 and 20. Similarly, the rearward stop positioner 388 is aligned so that the tip of its adjusting screw can contact the rear end of moving table 184, as can be best visualized from FIGS. 18 and 19.

In FIG. 18 is shown a stop pin hole 440, the purpose of which will be explained below.

Although the overall length of BPA 138 could be made shorter if read head 364 were mounted to moving table 184 and scale body 362 were mounted to baseplate 162, I have chosen to mount the unit as shown because then cable 366 does not move with table 184. Either way will work, of course.

Operation of the Second Embodiment

As stated above, the differences between this second embodiment and the first embodiment relate to how the borescope is moved and how the position of the borescope is determined.

The inclusion of position transducer 360 and position measurement block 470 as shown in FIG. 16 means that the user of the instrument is no longer responsible for making position readings and transcribing them into computer 228. When the user indicates that the cursors are positioned as desired, as was described in the operation of the first embodiment, the computer will now automatically command a camera position measurement from position measurement block 470 and will automatically store this datum.

Note that position transducer 360 need not be an absolute encoder of position. From Equation (10) (and the similar expression for measurement mode 1, which is not a display equation) it is clear that the measurement depends only on the distance moved between viewing positions. A constant value can be added to the encoded position without changing the measurement in any way. Thus, position transducer 360 together with position measurement block 470 need only produce a position value that has an offset which is constant over the period of a measurement. This offset need not be the same from measurement to measurement. This means that transducer 360 can be what is called an incremental distance encoder, and this is what will be described.

As I will explain later, if one wants to correct for errors in the camera motion, or if one wants to use a camera motion that is not constrained to a perfect straight line, then it is necessary to know the absolute position of the camera with respect to some fixed reference point. The distance encoder that I describe here has what is known as a "home" position capability. The home position allows one to use the incremental encoder as an absolute encoder when and if required.

Position transducer 360 contains a precision magnetic or optical pattern formed on a plate inside scale body 362. Read head 364 reads the pattern and thereby produces signals which change according to changes in relative position between read head 364 and scale body 362. The unit depicted here is sold by RSF Electronics of Rancho Cordova, Calif., but similar units are available from Renishaw and Heidenhain. The unit shown is available in resolutions as small as 0.5 micron, with guaranteed positioning accuracy as good as ±2 microns over a length of 1 foot. For the short length unit used in the BPA, one would expect the accuracy to be considerably better.

Position measurement block 470 interprets the signals from read head 364 to determine changes in the position of read head 364 with respect to the scale inside scale body 362. Position measurement block 470 formats the position data into a form that is understood by computer 228. If the home position capability has not been used, then measurement block 470 will report a position relative to the position that the transducer assembly was in when the power was turned on. If the home capability has been used, then the position will be reported relative to the fixed home position. Whether the home position capability is used or not is a design decision which depends on whether motion errors are to be corrected. The method of correction for errors in the motion is discussed at length below in a sub-section entitled "Operation of Embodiments Using Arbitrary Camera Motion".

The existence of motion actuator 410 and motion controller 452 means that the user is not required to manually move the borescope between P1 to P2. This has the advantage of eliminating any chance that the user will accidentally misalign BPA 138, hence borescope 120, during the measurement process. It also has the advantage of eliminating the tedious rotation of the micrometer barrel 178 which is required during operation of the first embodiment.

Air cylinder 412 is a double action unit, which means that air pressure applied to one of the ports 420 will extend rod 418 while air pressure applied to the other port will retract rod 418. When a differential pressure is applied between the ports, rod 418 will move until it is stopped by some mechanical means. If there is no other mechanical stop, rod 418 simply moves to either its fully extended or fully retracted position.

Through the action of bushing 426 and attachment bracket 424, moving table 184 is constrained to move with extension rod 418. The extent of motion of table 184 is controlled by the mechanical stops created by the combination of forward stop positioner 390 and end stop 392 and the combination of rearward stop positioner 388 and the rear end of moving table 184. For instance, in the forward motion direction, the limit to the motion of table 184 is determined when adjusting screw tip 402 of adjusting screw 398 contacts insert 393 of end stop 392. Since the limit positions of table 184 are determined by these mechanical stops, backlash in bushing 426 does not affect the accuracy or repeatability of this positioning. Thus, viewing positions P1 and P2 are solely determined by the position of these mechanical limit stops. The measurement of these positions, however, is subject to any backlash contained within position transducer 360, or within the attachments of the transducer to the remainder of the structure.

Considering now the forward stop positioner 390, operating handle 406 rotates cam 407 to either produce or remove a locking force due to contact between cam 407 and dovetail slide 404. Thus, when unlocked, bracket 394 can be slid back and forth along dovetail slide 404 until adjusting screw tip 402 is located to give the desired stop position. Handle 406 is then rotated to force cam 407 against slide 404 to lock bracket 394 in place. Adjusting screw 398 can then be rotated in fixed nut 396 with handle 400 to produce a fine adjustment of the stop position.

Once the positions of adjusting screws 398 of forward stop positioner 390 and rearward stop positioner 388 are set as appropriate for the desired perspective viewing positions P1 and P2, moving back and forth between these positions is a simple matter of reversing the differential pressure across air cylinder 412. Depending on the length of the air hoses which connect cylinder 412 to motion controller 452, the characteristics of air cylinder 412, and the mass of the assembly being supported by moving table 184, it may be necessary to connect a motion damper or shock absorber (not shown) between moving table 184 and BPA baseplate 162. This would be required if it is not possible to control the air pressure change to produce a smooth motion of table 184 between the stops at P1 and P2.

Stop pin hole 440 is used as follows. At the beginning of the measurement process, it makes sense to start with moving table 184 centered in its range of travel. Therefore, a stop pin (not shown) is inserted into hole 440 and computer 228 is instructed to cause motion controller 452 to apply air pressure to cylinder 412 to produce an actuation force which will cause moving table 184 to move backwards until it is stopped by the stop pin. At this point the user is ready to begin the measurement set up process.

If the home positioning capability of transducer 360 is to be used, after the instrument is powered up, but before measurements are attempted, computer 228 is instructed by the user to find the home position. Computer 228 then commands motion controller 452 to move actuator 410 back and forth over its full range of motion. Computer 228 also commands position measurement block 470 to simultaneously look for the home position signature in the output signal from transducer 360. Once the home position is found, the offset of the position output data from position measurement block 470 is set so that a predetermined value corresponds to the fixed home position.

In detail, the process of making a measurement of the distance between two points, both of which are contained within a relatively small portion of apparent field of view 312 as shown in FIGS. 5 and 6, (that is, measurement mode 1) is made up of the following steps in this second embodiment:

1. Translation stage 180 is centered in its range of travel by use of a stop pin as described above.
2. A specific area of interest on object image 314 is located in apparent field of view 312 by sliding and rotating borescope 120 inside borescope clamp 140.
3. Borescope clamp 140 is locked with clamping screw 150 to secure the position and orientation of the borescope with respect to BPA 138.
4. Computer 228 is instructed to remove any differential air pressure across air cylinder 412. The stop pin is removed from hole 440. Moving table 184 is now free to move. The user moves table 184 rearward until the view on video screen 310 is approximately as shown in either FIG. 5 or FIG. 6.
5. Rearward stop positioner 388 is positioned so that the adjusting screw tip contacts the rear end surface of moving table 184. Stop positioner 388 is then locked at this position.
6. The user moves table 184 forward until the view on video screen 310 is approximately as shown in the opposite view of FIGS. 5 and 6. That is, if in step 4, the view in FIG. 6 was attained, then in this step, the view in FIG. 5 is to be obtained.

7. Forward stop positioner 390 is adjusted so that the adjusting screw tip contacts end stop insert 393, and is then locked into position.

8. The computer is instructed to apply air pressure to move table 184 rearward. The view on video screen 310 is inspected and any fine adjustments to the position of the borescope are made by rotating the adjustment screw of rear stop positioner 388. This is position P2.

9. The computer is instructed to apply air pressure to move table 184 forward. The view on video screen 310 is inspected and any fine adjustments to the position of the borescope are made by rotating the adjustment screw of forward stop positioner 390. This is position P1.

10. Cursors 316 and 318 are then aligned with the selected points on object image 314 using the user interface provided by computer 228.

11. When each cursor is aligned correctly, computer 228 is commanded to store the cursor positions. The cursors can be aligned and the positions stored either sequentially, or simultaneously, at the option of the user.

12. Computer 228 automatically commands a position reading from position measurement block 470. Computer 228 records this position reading as the position of P1.

13. Computer 228 is instructed to apply air pressure to cylinder 412 to move table 184 rearward. Steps 10 to 12 are repeated for P2.

14. The user commands the computer to calculate and display the true three-dimensional distance between the points selected by the cursors in steps 10 and 13. If desired, the computer can be commanded to also display the absolute positions of each of the two points in the coordinate system that was defined in t he operation of the first embodiment.

In detail, the process of making a measurement of the distance between two points, when they cannot both be contained within a relatively small portion of the apparent field of view 312 as shown in FIGS. 7 and 8 (that is, measurement mode 2), is made up of the following steps:

1. Computer 228 is instructed to command cursor controller 230 to produce a single cursor. While it is not absolutely necessary to use a single cursor, I believe that the use of a single cursor helps to avoid unnecessary confusion on the part of the user.

2. Translation stage 180 is centered in its range of travel by use of a stop pin as described above.

3. A specific area of interest on object image 314 is located in apparent field of view 312 by sliding and rotating borescope 120 inside borescope clamp 140. The two points of interest are identified, and the borescope is positioned so that the center of apparent field of view 312 is located approximately equidistant between the two points of interest.

4. Borescope clamp 140 is locked with clamping screw 150 to secure the position and orientation of the borescope with respect to BPA 138.

5. Computer 228 is instructed to remove any differential air pressure across air cylinder 412. The stop pin is removed from hole 440. Moving table 184 is now free to move. The user moves table 184 rearward until the view on video screen 310 is approximately as shown in one of the views of either FIG. 7 or FIG. 8. The first view is selected so that the first point of interest is located substantially on one side of apparent field of view 312.

6. The user moves table 184 forward to obtain a second view of the first point of interest. The second view is selected so that the point of interest is located substantially on the other side of apparent field of view 312 from where it was in the first view. This step insures that a suitable view is, in fact, obtainable within the range of motion of table 184, and that, for instance, the view is not blocked by intervening objects.

7. Steps 5 and 6 are repeated for the second point of interest. This step ensures that suitable views are, in fact, obtainable for the second point of interest with the borescope alignment chosen in step 3.

8. The user moves table back to the first view of the first point of interest chosen in step 5.

9. Rearward stop positioner 388 is positioned so that the adjusting screw tip contacts the rear end surface of moving table 184. S top positioner 388 is then locked at this position.

10. The user moves table back to the second view of the first point of interest chosen in step 6.

11. Forward stop positioner 390 is positioned so that the adjusting screw tip contacts end stop insert 393, and is then locked into position.

12. The computer is instructed to apply air pressure to move table 184 rearward. The view on video screen 310 is inspected and any fine adjustments to the position of the borescope are made by rotating the adjustment screw of rear stop positioner 388. This is position P2 for the first point of interest.

13. The computer is instructed to apply air pressure to move table 184 forward. The view on video screen 310 is inspected and any fine adjustments to the position of the borescope are made by rotating the adjustment screw of forward stop positioner 390. This is position P1 for the first point of interest.

14. The cursor is then aligned with the first point of interest on object image 314 using the user interface provided by computer 228.

15. When the cursor is aligned correctly, computer 228 is commanded to store the cursor position.

16. Computer 228 automatically commands a position reading from position measurement block 470. Computer 228 records the position reading as the position of P1.

17. Computer 228 is instructed to apply air pressure to cylinder 412 to move table 184 rearward. Steps 14 to 16 are repeated. Computer stores the borescope and cursor position data.

18. The user turns off air pressure and repeats steps 8 to 17 for the second point of interest, which was identified in step 7.

19. The user commands the computer to calculate and display the true three-dimensional distance between the points. If desired, the computer can be commanded to also display the absolute positions of each of the two points in the coordinate system that was defined in the operation of the first embodiment.

In this second embodiment, the data acquired and the processing of that data are identical to that described for the first embodiment. If motion errors are to be corrected, the data processing is slightly more involved, and will be discussed below in the section entitled "Operation of Embodiments Using Arbitrary Camera Motion".

DESCRIPTION OF A THIRD EMBODIMENT

The mechanical portion of a third embodiment of my invention is shown in an overall perspective view in FIG. 22 and in detailed views in FIGS. 23 through 29. This embodiment implements a new type of rigid borescope which I call an electronic measurement borescope (EMB). FIG. 30 is an electronic functional block diagram of the EMB system.

In FIG. 22 electronic measurement borescope 500 has a borescope probe tube 512 which itself contains an elongated viewing port 518 at the distal end. At the proximal end of probe tube 512 is located a fiber optic connector 128. Tube 512 is attached to a proximal housing 510, to which is mounted an electronic connector 502. An electronic cable (not shown) connects EMB 500 to a system controller 450 as shown in FIG. 30.

FIGS. 23, 24, and 25 are respectively a plan view and left and right side elevation views of the distal end of electronic measurement borescope 500. In these three views borescope probe tube 512 has been sectioned to allow viewing of the internal components.

In FIGS. 23 through 25 a miniature video camera 224 is shown mounted to a moving table 184 of a translation stage 180. Camera 224 is made up of a solid state imager 220 and an objective lens 121. Prism 123 redirects the field of view of camera 224 to the side so that the angle between the optical axis of the camera and the translation direction is approximately 90 degrees, or some other substantially side-looking angle as required for the desired application. Solid state imager 220 transmits and receives signals through imager cable 222.

In these figures, the hardware that mounts the lens and the prism has been omitted for clarity. In addition, schematic optical rays are shown in FIGS. 23 and 24 purely as an aid to understanding. The optical system shown for camera 224 is chosen for illustration purposes, and is not meant to represent the optics that would actually be used in electronic borescope 500. Such optical systems are well known in the art, and are not part of this invention.

Fixed base 182 of translation stage 180 is fastened to distal baseplate 514 which in turn is fastened to borescope probe tube 512.

The position of moving table 184 is controlled by a positioning cable 482, which is wrapped around a positioning pulley 484. Positioning cable 482 is clamped to moving table 184 through a distal motion clamp 486. Pulley 484 is mounted to baseplate 514 through a pulley mounting shaft 485.

Motion clamp 486 supports a distal fiber clamp 492, which in turn supports an illumination fiber bundle 127. Fiber bundle 127 is also supported and attached to moving table 184 by a fiber end clamp 494. Fiber end clamp 494 has internal provision for expanding the bundle of fibers at the end to form fiber output surface 129 (shown in FIG. 25).

Fiber bundle 127 and imager cable 222 are both supported by two distal cable stabilizer clamps 490, which are in turn clamped to and supported by positioning cable 482. The more distal cable stabilizer clamp 490 is captured inside a distal stabilizer slot 491, which is itself attached to baseplate 514.

Also mounted to distal baseplate 514 is a transducer mounting bracket 367, which in turn supports a linear position transducer 360. Transducer 360 is attached to moving table 184 through a transducer operating rod 361 and a transducer attachment bracket 369. Position transducer cable 366 extends from the rear of the transducer towards the proximal end of the borescope. Transducer cable 366 is clamped in transducer cable clamp 371 so that tension on cable 366 is not transferred to transducer 360. Clamp 371 is mounted to baseplate 514.

FIGS. 26 through 29 are respectively a plan view, a left side elevation view, a right side elevation view and a proximal end elevation view of the proximal end of electronic measurement borescope 500. In these views proximal housing 510 has been sectioned to allow viewing of the internal components. In FIG. 26, borescope probe tube 512 has been sectioned as well, for the same reason.

Figure 29:
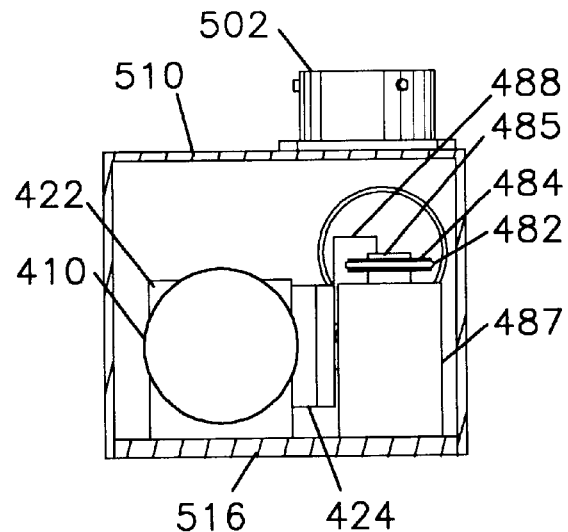
FIG. 29 is a proximal end elevation view of the internal structures of the proximal end of the third embodiment.

In FIG. 26, imager cable 222, transducer cable 366, and actuator cable 411 have been shown cut short for clarity. In FIG. 29, the same cables have been eliminated, for the same reason In FIGS. 26 through 29 the proximal end of positioning cable 482 is wrapped around a positioning pulley 484. Pulley 484 is supported by a mounting shaft 485, which in turn is mounted to proximal baseplate 516 through a pulley support bracket 487.

The proximal end of fiber bundle 127 is attached to illumination fiber optic connector 128. The proximal ends of imager cable 222 and position transducer cable 366 are attached to electronic connector 502. Connector 502 is supported by proximal housing 510. Housing 510 also supports borescope probe tube 512 through bulkhead 498. Cables 222 and 366 are clamped in bulkhead 498. Cable 366 is stretched taught between the distal and proximal ends of probe tube 512 before being clamped at both ends, while cable 222 is left slack as shown.

Clamped to positioning cable 482 is a proximal motion clamp 488. Clamp 488 is supported by a proximal translation stage 496, which is in turn mounted to proximal baseplate 516 through a proximal stage support bracket 499.

The position of proximal translation stage 496 is controlled by the action of actuator 410 through actuator attachment bracket 424. Bracket 424 is attached to the moving table of translation stage 496. Actuator 410 contains an actuator output shaft 413 which operates bracket 424 through an actuator attachment bushing 426. Actuator 410 is attached to proximal baseplate 516 through an actuator mounting bracket 422.

Actuator 410 is shown as a motorized micrometer. Actuator electrical cable 411 connects actuator 410 to electronic connector 502.

As shown in FIG. 30, electronically this embodiment is very similar to the second embodiment (compare FIG. 16). The primary difference is that the video camera back 134 in FIG. 16 has been split into solid state imager 220 and imager controller 221 in FIG. 30.

Operation of the Third Embodiment

This third embodiment contains the essentially the same elements as did the second embodiment, and from the user's standpoint the operation is virtually the same as the operation of that embodiment, which was described above.

The key to this third embodiment is that the motion of actuator 410 is transferred to proximal translation stage 496, thence to positioning cable 482, and finally to moving table 184 at the distal end of the scope. As a result, camera 224 is moved a known distance along a straight line path, which allows one to make dimensional measurements as I have described in the first embodiment. This third embodiment has the advantage that the image quality does not depend on the length of the borescope, thus making this of most interest when the object to be inspected is a long distance from the inspection port.

The optical quality of objective lens 121 can be made higher than the optical quality of a rigid borescope. However, solid state imager 220 will in general not have as high a resolution as do external video imagers such as video camera back 134 which was used in the first two (BPA) embodiments. Thus the tradeoffs in image quality between the BPA embodiments and this EMB cannot be encompassed by a simple statement.

Distal translation stage 180 is shown implemented in FIGS. 23 to 25 with a ball bearing slide. This could also be either a crossed roller slide or a dovetail slide. The slide selected will depend on the characteristics of the application of the EMB.

A dovetail slide can be made smaller than either of the other two options, so that the smallest EMB can be made if one were used. A dovetail slide would also have more friction than the other two options, and this would not always be a disadvantage. For instance, if the EMB were to be used in a high vibration environment, the extra friction of a dovetail slide would be valuable in damping oscillations of the translation stage position.

With this third embodiment, any error due to rotational motion of the translation stage will not act through a long lever arm, unlike with the first two (BPA) embodiments. Thus, the translation accuracy of the stage is less critical in this embodiment, which means that it is more feasible to use a less accurate ball or dovetail slide instead of a crossed roller slide.

The elimination of the long lever arm is a second reason why this third embodiment will be preferred when the object to be inspected is distant from the inspection port.

Because fiber bundle 127 is moved along with camera 224, the illumination of the camera's field of view does not change as the camera's position is changed. Both fiber bundle 127 and imager cable 222 must move with the camera, thus they are directly supported by positioning cable 482 to avoid putting unnecessary forces on moving table 184.

It is possible to provide a second pulley and cable arrangement to take up the load of the fiber bundle 127 and imager cable 222, thus eliminating any stretching of positioning cable 482 due to that load, but that makes it more difficult to keep the assembly small, and there is little or no advantage when the position transducer is located at the distal end of the scope, as I have shown.

Distal cable stabilizer clamps 490 fasten fiber bundle 127 and imager cable 222 to positioning cable 482 to keep them out of the way of other portions of the system. Distal stabilizer slot 491 controls the orientation of the more distal stabilizer clamp 490 to ensure that fiber bundle 127 and cables 222 and 482 keep the desired relative positions near stage 180 under all conditions.

Fiber bundle 127 and imager cable 222 must have sufficient length to accommodate the required translation of camera 224. Position transducer cable 366 is of fixed length. Thus, transducer cable 366 is fixed at the proximal end of borescope 500 to bulkhead 498 and is clamped between bulkhead 498 and transducer cable clamp 371 with sufficient tension that it will remain suspended over the length of probe tube 512. Fiber bundle 127 and imager cable 222 are run over the top of transducer cable 366 so that transducer cable 366 acts to prevent fiber bundle 127 and imager cable 222 from contact with positioning cable 482. In this manner, unnecessary increases in the frictional load on positioning cable 482 due to contact with the other cables are avoided.

This simple scheme for keeping the cables apart will work only for a short EMB. For a longer EMB, one can place a second cable spacer and clamp similar to bulkhead 498 near the distal end of probe tube 512, but far enough behind the hardware shown in FIGS. 23–25 so that the cables can come together as shown there. Then all of the cables will be under tension between the proximal and distal ends of the EMB. In such a system, one could also use a long separating member, placed between positioning cable 482 and the other cables, to ensure that they do not come into contact.

For very long EMBs, it will be necessary to support all of the cables 127, 222, 366, and 482 at several positions along the length of probe tube 512, in order to prevent them from sagging into each other and to prevent positioning cable 482 from sagging into the wall of tube 512. Such support can be provided by using multiple cable spacers fixed at appropriate intervals along the inside of tube 512. These spacers must remain aligned in the correct angular orientation, so that the friction of cable 482 is minimized.

The end of fiber bundle 127 is expanded as necessary in fiber end clamp 494 so that the illumination will adequately cover the field of view of camera 224 at all measurement distances of interest.

Viewport 518 is sized to ensure that the field of view of camera 224 is unobstructed for all camera positions available with stage 180. Clearly, this viewport can be sealed with a window (not shown), if necessary, to keep the interior of the distal end of the EMB clean in dirty environments. The window could be either in the form of a flat, parallel plate or in the form of a cylindrical shell, with the axis of the cylinder oriented parallel to the direction of motion of moving table 184. In either case, the tolerances on the accuracy of the geometrical form and position of the window must be evaluated in terms of the effects of those errors on the measurement.

All camera lines of sight will be refracted by the window. This can cause three types of problems. First, the window could cause an increase in the optical aberrations of the camera, which will make the image of the object less distinct. In general this will be a problem only if a cylindrical window is placed with its axis far away from the optical axis of camera 224, or if the axes of the inner and outer cylindrical surfaces of the window are not coincident. Secondly, differences in how the line of sight is refracted over the field of view of the camera will change the distortion of the camera from what it would be without the window in place. This would cause a problem only if the distortion were not calibrated with the window in place. Third, differences in how the line of sight is refracted as the camera is moved to different positions would cause errors in the determination of the apparent positions of a point of interest. This is potentially the largest problem, but once again, it is easily handled by either fabricating and positioning the window to appropriate accuracies, or by a full calibration of the system with the window in place, using the calibration methods to be described later.

It is a design decision whether to locate position transducer 360 at the distal end of EMB 500, as I have shown, or whether to locate it at the proximal end of the scope. Either way will work as long as appropriate attention is paid to minimizing errors. For the distally mounted transducer, because of the small size required, it is not possible to achieve the level of accuracy in the transducer that one can get with the proximally mounted transducer shown in the second embodiment. However, if a proximally mounted transducer is used, one must carefully consider the errors in the transfer of the motion from the proximal to the distal end of the scope.

When it is mounted distally, transducer 360 must be small enough to fit in the space available and have sufficient precision for the purposes of the measurement. Suitable transducers include linear potentiometers or linear variable differential transformers (LVDTs). Note that both of these options are absolute position transducers, so that the issue of determining a home position does not exist if they are used.

Suitable linear potentiometers are available from Duncan Electronics of Tustin, Calif. or Sfernice of Nice, France who are represented in the U.S.A. by Dynamation Transducers of Holliston Mass. Suitable LVDTs are available from Lucas Control System Products of Hampton, Va. For instance, model 249 XS-B from Lucas is 4.75 mm diameter by 48 mm long for a measurement range of at least 13 mm.

These small, distally mounted transducers must be calibrated. In fact, LVDT manufacturers provide calibration fixtures, using micrometers as standards. As will be discussed in the error analysis, what matters most to the performance of the measurement instrument is repeatability. The repeatability of small linear potentiometers is generally 1 part in $10^4$, or 0.0001 inch per inch of travel. The repeatability of an LVDT is determined by the signal to noise ratio of the signal processing electronics. A signal to noise ratio of 1 part in $10^5$ is easily obtained with small signal bandwidth, and 1 part in $10^6$ is quite feasible, though more expensive to obtain. These available levels of repeatability are quite consistent with the purposes intended for the instrument.

If the EMB is to be used over a large range of temperatures, it will be necessary to include a temperature transducer at the distal end of the scope, so that the temperature sensitive scale factor of the distal position transducer can be determined and taken into account in the measurement.

With the distally mounted position transducer, the only backlash that matters is the backlash between moving table 184 and position transducer 360 due to the necessary clearance between transducer operating rod 361 and transducer attachment bracket 369. This backlash will not be negligible, in general, so that the measurement procedure must use the anti-backlash elements of the measurement procedure detailed above in the description of the first embodiment. (Briefly, this means that the camera position is always determined with the camera having just moved in one particular direction.) Since the system shown in FIG. 30 is a closed-loop positioning system, it is straightforward to implement anti-backlash procedures automatically in the positioning software, and the user then need not be concerned with them.

The position transducer will not correctly measure the position of the camera if the measurement axis of the transducer is misaligned with the axis of camera motion. Such a misalignment causes a so-called "cosine" error, because the error is proportional to the cosine of the angular misalignment. This error is small for reasonable machining and assembly tolerances. For instance, if the misalignment is 10 milliradians (0.6 degrees), the error in the distance moved between camera positions is 1 part in $10^4$. When necessary for very accurate work, this error can be determined and taken into account in the measurement, by scaling the transducer position data accordingly. The first two embodiments are also subject to this error, but in those cases the necessary mechanical tolerances are easier to achieve. Note that an instrument suffering from this error will systematically determine distances to be larger than they really are.

There could be a thermal drift of the camera position if positioning cable 482 has different temperature coefficient of expansion than does probe tube 512 or if the instrument is subjected to a temperature gradient. Such a drift would not be a problem over the small time that it takes to make a measurement, because it is only the differential motion of the camera between viewing positions P1 and P2 that is important. In more general terms, it doesn't matter if there is a variable offset between proximal position commanded and the distal position achieved, as long as any such offset is constant over a measurement.

Of course, differential thermal expansion of positioning cable 482 and borescope tube 512 would cause a varying tension in cable 482. Thus, unless cable 482 and 512 are made of materials with the same expansion coefficient, it may be necessary to spring load pulley support bracket 487. Whether such spring loading is necessary is dependent on the length of tube 512 and the temperature range over which the EMB must operate, as well as the difference in temperature coefficients.

A significant level of static friction (stiction) in translation stage 180 would require that the EMB be implemented with a distal position transducer, since otherwise there would be considerable uncertainty added to the position of the camera. Dovetail slides tend to have significant stiction, so that use of a dovetail slide will almost certainly require a distal position transducer. If the stiction is too severe, the position setability of the camera will be compromised, which could make the instrument frustrating to use.

Clearly, the EMB could be implemented with another sort of motion actuator 410, for instance, an air cylinder.

I have shown that there is used a proximal translation stage 496 between actuator 410 and positioning cable 482. Clearly, this is not strictly necessary as cable 482 could be clamped directly to output shaft 413 of actuator 410, provided that output shaft 413 does not rotate and can sustain a small torque.

Clearly the EMB could also be implemented with a miniature motor and lead screw placed at distal end. This eliminates the requirement for transfer of motion from the proximal to the distal end, but it then requires more space at the distal end. The advantage is that this could be used to embody an electronic measurement endoscope, that is, a flexible measurement scope. Such a scope would be flexible, except for a relatively short rigid part at the distal end.

DESCRIPTION OF A FOURTH EMBODIMENT

FIGS. 31 and 32 show respectively plan and left side elevation views of the distal end of a fourth mechanical embodiment of the invention, which I call the electronic measurement endoscope (EME). This fourth embodiment is similar to the third embodiment, except that the positioning pulley and cable system has been replaced here by a positioning wire 532 which is enclosed except at its distal and proximal ends by a positioning wire sheath 534.

In FIGS. 31 and 32 many of the same elements are shown as in the third embodiment, and only those elements most directly related to the discussion of this fourth embodiment are identified again.

The distal end of positioning wire 532 is clamped by distal positioning wire clamp 542. Clamp 542 is attached to the moving table of translation stage 180. Positioning wire sheath 534 is clamped to distal baseplate 514 with a distal sheath clamp 536.

The external housing of the endoscope now consists of two portions, a flexible endoscope envelope 538 and a distal rigid housing 540. Rigid housing 540 is attached to the end of flexible envelope 538 to form an endoscope which is flexible along most of its length, with a relatively short rigid section at its distal end.

Flexible envelope 538 includes the necessary hardware to allow the end of the endoscope to be steered to and held at a desired position under user control. Such constructions are well known in the art and are not part of this invention.

As in the third embodiment, imager cable 222 and illumination fiber bundle 127 are supported by and clamped to the element which transfers motion from the proximal to the distal end of the scope. Here cable 222 and fiber bundle 127 are clamped by a distal cable stabilizer clamp 490 which is itself clamped to positioning wire 532. Also as in the third embodiment, clamp 490 is captured inside distal stabilizer slot 491 to control its position and orientation.

As in the third embodiment, the distal end of illumination fiber bundle 127 is supported by distal fiber clamp 492 and fiber end clamp 494. In this embodiment, fiber clamp 492 is attached to positioning wire clamp 542.

Imager cable 222, illumination fiber bundle 127, position transducer cable 366, and positioning wire sheath 534 all pass through and are clamped to distal end cable clamp 544, which is located at the proximal end of distal rigid housing 540. Positioning wire sheath 534 is positioned in the center of cable clamp 544, while the other three cables are arranged around it in close proximity. Positioned at suitable intervals within flexible endoscope envelope 538 are a number of cable centering members 546, through which all of the cables pass.

The position of stage 180 is monitored by linear position transducer 360, which is mounted to distal baseplate 514 with transducer mounting bracket 367.

Operation of the Fourth Embodiment

Clearly, if the proximal end of sheath 534 is clamped to proximal baseplate 516 of the third embodiment, and if actuator 410 is attached to positioning wire 532, then the motion of the actuator will be transferred to distal translation stage 180. Thus, the operation is identical to that of the third embodiment, except that this embodiment is now a flexible measurement endoscope which can be brought into position for measurements in a wider range of situations.

When this EME is steered to a desired position, flexible envelope 538 will necessarily be bent into a curve at one or more places along its length. Bending envelope 538 means that one side of the curve must attain a shorter length, and the opposite side a longer length, than the original length of the envelope. The same holds true for components internal to envelope 538, if these components have significant length and are not centered in envelope 538. Thus, in order to prevent the bending of the EME from affecting the position of translation stage 180, it is necessary to ensure that positioning wire 532 runs down the center of envelope 538. Cables 222, 366, and fiber bundle 127 are also run as close to the center of envelope 538 as feasible, to minimize the stress on these cables as the EME is steered.

This embodiment almost certainly requires the use of a distally located linear position transducer 360, as shown, because there is likely to be considerable stiction in the motion of positioning wire 532 inside sheath 534.

Imager cable 222 and illumination fiber bundle 127 must have sufficient length to reach the most distal position of stage 180. These, as well as cable 366, are clamped to housing 540 through distal end cable clamp 544 so that no forces can be transferred from them to the measurement hardware inside housing 540. As the EME is bent, there will be small changes in the lengths of cables 222 and 366 and fiber bundle 127. Thus, there must be sufficient extra length of these cables stored at the proximal end, or throughout the length of the endoscope, so that no large forces are generated when the EME is bent.

When stage 180 is moved away from its most distal position, the portion of cable 222 and fiber bundle 127 which are contained within housing 540 will bend so as to store their now excess lengths in the portion of housing 540 behind the proximal end of baseplate 514.

EMBODIMENTS USING OTHER CAMERA MOTIONS

A. Introduction

In the preferred embodiments, I teach the use of straight line camera motion between viewing positions, with a fixed camera orientation, to perform the perspective measurement. The reasons that I prefer these embodiments are that they are simple and of obvious usefulness. However, my invention is not restricted to the use of straight line camera motion or fixed camera orientation. Other camera motions are possible and can also be used when making a perspective measurement. Some of these more general camera motions will be useful for specific applications. Below, I will show how to perform the measurement when using any arbitrary motion of the camera, and when using multiple cameras.

This generalized method of perspective dimensional measurement that I teach here has an important application in improving the accuracy of the measurement made with my preferred embodiments. Even with the best available hardware, the motion of the camera will not conform to a perfect straight line translation. In this section, I show how to take such motion errors into account when they are known. In the calibration section I will show how to determine those errors.

B. Linear Camera Motion

Figure 33:
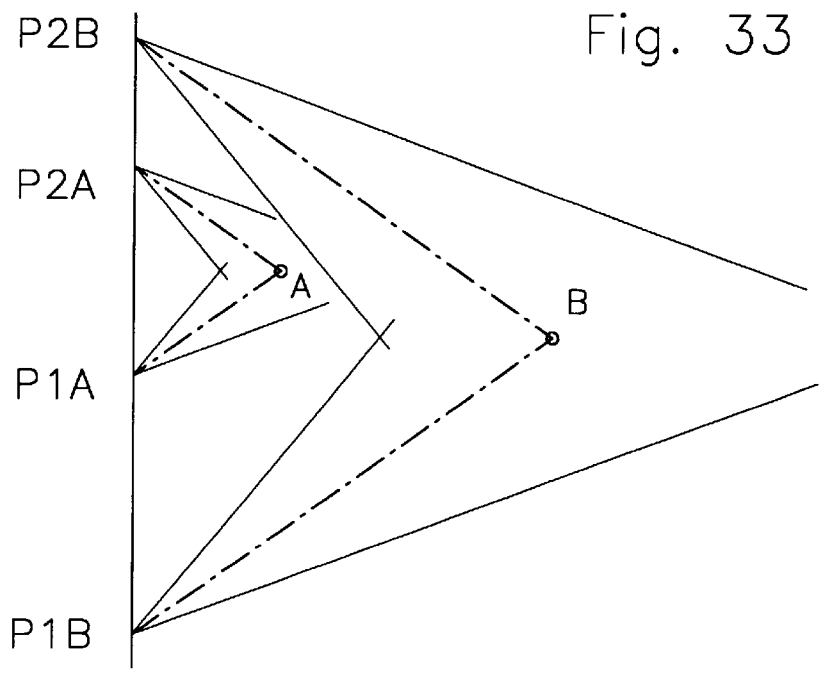
FIG. 33 depicts the perspective measurement mode 2 process when a camera moves in a straight line path, but when the orientation of the camera is not fixed.

FIG. 33 depicts the geometry of a mode 2 perspective measurement of the distance between the points A and B being made with a camera moving along a linear path, but where the camera orientation does not remain constant as the camera position changes. Compare FIG. 33 to FIG. 10. In FIG. 33, the points A and B are chosen to lie at considerably different distances from the path of the camera in order to emphasize the differences that a variable camera orientation creates.

The situation shown in FIG. 33 represents the geometry of a measurement which may be made with any number of different physical systems. For instance, the camera could be movable to any position along the path, and the camera could be rotatable to any orientation with respect to that path. Or, the camera rotation could be restricted, for instance, to be about an axis perpendicular to FIG. 33. Another possibility is that the camera orientation is restricted to only a relatively small number of specific values, such as, for instance, the two specific orientations shown in the Figure. A third possibility is that the positions the camera can take are restricted to a relatively small number, either in combination with rotational freedom or in combination with restricted rotation.

If either the positions or the orientations of the camera are small in number, then one can use the well-known kinematic mounting principle to ensure that these positions and/or orientations are repeatable to a high degree of accuracy.

The basic concept of the measurement geometry shown in FIG. 33 is that the camera is rotated towards the point of interest at any viewing position. This is useful, for instance, when the camera has a narrow field of view, and when one desires to use a long perspective baseline.

Figure 45:
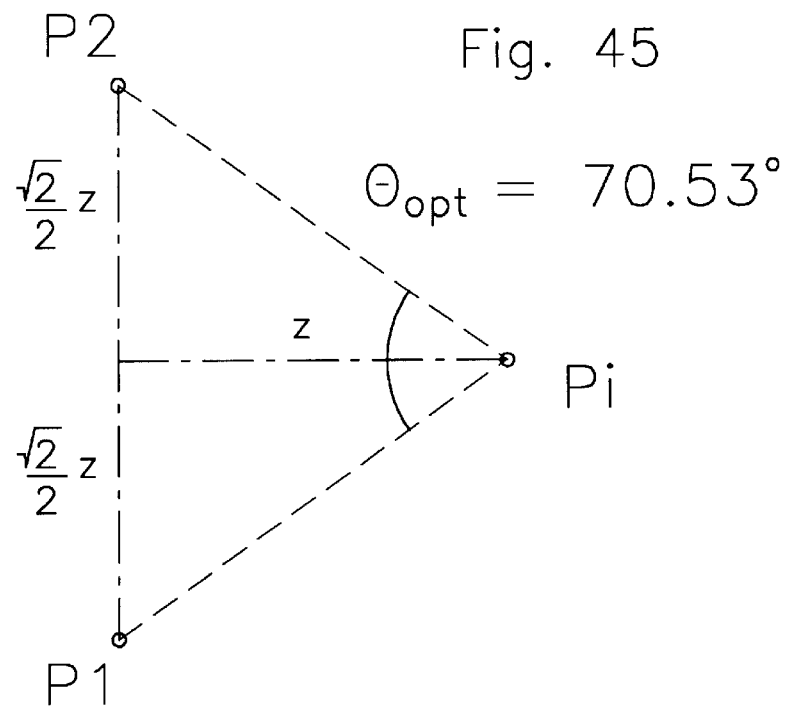
FIG. 45 depicts the optimum measurement geometry as determined in error analysis coordinates.

In fact, as I show below in the error analysis, FIG. 33 shows the overall optimum way to make a perspective measurement, provided that the angle subtended at the point of interest by the perspective baseline is always kept within an optimum range of values, regardless of the position of the point of interest. If the point being located lies midway between the two viewing positions, then the optimum subtended angle is 70.53 degrees, with angles between 40 degrees and 100 degrees giving measurement results nearly as good as the optimum. If the point being located does not lie exactly midway between the two observation positions, the optimum subtended angle becomes somewhat greater than 70.53 degrees, but there is still a rather broad range of angles which will provide good measurement results. This broad minimum in measurement error is depicted in FIG. 47, where the measurement geometry is defined in FIG. 46. FIG. 45 depicts the optimum subtended angle when the point of interest is located midway between the viewing positions. These Figures and the related issues are explained at length below in the sub-section entitled "Sensitivity of the Measurement in Error Analysis Coordinates".

To summarize, there are optimum perspective baselines for making each of the point position determinations in the mode 2 perspective measurement, and those optimum baselines are proportional to the distance between the object point and the midpoint between the two camera viewing positions. This optimum measurement situation is approximately as shown in FIG. 33.

I also show in the error analysis that it is much more important that the perspective baseline be adjusted to be proportional to the distance of the point of interest than it is that the point of interest be viewed with precisely the optimum subtended angle. This situation is exactly as shown in FIG. 33. Note that the procedures described in the operation of the first embodiment which move the camera so that the points of interest are seen to move from one side of the field of view to the other achieve this condition automatically for the preferred embodiments.

It may or may not be precisely optimum for the camera optical axis to be aligned exactly to the point of interest during the measurement as shown in FIG. 33. The optimum alignment of the camera is discussed at length in the error analysis, where it is explained how to determine what is the optimum camera alignment, given the characteristics of the camera. It is certainly the case that for most real cameras, the alignment of the point of interest with the optical axis of the camera will not be far from optimum.

The disadvantage of the measurement geometry shown in FIG. 33 is that it requires accurately known camera motion in two degrees of freedom rather than just one, as do my preferred embodiments. Its advantage is that it has the smallest possible random measurement error.

It should also be clear to the reader that two cameras could be used to make the measurement depicted in FIG. 33. If two cameras are used, it is still necessary to move one of the cameras with respect to the other to adjust the perspective baseline to the optimum value, when locating points at different distances and relative positions. When viewing an inaccessible object, the preferred implementation is to mount both cameras to a single probe assembly, but it is also possible to mount each camera on a separate probe, just as long as the relative positions and orientations of the cameras are known accurately. I discuss below the parameters of the measurement geometry which must be known in order to make the measurement in the most general case.

One advantage of a two camera system is that the requirement for a second degree of freedom of motion can be eliminated under certain conditions, since the orientation of each of the cameras could be fixed at an optimum angle for the measurement, and the point of interest could then be brought into the field of view of each camera by translating the camera to an appropriate point along the path. In this case, the orientation of each camera would be fixed so that its optimum field angle (defined in the error analysis) would be aligned approximately 35 degrees away from the perpendicular to the line of motion of the cameras, and so that the included angle between the optical axes of the two cameras would be approximately 70 degrees. This situation can be envisioned from FIG. 33 by assuming that there is an upper camera, which is used at the viewing positions P2A and P2B, and a lower camera, which is used at the viewing positions P1A and P1B, and that both cameras can be moved along the single line of motion shown in the Figure.

A second advantage of a two camera system is that the measurement data can be acquired in the time necessary to scan one video frame, once the cameras are in position, if the digital video "frame grabber" technology mentioned earlier is used. Such quasi-instantaneous measurements are useful if the object is moving or vibrating. For the same reason, such a system could reduce the stability requirements on the mounting or support structure for the measurement instrument.

A disadvantage of a two camera implementation of the measurement shown in FIG. 33 is that there will be a minimum perspective baseline set by the physical size of the cameras. If the camera orientations are fixed, the minimum perspective baseline implies a minimum measurement distance. A second disadvantage of the fixed camera orientation variant of two camera system is that there is also a maximum measurement distance for camera fields of view smaller than a certain value, since there will always be a maximum value of the perspective baseline.

C. Circular Camera Motion

Figure 34:
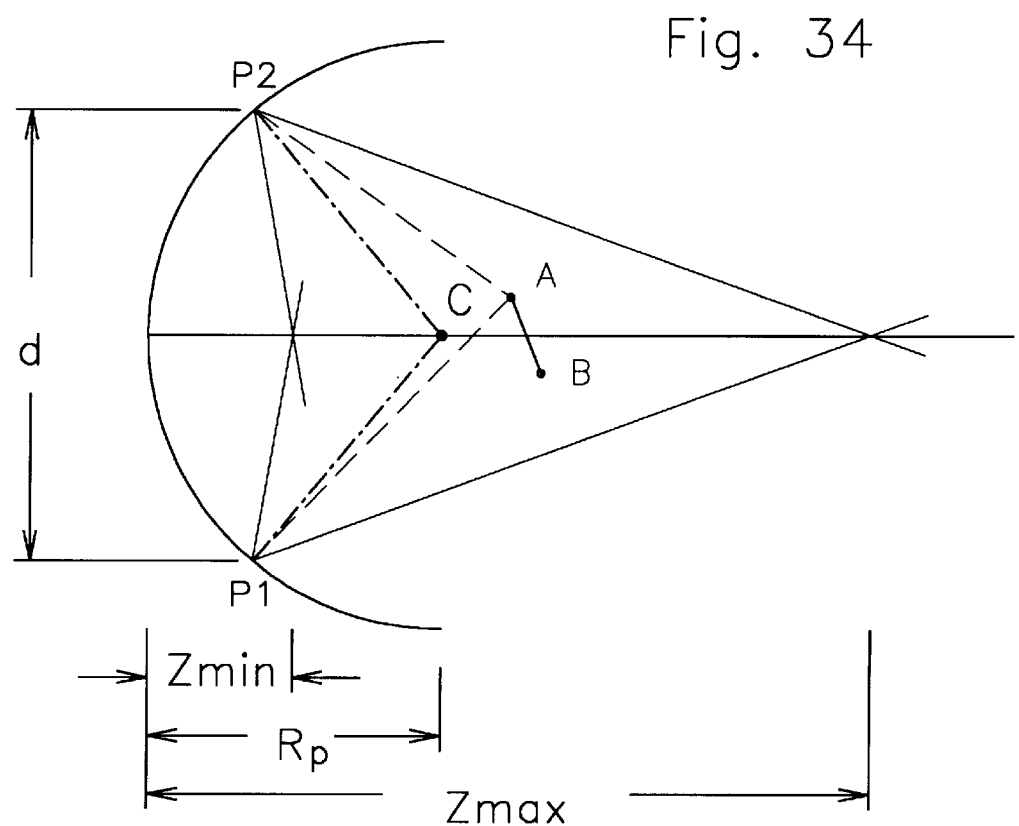
FIG. 34 depicts the perspective measurement mode 1 process when a camera is constrained to a circular path which lies in the plane of the camera optical axis.

FIG. 34 depicts a mode 1 perspective measurement being made with a camera moving along a curved path. The curve is a section of a circular arc, with a radius of curvature $R_p$ and center of curvature at C. The optical axis of the camera lies in the plane containing the circular path. The camera orientation is coupled to its translation along the path so that the optical axis of the camera always passes through C as the camera moves along the path.

The advantage of this arrangement, as compared to my preferred embodiments, is that a much larger perspective baseline can be used without losing the point of interest from the camera field of view, for objects located near the center of curvature, C, when the field of view of the camera is narrow. Thus, the measurement system shown in FIG. 34 can potentially make lower random measurement errors.

As is clear from FIG. 34, there will usually be a maximum distance for which perspective measurements can be made, as well as a minimum distance, at any given value of the perspective baseline. In order to make measurements at large distances, the system of FIG. 34 requires a smaller baseline to be used than does a similar straight line motion system. For certain combinations of d, $R_p$, and camera field of view it is possible for both the minimum and maximum measurement distances to decrease as d increases. Thus, this curved camera path system has the disadvantage, as compared to my preferred embodiments, of having a limited range of distances over which measurements can be made.

This curved camera path system would be preferred in cases where only a small range of object distances are of interest, and where there is plenty of space around the object to allow for the relatively large camera motions which are feasible. I consider the primary operating range of the circular camera path system shown in FIG. 34 to be ($0 \leq z \leq 2R_p$).

Another disadvantage of the system shown in FIG. 34 for the measurement of inaccessible objects is the difficulty of moving the required hardware into position through a small inspection port.

The measurement system taught by U.S. Pat. No. 4,895,431 to Tsujiuchi, et. al. and U.S. Pat. No. 5,432,543 to Hasegawa, et. al. moves the camera along a circular path with the center of curvature on the opposite side of the camera as compared to that shown in FIG. 34. In that case, the minimum measurement distance at any fixed baseline is increased over that of the straight line motion of my preferred embodiments, and even more so as compared to the system shown in FIG. 34. Thus, considering only the geometry of the perspective measurement, that prior art system is even less suited to measurements at short distances than are my preferred embodiments, and it has no advantage at long distances.

The method chosen for using a transducer to determine the camera's position along the path will depend on how this path is generated mechanically. For instance, if a circular path is generated by swinging the camera about a center point, then the position will probably be most conveniently transduced as an angular measurement. If the path is generated by moving the camera along a circular track, then the position will probably be transduced as a linear position. The method of transducing the position of the camera becomes an issue when considering how to describe an arbitrary motion of the camera, as I discuss below.

In the sub-section entitled "The Effects of Camera Characteristics and Orientation", I show how to determine the optimum operating parameters for this circular camera motion embodiment. Since the camera orientation is coupled to the position of the camera along the path, it turns out that the optimum angle subtended by the perspective baseline at the point of interest can depend upon the position of the point in a more complicated manner than in linear motion embodiments. The situation is summarized for the primary operating range of the system shown in FIG. 34 in a table (Table 1) in the referenced subsection.

It should be clear to the reader that two cameras can be used with the circular camera path just as in the case of a linear camera path. In fact, mode 2 measurements can use up to four cameras to make the measurement, with either linear or circular camera motion. These cameras can be used with any camera path, and in fact, there is no need for all cameras to follow the same path. The fundamental requirements, as will be shown, are simply that the relative positions and orientations as well as the distortions and effective focal lengths of all cameras be known.

Figure 35:
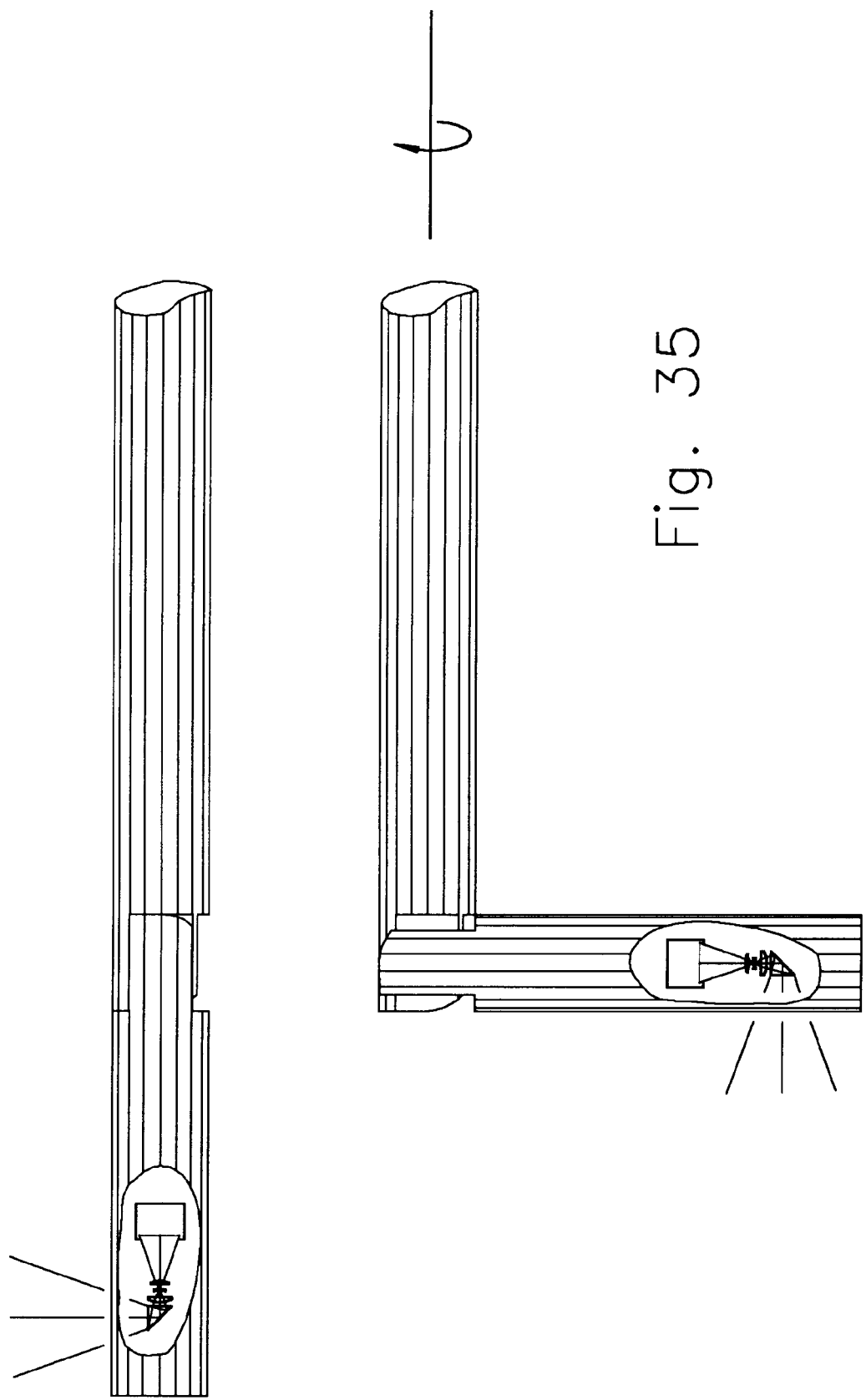
FIG. 35 shows an endoscope which implements a circular camera path where the camera view is perpendicular to the plane of the path.

A system using another potentially useful camera motion path is shown in FIG. 35. Here the camera is moved in a circular are, as in FIG. 34, but now the camera is oriented to view substantially perpendicular to the plane of the are. In FIG. 35 a tiny video camera is placed at the tip of a rigid borescope, similar to my third and fourth preferred embodiments. This borescope has an end section with the capability of being erected to a position perpendicular to the main borescope tube. When this erection is accomplished the camera looks substantially along the axis of the borescope. To make the perspective measurement, the borescope (or some distal portion of it) is rotated about its axis, thus swinging the camera in a circular path. In this case it is the rotation of the camera about the optical axis which is coupled to the translation of the camera. The camera position would be transduced by an angular measurement in this system.

An advantage of the system shown in FIG. 35 is that it allows both large and small perspective baselines to be generated with an instrument that can be inserted through a small diameter inspection port. Of course, it still would require that there be considerable space in the vicinity of the objects to be inspected to allow for the large motions which can be generated.

The instrument shown in FIG. 35 could combine the circular motion just described with an internal linear motion as in my fourth embodiment to offer the capability of making measurements either to the side or in the forward direction.

Operation of Embodiments Using Arbitrary Camera Motion

A. Description of Arbitrary Camera Motion

I must first explain how I describe an arbitrary camera motion, before I can explain how to make a measurement using it. To make accurate measurements, the motion of the camera must be accurately known, either by constructing the system very accurately to a specific, known geometry, or by a process of calibration of the motion. If calibration is to used to determine the motion of the camera, then that motion must be repeatable to the required level of precision, and the method of calibration must have the requisite accuracy.

In general, the true position of the camera along its path is described by a scalar parameter p. This parameter could be a distance or an angle, or some other parameter which is convenient for describing the camera position in a particular case.

The position of the camera is monitored by a transducer which produces an output $\eta(p)$. Here, $\eta$ is an output scalar quantity which is related to the true position along the path, p, by a calibration curve $p(\eta)$.

The geometrical path of the camera in space is expressed as a vector in some convenient coordinate system. That is, the physical position of the camera (more precisely, the position of the nodal point of the camera's optical system) in space is expressed as a vector, $r_c(p(\eta))$ or $r_c(\eta)$, in a coordinate system that I call the external coordinate system or the global coordinate system.

Likewise, the orientation of the camera in space is expressed a rotation matrix, which describes the orientation of the camera's internal coordinate system with respect to the global coordinate system. Thus, the camera's orientation at any point along its path is expressed as $R_c(p(\eta))$ or $R_c(\eta)$. The matrix $R_c$ transforms any vector expressed in the global coordinate system into that vector expressed in the camera's internal coordinate system. The matrix $R_c$ is the product of three individual rotation matrices, each of which represents the effect of rotation of the camera's coordinate system about a single axis:

$$R_c(\eta) = R_z(\theta_z(\eta)) R_y(\theta_y(\eta)) R_x(\theta_x(\eta)) \qquad (18)$$

where $\theta_z$, $\theta_y$, and $\theta_x$ are the angles that the coordinate system has been rotated about the corresponding axes.

Now, in general, the terms $r_c(\eta)$ and $R_c(\eta)$ will not be independent quantities, but will be coupled together by the geometry and construction of the perspective measurement system. An example was shown in FIG. 34, where the camera's orientation is coupled to its position, so that the optical axis always passes through the center of curvature of the camera's path.

If two or more cameras are used, then each one will have a location and orientation expressed similarly. I will assume that the same global coordinate system is used to describe the motion of all cameras. This must be the case, but if at some point in the process separate global coordinate systems are used, and if the relationships between these separate global coordinate systems are known, then it is possible to express all of the camera motions in a single global coordinate system in the manner shown below for expressing one coordinate system in terms of another.

To summarize the relationship between camera motion and the measurement, what is required is that the positions and orientations of the camera(s) be accurately known relative to an external (global) coordinate system. This coordinate system is fixed with respect to the instrument apparatus, but it has no inherent relationship to the object being measured. The position of the object in the global coordinate system becomes fixed only when the instrument is itself fixed at some convenient position with respect to the object. When this is done, the position of points on the object can be determined in the global coordinate system, or in some other closely related coordinate system which is also fixed with respect to the instrument apparatus.

B. The General Perspective Measurement Process

In measurement mode 1, the experimental data obtained are four camera image position coordinates ($x'_{im1}$, $y'_{im1}$, $x'_{im2}$, $y'_{im2}$) for each object point of interest and the readings of the camera position transducer, $\eta_1$ and $\eta_2$, at the two viewing positions P1 and P2.

As explained for the first preferred embodiment, the data processing begins by correcting the measured image point location data for distortion as expressed by Equation (2). Next, the data are scaled by the inverse of the effective focal length of the combined optical-video system as expressed by Equation (3). Then, for each object point of interest, the visual location vectors $a_{v1}$ and $a_{v2}$ are formed as expressed in Equation (4).

Next, the displacement vector between the two viewing positions is calculated in global coordinates as:

$$d_g(\eta_2,\eta_1) = r_c(\eta_2) - r_c(\eta_1) \qquad (19)$$

As stated previously, I call this vector the perspective displacement.

The relative rotation of the camera between the two viewing positions is calculated as:

$$R_{12}(\eta_2,\eta_1) = R_c(\eta_2)R_c^{-1}(\eta_1) \qquad (20)$$

Equation (20) simply says that the rotation of the camera between positions P1 and P2 is equivalent to the rotation of the camera in global coordinates at P2 minus the rotation it had at P1.

The perspective displacement is then re-expressed in the camera internal coordinate system at P1 by taking into account the rotation of the camera at that point. That is:

$$d_{v1} = R_c(\eta_1)d_g(\eta_2,\eta_1) \qquad (21)$$

The position of the object point of interest in the measurement coordinate system is then computed as:

$$r_m = \frac{1}{2}[a_{v1} \ R_{12}^{-1} \ a_{v2}][a_{v1} - R_{12}^{-1} \ a_{v2}]^{LI} \ d_{v1} \qquad (22)$$

where the measurement coordinate system is parallel to the internal coordinate system of the camera at P1, with its origin located midway between P1 and P2.

Equation (22) expresses how to locate a point in the measurement coordinate system under completely general conditions, for any arbitrary motion of the camera, provided that the motion is known accurately in some global coordinate system. If the motion is repeatable, it can be calibrated, and thus known.

To complete the mode 1 perspective dimensional measurement process, Equation (22) is used for both points A and B individually, then Equation (1) is used to calculate the distance between these points.

If two cameras are used, one simply uses each individual camera's distortion parameters to correct the image measured with that camera as in Equation (2). Then, the scaling by the inverse focal length is carried out for each individual camera as expressed by Equation (3). Then, for each object point of interest, the visual location vectors $a_{v1}$ and $a_{v2}$ are formed as expressed in Equation (4), where now the data in $a_{v1}$ were determined with one of the cameras and the data in $a_{v2}$ were determined with the other. The remainder of the data processing is identical whether one or two cameras are used to make the measurement.

Figure 36:
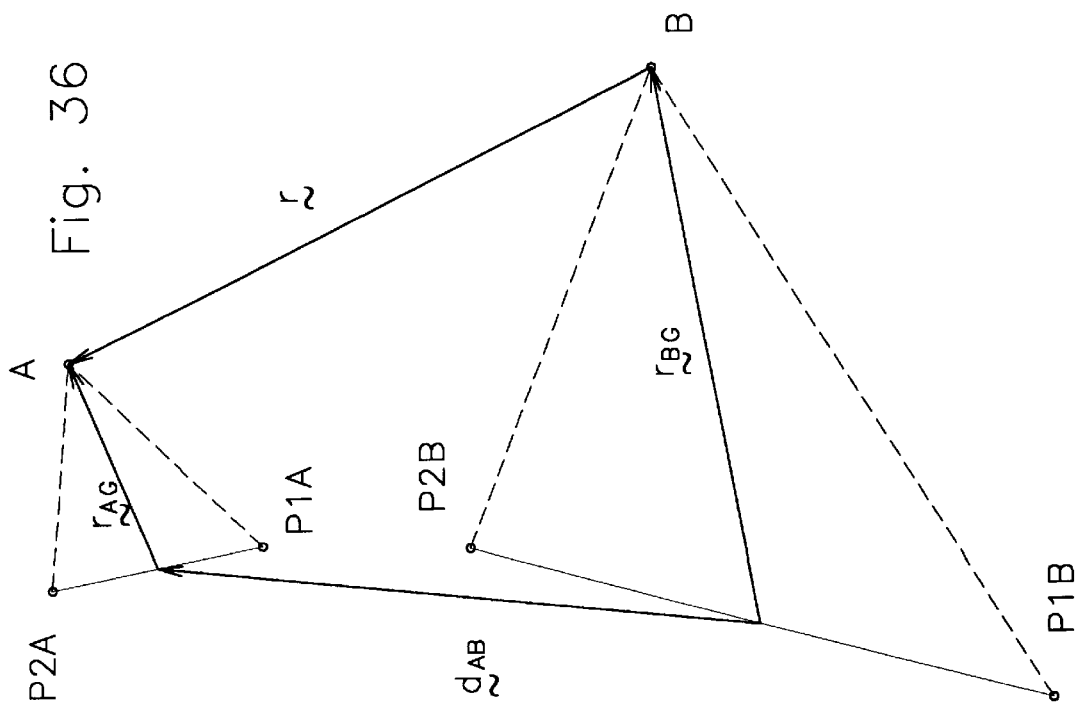
FIG. 36 depicts the measurement mode 2 process with a general motion of the camera.

The geometry of measurement mode 2 for an arbitrary camera motion is depicted in FIG. 36. The experimental data obtained are four camera image position coordinates ($x'_{im1}$, $y'_{im1}$, $x'_{im2}$, $y'_{im2}$) and the two readings of the camera position transducer $\eta_1$ and $\eta_2$, for each object point of interest. In this mode of measurement, the camera positions are not the same for each point of interest, so that there may be either three or four camera positions used for each distance to be determined.

FIG. 36 depicts the situation when the distance between two points, A and B, is to be determined. It is clear that this measurement mode makes sense only for a certain class of camera motion, object distance, object shape combinations. For instance, with the camera motion shown in FIG. 34, and a more or less planar object located near the center of curvature, C, there is little or no ability to view different portions of the object by moving the camera, so that there is no reason to use measurement mode 2.

Figure 37:
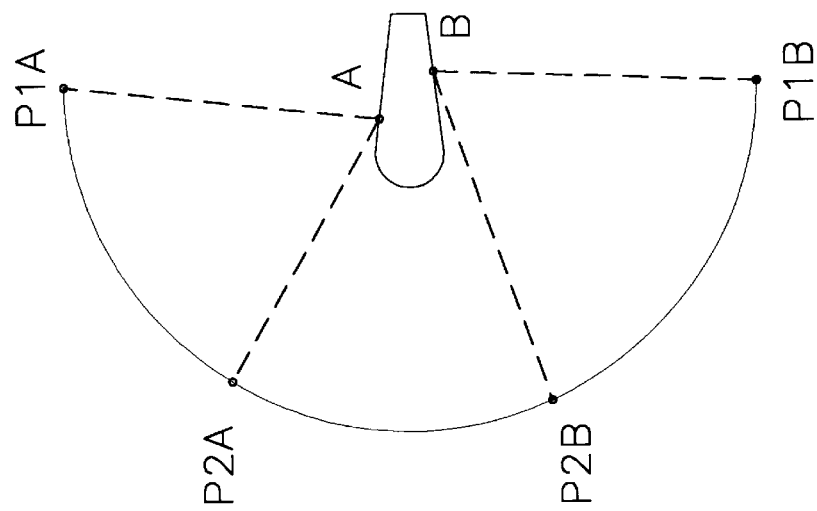
FIG. 37 depicts the measurement of a distance with the combination of circular camera motion and measurement mode 2.

However, as shown in FIG. 37, there are other situations when only the use of measurement mode 2 makes a measurement feasible. In FIG. 37, the distance between two points on opposite sides of an object is desired. The object has a shape and an orientation such that both points cannot be viewed from any single camera position which is physically accessible. As shown in FIG. 37, the combination of circular camera motion and measurement mode 2 allows this measurement to be made. This measurement could also be made with an arbitrary camera rotation embodiment of the system shown in FIG. 33.

Consider now that the measurements depicted in FIGS. 36 or 37 are to be performed. Say that the camera position transducer readings are $\{\eta_{1A}, \eta_{2A}, \eta_{1B}, \eta_{2B}\}$ at viewing positions {P1A, P2A, P1B, P2B} respectively. Then, the actual camera positions in the global coordinate system are $\{r_c(\eta_{1A}), r_c(\eta_{2A}), r_c(\eta_{1B}), r_c(\eta_{2B})\}$ respectively. Likewise, the orientations of the camera's coordinate system with respect to the global coordinate system are $\{R_c(\eta_{1A}), R_c(\eta_{2A}), R_c(\eta_{1B}), R_c(\eta_{2B})\}$.

In measurement mode 2, the positions of the points A and B are each determined independently by the basic point location process expressed by Equation (22) to give $r_{mA}$ and $r_{mB}$ respectively. According to that process, $r_{mA}$ is determined in a measurement coordinate system parallel to the coordinate system of the camera at P1A, while $r_{mB}$ is determined in a coordinate system which is parallel to the camera coordinate system at P1B.

The vectors giving the positions of points A and B are then re-expressed in the global coordinate system as:

$$r_{AG}=R_c^{-1}(\eta_{1A})r_{mA}$$

$$r_{BG}=R_c^{-1}(\eta_{1B})r_{mB} \qquad (23)$$

and the vector between the origin of the A measurement coordinate system and the origin of the B coordinate system in global coordinates is calculated as (FIG. 36):

$$d_{AB} = \frac{1}{2}[r_c(\eta_{1A}) + r_c(\eta_{2A}) - r_c(\eta_{1B}) - r_c(\eta_{2B})] \qquad (24)$$

Finally, the distance between points A and B is calculated as:

$$r=|r|=|d_{AB}+r_{AG}-r_{BG}| \qquad (25)$$

Once again, if two or more cameras are used, one need only correct the image locations for distortion and scale the image locations by the inverse focal length for each camera individually to perform the measurement, just as long as the positions and orientations of the cameras are all expressed in the same global coordinate system.

C. Application of the General Process to Correction of Translation Stage Rotational Errors I have shown four preferred embodiments of my apparatus, where in each case, a single camera will be moved along a substantially straight line. If the motion is a perfect translation, then in Equations (20) and (21), $R_c(\eta_2)$ is equal to $R_c(\eta_1)$, $R_{12}$ is the 3×3 identity matrix, and the direction of perspective displacement $d_g(\eta_2,\eta_1)$, hence $d_{v1}$, remains the same for any $(\eta_2,\eta_1)$. In this case $R_c$ is identified with the product $R_zR_y$, which simply makes use of the fact that the orientation of a vector can always be expressed by at most two angles, since a vector is not changed by a rotation about itself. Finally, with a perfect straight line translation of the camera, Equation (22) reduces to Equation (9).

As an example of the use of the general measurement process to correct for errors of motion, consider the third (EMB) and fourth (EME) preferred embodiments. Assume that the translation stage has rotational errors, which have been characterized with a calibration process, which will be described later. As a result of this calibration, the translation stage rotational error $R(\eta)$ is known in some calibration coordinate system. To simplify the calibration task, I specify that the calibration coordinate system be the same as the global coordinate system, and I explain later how to ensure this. I further specify that the global coordinate system has its x axis along the nominal translation direction, which is simply a matter of definition.

The errors of translation stages are not well specified by their manufacturers. For typical small ball bearing translation stages, a comparison of various manufacturers' specifications is consistent with expected rotational errors of approximately 300 microradians and transverse translational errors of about 3 microns. A moment of thought will convince the reader that with these levels of error, the rotational error will contribute more to the measurement error of the system than will the translation error for any object distance larger than 10 mm. Thus, for measurements of objects which are at distances greater than 10 mm, it is reasonable to correct for only the rotational error of the translation stage. I now show how to do this.

The image point location data are processed in the same manner as has already been described. The position of the camera nodal point can be expressed as:

$$r_c(\eta) = \begin{bmatrix} p(\eta) \\ 0 \\ 0 \end{bmatrix} = p(\eta) \qquad (26)$$

so that the perspective displacement in global coordinates is calculated as:

$$d_g(\eta_2,\eta_1)=r_c(\eta_2)-r_c(\eta_1)=p(\eta_2)-p(\eta_1) \qquad (27)$$

For any position of the camera, the rotational orientation of the camera can be expressed as $$R_c(\eta)=R_{cg}R(\eta) \qquad (28)$$

where $R_{cg}$ is the orientation of the camera with respect to the global coordinate system at some reference position where $R(\eta)$ is defined to be the identity matrix. Both $R_{cg}$ and the rotational error, $R(\eta)$, are determined in the calibration process.

As the next step in measurement processing, then, the relative rotation of the camera between positions P1 and P2 is calculated as:

$$R_{12}(\eta_2,\eta_1)=R_c(\eta_2)R_c^{-1}(\eta_1)=R_{cg}R(\eta_2)R^{-1}(\eta_1)R_{cg}^{-1} \qquad (29)$$

Since the rotation matrices are orthogonal, their inverses are simply calculated as their transposes.

The perspective displacement is then transformed to the camera coordinate system at P1 as:

$$d_{v1}=R_{cg}R(\eta_1)[p(\eta_2)-p(\eta_1)] \qquad (30)$$

and finally the position of the point of interest is calculated by using results (29) and (30) in Equation (22), and distances between points of interest are calculated with Equation (1).

Note that the process I have just outlined implicitly includes the possibility of correction of position transducer errors, given by the calibration curve $p(\eta)$.

If transverse translation errors of the stage are to be corrected, then the calibration process must determine these errors, and the correction data must be incorporated into the general measurement formalism given in the previous section in a similar manner to that shown here for rotational errors.

Calibration

I find it convenient to divide the calibrations of my measurement system into three classes, which I call optical calibration, alignment calibration, and motion calibration.

In optical calibration, the optical properties of the camera when it is considered simply as an image forming system are determined. In alignment calibration, additional properties of the camera which affect the dimensional measurement are determined. Both of these classes of calibration must be accomplished in order to make a measurement with my technique. Optical calibration has been briefly considered in some of the prior art of endoscopic measurements, while alignment calibration is new to my invention.

Motion calibration is not necessarily required to make a measurement, but it may be required in order to make measurements to a specific level of accuracy. Whether this calibration is required or not is determined by the accuracy of the hardware which controls the motion of the camera.

A. Optical Calibration

There is a standard calibration technique known in the field of photogrammetry which is the preferred method of performing the optical calibration of the camera. The technique is discussed, for instance, in the following articles:

"Close-range camera calibration", *Photogrammetric Engineering*, 37(8), 855–866, 1971.

"Accurate linear technique for camera calibration considering lens distortion by solving an eigenvalue problem", *Optical Engineering*, 32(1), 138–149, 1993.

I will outline the equipment and procedure of this calibration here.

The equipment required is a field of calibration target points which are suitable for viewing by the camera to be calibrated. The relative positions of the target points must be known to an accuracy better than that to which the camera is expected to provide measurements. The number of calibration points should be at least twenty, and as many as several hundred points may be desired for very accurate work.

Figure 38:
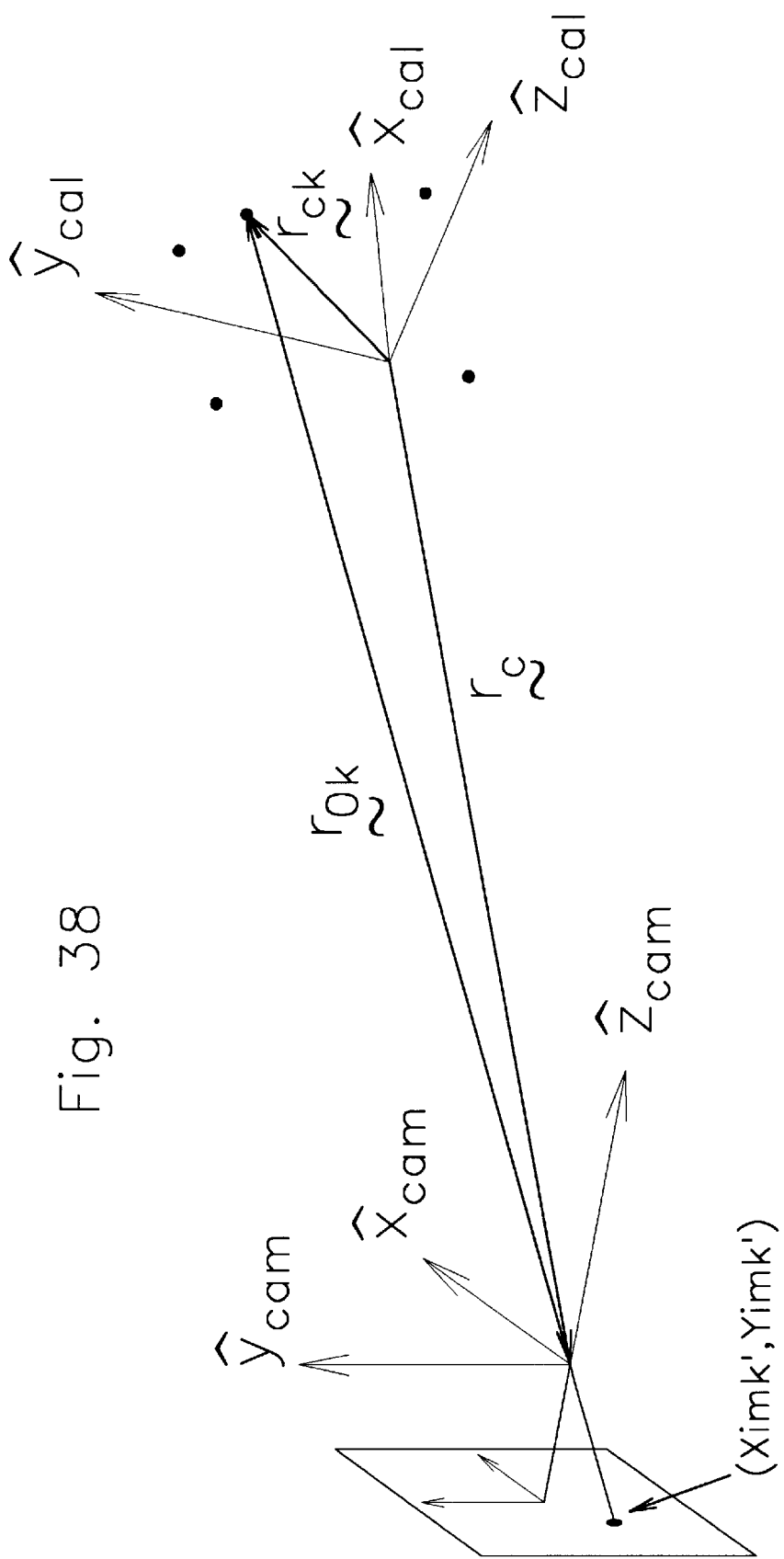
FIG. 38 illustrates a group of calibration target points being viewed with a camera located at an unknown position and orientation.

The calibration target field is viewed with the camera and the image point locations of the target points are determined in the usual way by aligning a video cursor with each point in turn, and commanding the computer to store the measured image point location. The geometry of this process is depicted in FIG. 38.

It is important that the relative alignment of the camera and the calibration target field be such as to ensure that target points are located over a range of distances from the camera. If the target field is restricted to being at a single distance from the camera, the determination of the camera effective focal length will be less accurate than otherwise. Another requirement is that targets be distributed with reasonable uniformity over the whole camera field of view. There is no other requirement for alignment between the camera and the target points.

Assume that k target points have been located in the image plane of the camera. The measured coordinates of the jth image point are denoted as $(x'_{imj}, y'_{imj})$. The following (2×k) matrix of the measured data is then formed:

$$rho' = \begin{bmatrix} x'_{im1} & x'_{im2} & \cdots & x'_{imk} \\ y'_{im1} & y'_{im2} & \cdots & y'_{imk} \end{bmatrix} \quad (31)$$

In FIG. 38 the vector $r_{0k}$, which is the (unknown) position of the kth calibration object point in the camera coordinate system, can be written as:

$$r_{0k} = R_c(\theta_x, \theta_y, \theta_z)[r_{ck} - r_c] \quad (32)$$

where $r_{ck}$ is the known position of the kth calibration point in the calibration target field internal coordinate system (the calibration coordinate system), $r_c$ is the unknown position of the camera's nodal point in the calibration coordinate system, and $R_c$ is the unknown rotation of the camera's coordinate system with respect to the calibration coordinate system. As before, rotation matrix $R_c$ is the product of three individual rotation matrices $R_z(\theta_z)R_y(\theta_y)R_x(\theta_x)$, each of which is a function of a single rotational angle about a single coordinate axis. To be specific, these individual matrices are defined as:

$$R_z(\theta_z) = \begin{bmatrix} \cos\theta_z & \sin\theta_z & 0 \\ -\sin\theta_z & \cos\theta_z & 0 \\ 0 & 0 & 1 \end{bmatrix} \quad (33)$$

$$R_y(\theta_y) = \begin{bmatrix} \cos\theta_y & 0 & -\sin\theta_y \\ 0 & 1 & 0 \\ \sin\theta_y & 0 & \cos\theta_y \end{bmatrix}$$

$$R_x(\theta_x) = \begin{bmatrix} 1 & 0 & 0 \\ 0 & \cos\theta_x & \sin\theta_x \\ 0 & -\sin\theta_x & \cos\theta_x \end{bmatrix}$$

The kth ideal image position vector is defined as:

$$rho_{imk} = \frac{-i}{r_{0k}(3)} \begin{bmatrix} r_{0k}(1) \\ r_{0k}(2) \end{bmatrix} \quad (34)$$

where i is the equivalent focal length of the camera. The (2×k) ideal image position matrix is defined as:

$$rho_{im} = [rho_{im1} rho_{im2} \cdots rho_{imk}] \quad (35)$$

Similarly, the image point coordinate error for the kth point is defined as:

$$rho_{Dk} = \begin{bmatrix} f_{Dx}(rho'_k) \\ f_{Dy}(rho'_k) \end{bmatrix} \quad (36)$$

and the (2×k) image coordinate error matrix is:

$$rho_D = [rho_{D1} rh_{D2} \cdots rho_{Dk}] \quad (37)$$

The error functions $f_{Dx}$ and $f_{Dy}$ define the image location errors which are to be considered in the camera calibration. While a number of different error functions are used in the art, I recommend the following fairly general expression when the camera is a borescope, since the distortion of a borescope is so large:

$$f_{Dx}(rho'_k) = x_0 + (a_1 + a_2|rho'_k|^2 + a_3|rho'_k|^4)x'_{imk} + a_4(|rho'_k|^2 + 2x'_{imk}^2) + 2a_5x'_{imk}y'_{imk}$$

$$f_{Dy}(rho'_k) = y_0 + (a_6 + a_2|rho'_k|^2 + a_3|rho'_k|^4)y'_{imk} + a_5(|rho'_k|^2 + 2y'_{imk}^2) + 2a_4x'_{imk}y'_{imk} \quad (38)$$

where, of course, $|rho'_k|^2 = x'_{imk}{}^2 + y'_{imk}{}^2$.

The following equation expresses the relationship between the measured image point positions, and the ideal image point positions:

$$rho' = rho_{im} + rho_D \quad (39)$$

Using the quantities defined above, Equation (39) represents 2k equations in 15 unknowns. The unknowns are the three angles of the camera rotation $\theta_z, \theta_y, \theta_x$, the three components of the camera location $x_c, y_c, z_c$, the equivalent focal length, i, and the eight parameters of image position error $x_0, y_0, a_1, \ldots a_6$. In order to obtain a solution, one must have $k \geq 8$. As I have stated above, one wants to use many more points than this to obtain the most accurate results.

As I previously stated, I call all eight of the image position error parameters "distortion", but only some of them relate to the optical field aberration which is usually referred to as distortion. The parameters $x_0$ and $y_0$ represent the difference between the center of the image measurement coordinate system and the position of the optical axis of the camera.

Parameters $a_1$ and $a_6$ represent different scale factors in the x and y directions. Parameters $a_2$ and $a_3$ represent the standard axially symmetric optical Seidel aberration called distortion. Parameters $a_4$ and $a_5$ represent possible non-symmetrical distortion due to tilt of the camera focal plane and decentration of the elements in lenses.

The overdetermined set of Equations (39) has no exact solution in general, nor would one want an exact solution if it were available, since the experimental data are subject to error. Consequently, the calibration data processing determines best fit values for each of the 15 parameters by minimizing the length of an error vector. This is done by an iterative numerical process called non-linear least squares optimization.

Specific algorithms to implement non-linear least squares optimization are well known in the art. They are discussed, for instance, in the book *Numerical Recipes* by William H. Press, et. al., published by Cambridge University Press, 1st Ed. 1986. This book provides not only the theory behind the numerical techniques, but also working source code in Fortran that is suitable for use in an application program. A second edition of this book is available with working source code in C. Another book which is helpful is R. Fletcher, "*Practical Methods of Optimization, Vol. 1—Unconstrained Optimization*, John Wiley and Sons, 1980.

A second option for implementation of the non-linear least squares optimization is to use one of the available "canned" numerical software packages such as that from Numerical Algorithms Group, Inc. of Downers Grove, Ill. Such a package can be licensed and incorporated into application programs, such as the program which controls computer 228. A third option is to use one of the proprietary high level mathematical analysis languages such as MATLAB®, from The Math Works, Inc. of Natick, Mass. These languages have high level operations which implement powerful optimization routines, and also have available compilers, which can produce portable C language code from the very high level source code. This portable C code can then be recompiled for the target system, computer 228.

The optimization process begins with approximate values for the fifteen unknowns and adjusts these iteratively to minimize the quantity:

$$Q = |rho' - rho_{im} - rho_D|^2 \qquad (40)$$

The ideal value of Q is zero; the optimization process attempts to find the smallest possible value.

The starting values for the unknowns are not critical in general, but the iterative process will converge faster if the starting values are not far away from the true values. Thus, it makes sense to perform the optical calibration with a specific alignment of the camera with respect to the calibration target array, so that the camera alignment parameters are approximately already known. It is also a good idea to use any available information about the approximate camera focal length and the distortion parameters in the starting values.

The first six calibration parameters, $\{\theta_z, \theta_y, \theta_x, x_c, y_c, z_c\}$, refer to the position and alignment of the camera as a whole. The other nine parameters are subsequently used to correct measured image point position data to ideal image point position data by:

$$rho_{im} = rho' - rho_D = \begin{bmatrix} x'_{im} \\ y'_{im} \end{bmatrix} - \begin{bmatrix} f_{Dz}(rho') \\ f_{Dy}(rho') \end{bmatrix} \qquad (41)$$

which is another way of expressing Equations (2). After the image point positions are corrected, then the visual location vector used in the measurement Equations (9) and (22) is defined as:

$$a_v = -\frac{1}{i}\begin{bmatrix} rho_{im} \\ -i \end{bmatrix} \qquad (42)$$

which is a more compact way of expressing Equations (3) and (4).

B. Alignment Calibration

Recall that in the perspective measurement process the object of interest is viewed from two points in space, which are called P1 and P2. Recall further that the vector connecting the camera nodal point at viewing position P1 to the camera nodal point at viewing position P2 is defined as the perspective displacement d. The essence of alignment calibration is to determine the orientation of the perspective displacement, d, with respect to the camera's internal coordinate system. Once d is known in the camera coordinate system, then the position of object points can be calculated using either Equation (9) or Equation (22), as appropriate.

Since the camera's position and orientation are estimated during the optical calibration procedure given in the previous sub-section, these data can be used to determine the alignment of d in the camera's coordinate system if that calibration is done twice, from two different viewing positions. In fact, these are exactly the calibration data that are needed to implement the perspective measurement for a general motion of the camera which was outlined in Equations (19) through (22). All one need do is to carry out the optical calibration procedure at the two measurement camera positions with a fixed calibration target array. This is, in fact, what is done in the photogrammetry field, and is what can be done with a general motion embodiment of my invention.

In my preferred embodiments, there is considerable information is available about the motion of the camera that would not be used if one were to proceed as I have just suggested. For instance, if the translation stage is accurate, then that means that the orientation of the camera does not change between P1 and P2, and, in fact, it doesn't change for any position of the camera along its path. For those embodiments where the geometry of the camera path is accurately known, such as the preferred embodiments, one can determine the alignment of d in the camera's coordinate system at one point on the path and thereby know it for any point on the path.

In addition, the perspective baseline |d| may be especially accurately known, depending on the performance of the position transducer, and how accurately it is aligned with the motion of the translation stage. As a third possibility, it is possible to accurately measure rotational errors in the translation stage, as long as the motion of the stage is repeatable. All of this information can be taken into account in order to determine a better estimate of the orientation of d in the camera coordinate system, and thus, to achieve a more accurate measurement.

As a first example of alignment calibration, consider that two optical calibrations have been done at two positions along the camera path, as discussed above. The calibration data available for the camera position and orientation are then $r_c(\eta_2)$, $r_c(\eta_1)$, $R_c(\eta_2)$, and $R_c(\eta_1)$. Also consider that it is known that the camera moves along an accurate straight line.

The camera orientation in the calibration coordinate system is then estimated as:

$$R_c = \frac{1}{2}(R_c(\eta_2) + R_c(\eta_1)) \qquad (43)$$

Note that the difference between $R_c(\eta_2)$ and $R_c(\eta_1)$ gives an indication of the precision of this calibration.

The perspective displacement in calibration coordinates is estimated as:

$$d_g(\eta_2,\eta_1) = r_c(\eta_2) - r_c(\eta_1) \qquad (44)$$

and in camera coordinates it is estimated as:

$$d_{v1} = R_c d_g(\eta_2,\eta_1) \qquad (45)$$

Because there is no rotation of the camera, it is known that the orientation of this vector does not change with camera position.

In Equations (5) and (6) the measurement process was defined in terms of rotation matrices such that:

$$d_{v1} = R_z(\theta_z)R_y(\theta_y)\begin{bmatrix} d \\ 0 \\ 0 \end{bmatrix} \qquad (46)$$

where $d=|d_{v1}|$. Writing the measured components of $d_{v1}$ from Equation (45) as $(dv_x, dv_y, dv_z)$ one writes the following equation, using definitions (33):

$$R_z(\theta_z)R_y(\theta_y)\begin{bmatrix} d \\ 0 \\ 0 \end{bmatrix} = d\begin{bmatrix} \cos\theta_y\cos\theta_z \\ -\cos\theta_y\sin\theta_z \\ \sin\theta_y \end{bmatrix} = \begin{bmatrix} dv_x \\ dv_y \\ dv_z \end{bmatrix} \qquad (47)$$

Equation (47) can be solved for the rotation angles as:

$$\theta_y = \arcsin\left(\frac{dv_z}{d}\right) \qquad (48)$$

$$\theta_z = \arcsin\left(\frac{dv_y}{\sqrt{dv_x^2 + dv_y^2}}\right)$$

Thus, the final step of this alignment calibration process is to determine the two angles $\theta_y$ and $\theta_z$ with Equation (48). During the measurement process, these angles are used in Equation (6).

As a second example of alignment calibration, consider that an optical calibration has been previously done, and now it is desired to do an alignment calibration. This would be the normal situation with the first and second preferred embodiments, since the alignment of the camera with respect to its translation may change whenever the borescope is clamped to the BPA. Consider also that the motion of the camera is known to be constrained to be along an accurate straight line (that is, any errors in the motion are known to be smaller than the corresponding level of error required of the measurement).

Once again, a calibration target array is viewed from two positions of the camera along its path of motion. According to FIG. 38 and Equation (32), one can write:

$$r_{0k1} = R_c[r_{ck} - r_c(\eta_1)] r_{0k2} = R_c[r_{ck} - r_c(\eta_2)] \qquad (49)$$

The visual location vectors, which are calculated from the distortion corrected image position data according to Equation (42), can also be written as:

$$a_{vk1} = \frac{r_{0k1}}{z_{k1}} = r_{0k1}u_{k1} \qquad (50)$$

$$a_{vk2} = \frac{r_{0k2}}{z_{k2}} = r_{0k2}u_{k2}$$

in terms of the object point coordinates. One corrects the distortion of the measured data using Equation (41) with the distortion parameters obtained in the previous optical calibration.

Define the following quantities where it is assumed that k calibration points are used:

$$A_{v1} = [a_{v11} \; a_{v21} \; \cdots \; a_{vk1}] \qquad (51)$$

$$A_{v2} = [a_{v12} \; a_{v22} \; \cdots \; a_{vk2}]$$

$$r_{cal} = [r_{c1} \; r_{c2} \; \cdots \; r_{ck}]$$

$$1_k = [1 \; 1 \; \cdots \; 1] \quad (k \text{ components})$$

$$U_1 = \begin{bmatrix} u_{11} & 0 & \cdots & \cdots & 0 \\ 0 & u_{21} & 0 & \cdots & 0 \\ 0 & 0 & \ddots & \cdots & 0 \\ \vdots & \vdots & \vdots & \ddots & \vdots \\ 0 & 0 & 0 & \cdots & u_{k1} \end{bmatrix}$$

$$U_2 = \begin{bmatrix} u_{12} & 0 & \cdots & \cdots & 0 \\ 0 & u_{22} & 0 & \cdots & 0 \\ 0 & 0 & \ddots & \cdots & 0 \\ \vdots & \vdots & \vdots & \ddots & \vdots \\ 0 & 0 & 0 & \cdots & u_{k2} \end{bmatrix}$$

Then Equations (49) can then be written as:

$$A_{v1} = R_c[r_{cal} - r_c(\eta_1)1_k]U_1 \; A_{v2} = R_c[r_{cal} - r_c(\eta_2)1_k]U_2 \qquad (52)$$

and Equations (52) can be combined into:

$$[A_{v1} A_{v2}] = R_c[[r_{cal} r_{cal}] - [r_c(\eta_1)1_k r_c(\eta_2)1_k]]U_{12} \qquad (53)$$

where $U_{12}$ is:

$$U_{12} = \begin{bmatrix} U_1 & 0 \\ 0 & U_2 \end{bmatrix} \qquad (54)$$

Equation (53) represents 6k equations in 2k+9 unknowns, thus, they can be solved for $k \geq 3$. The unknowns are $U_{12}$ (2k unknowns) and $R_c$, $r_c(\eta_1)$, and $r_c(\eta_2)$, which each contain 3 unknowns. Equation (53) makes full use of the fact that $R_c$ is constant; and is thus a more efficient way of estimating the nine unknowns of interest for the alignment calibration than was the previous case.

Equations (53) are solved by a similar nonlinear least squares process as was used for Equation (39). Once the camera positions and orientation are estimated, one simply uses Equations (46) through (48) to determine the alignment angles, which are used during the measurement process.

To improve the efficiency even further, in the case where $d=|d|$ is considered accurately known, Equation (53) can be solved by a constrained least squares optimization rather than the unconstrained optimization I have so far discussed.

Such numerical procedures are discussed in R. Fletcher, "Practical Methods of Optimization, Vol. 2—Constrained Optimization, John Wiley and Sons, 1980. Most, if not all of the "canned" numerical software offers routines for constrained optimization as well as unconstrained optimization, and so do the high level mathematical analysis languages.

In this case, the constraint is:

$$|r_c(\eta_2)-r_c(\eta_1)|-d=0 \tag{55}$$

It is possible to use an inequality constraint as well, so that if it is known that there is a certain level of uncertainty in the determination of d, then Equation (55) could be replaced with:

$$|r_c(\eta_2)-r_c(\eta_1)|-d \leq \epsilon_d \tag{56}$$

where $\epsilon_d$ is the known level of uncertainty in d.

As a third example of alignment calibration, I now consider the case where there are rotational errors in the motion of the camera in my third and fourth preferred embodiments. I have already explained how to make the measurement in this case, in the sub-section entitled "Application of the General Process to the Correction of Translation Stage Rotational Errors". In motion calibration subsection C. below, I will explain how to determine the rotational errors. Here, I explain how to take these errors into account during the alignment calibration.

For alignment calibration of the EMB or EME with a known stage rotational error, it is necessary to determine the static alignment of the camera with respect to the translation direction in the presence of this error. Recall that at any point along the camera's path:

$$R_c(\eta)=R_{cg}R(\eta) \tag{28}$$

where now $R(\eta)$ is known from the motion calibration process.

Once again, a calibration target array is viewed from two positions of the camera along its path of motion. According to FIG. 38 and Equation (32), one can write:

$$r_{0k1}=R_{cg}R(\eta_1)[r_{ck}-r_c(\eta_1)]r_{0k2}=R_{cg}R(\eta)[r_{ck}-r_c(\eta_2)] \tag{57}$$

These are extended just Equations (49) were to obtain:

$$A_{v1}=R_{cg}R(\eta_1)[r_{cal}-r_c(\eta_1)1_k]U_1 A_{v2}=R_{cg}R(\eta_2)[r_{cal}-r_c(\eta_2)1_k]U_2 \tag{58}$$

and Equations (58) can be combined into:

$$[A_{v1}A_{v2}]=R_{cg}[[R(\eta_1)r_{ca}R(\eta_2)r_{cal}]-[R(\eta_1)r_c(\eta_1)1_k R(\eta_2)r_c(\eta_2)1_k]]U_{12} \tag{59}$$

which is the same optimization problem as was Equation (53). This is handled exactly the same way to estimate $R_{cg}$, $r_c(\eta_1)$, and $r_c(\eta_2)$. With $R_{cg}$, the rotation of the camera at any point in its path is known as $R_c(\eta)$ from Equation (28). I have assumed that the rotation of the stage does not affect the offset of the stage, so that the measurement in this case is accomplished with Equations (26) through (30), Equation (22), and finally Equation (1).

C. Motion Calibration

For the third alignment calibration case above, the rotational errors of the translation stage must have been previously determined in a motion calibration procedure. Preferably, this motion calibration is done at the factory, for a subassembly of the EMB or EME. These calibration data are then incorporated into the software of the complete measurement scope that is constructed using the particular subassembly in question.

The small rotation errors of a linear translation stage can be conveniently measured using a pair of electronic tooling autocollimators as depicted in FIG. 39. Each of these autocollimators is internally aligned so that its optical axis is accurately parallel to the mechanical axis of its precision ground cylindrical housing. Such instruments are available from, for example, Davidson Optronics of West Covina, Calif. or Micro-Radian Instruments of San Marcos, Calif.

In FIG. 39, two collimator V-blocks 602 are mounted to a flat stage calibration baseplate 600. The two precision machined V-blocks 602 are located with precision pins so that their axes accurately perpendicular, to normal machining tolerances. The two V-blocks 602 thus define the directions of a Cartesian coordinate system, which is defined as indicated on FIG. 39.

An EMB Subassembly V-block 606 is also mounted to baseplate 600 and located with pins, so that its axis is accurately parallel to the x axis defined by V-blocks 602. Also installed on baseplate 600 is actuator mounting block 608.

The autocollimators 604 are installed into their respective V-blocks and are both rotated about their respective axes so that their measurement y axes are oriented accurately perpendicular to the mounting plate.

With the autocollimators installed and aligned, EMB translation stage subassembly 550 is placed into V-block 606. An enlarged view of a portion of this subassembly is shown in Figure 39A. Subassembly 550 consists of distal baseplate 514 (see FIGS. 23–25) to which is mounted translation stage 180, and transducer mounting bracket 367. Translation stage 180 is composed of fixed base 182 and moving table 184. Transducer 360 is mounted in bracket 367, and its operating rod 361 is mounted to transducer attachment bracket 369. Bracket 369 is in turn mounted to moving table 184.

The procedure given here assumes that translation stage 180 has been mounted to distal baseplate 514 so that the axis of translation is oriented parallel to the cylindrical axis of the distal baseplate. This alignment need only be accurate to normal machining tolerances, as I will discuss later. If the specific design of the hardware is different than I show for the preferred embodiment, it is necessary to use some other appropriate method of ensuring that the axis of translation of stage 180 is oriented parallel to the x axis defined by the calibration hardware, and that this orientation is accurate to normal machining tolerances.

Subassembly 550 is rotated about its axis to make the top surface of distal baseplate 514 nominally parallel to baseplate 600 and then it is clamped into position. For purposes of clarity, the clamp is not shown in FIG. 39.

Stage operating arm 614 is then attached to moving table 184. Actuator 610 is installed in mounting block 608, and actuator operating rod 612 is attached to operating arm 614. Thus, the stage can now be moved back and forth over its range of travel and a function of its position, $\eta(p)$, can be read at the output of position transducer 360.

Stage 180 is moved to the mid range of its travel by the use of actuator 610. Mirror platform 618 is then attached to moving table 184. Mirror platform 618 has mounted to it two mirror mounts 620, which in turn hold a longitudinal mirror 622 and a transverse mirror 624.

Mirror mounts 620 are then adjusted to tilt each of the mirrors in two angles so as to center the return beams in autocollimators 604 as determined by the angular readouts of the autocollimators (not shown).

Translation stage 180 is then moved to one end of its travel using actuator 610. Calibration data are then recorded by moving stage 180 toward the other end of its travel range in a series of suitably small steps in distance. The output of position transducer 360, $\eta$, is recorded at each step position, as are the angular readings of the autocollimators. Note that one need not be concerned with the actual distance stage 180 is moved between steps, unless one is also intending to calibrate transducer 360 at the same time.

The readings from the autocollimator viewing along the x axis will be $(2\theta_y, 2\theta_z)$ where the positive direction for the angles is counter-clockwise when the view is along the axis from positive coordinates toward the origin (i.e., the right hand rule). The readings from the autocollimator viewing along the z axis will be $(2\theta_y, -2\theta_x)$. The rotational error of the stage at any point can be expressed as:

$$R(\eta) = R_z(\theta_z) R_y(\theta_y) R_x(\theta_z) \tag{60}$$

It is more efficient to record and store the three angles $\theta_z(\eta)$, $\theta_y(\eta)$, $\theta_x(\eta)$ and calculate $R(\eta)$ whenever it is needed. When the calibration data are used in a measurement procedure, it will be necessary to interpolate between the stored values of $\eta$ to estimate the rotation angles at the actual values of $\eta$ used in the particular measurement. Such interpolation procedures are well known in the art.

An error analysis shows that the angles measured during this calibration process will be a mixture of the components of the true rotational angles, if the calibration geometry is not perfectly aligned with the translation direction of the stage. However, the level of the mixed components is proportional to the error in the geometry, and thus will be small. For instance, if the angles determining the calibration geometry were all in error by three degrees (which is much larger than one would expect, using normal machining tolerances), the measured stage rotation angles would be 10% in error in the worst case. Since it is unlikely that the repeatability of a translation stage will be much more than ten times better than its absolute angular accuracy, this level of error is appropriate for calibration of the stage angular errors. Thus, use of a calibration geometry which is determined by precision machining is adequate to perform the calibration measurements.

Theory of Operation

A. Introduction

After deriving a simple theory of the perspective technique for determining the location of a point, I discuss the advisability of use of the "guide line" which is taught by Nonami and Sonobe (U.S. Pat. No. 4,935,810). I then generalize the theory to an arbitrary measurement geometry, and make stronger statements about the desirability of the guide line technique.

Throughout this discussion of the theory, the use of a single moving camera to make the measurement is assumed. The extension to the use of two cameras is straightforward, and these results have already been discussed.

The theory of the mode 2 measurement has already been given in the sub-section entitled "The General Perspective Measurement Process".

B. Perspective measurement with a simple geometry

Figure 40:
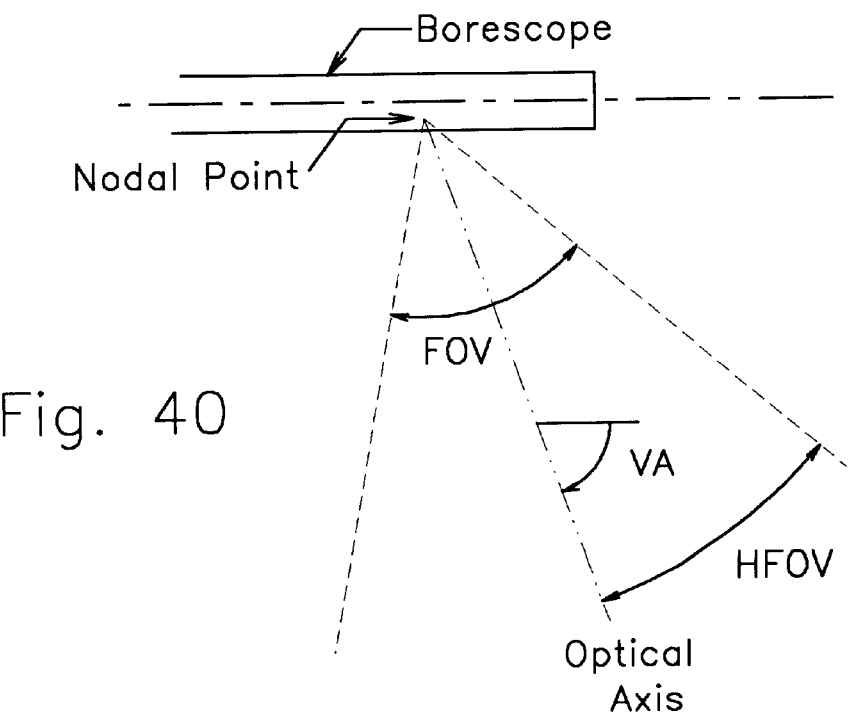
FIG. 40 shows the definitions of various angles related to a rigid borescope.

The field of view of a borescope is defined by the nodal point of its optical system and a cone that has its apex there. This is shown in FIG. 40. The "nodal point" of an optical system is that point on the optical axis of the system for which rays incident at the point are undeviated.

FIG. 40 is drawn in the plane containing both the centerline of the borescope and the extension of the borescope optical axis into the field of view. The apex angle of the field of view cone is called FOV, half that angle is denoted as HFOV, and the "viewing angle" of the borescope with respect to the centerline of the scope is denoted as VA. Angle VA is defined to be positive for rotation away from the borescope centerline, to match standard industry practice. In the following, I will also use the acronym "FOV" to refer to the words "field of view".

Figure 41:
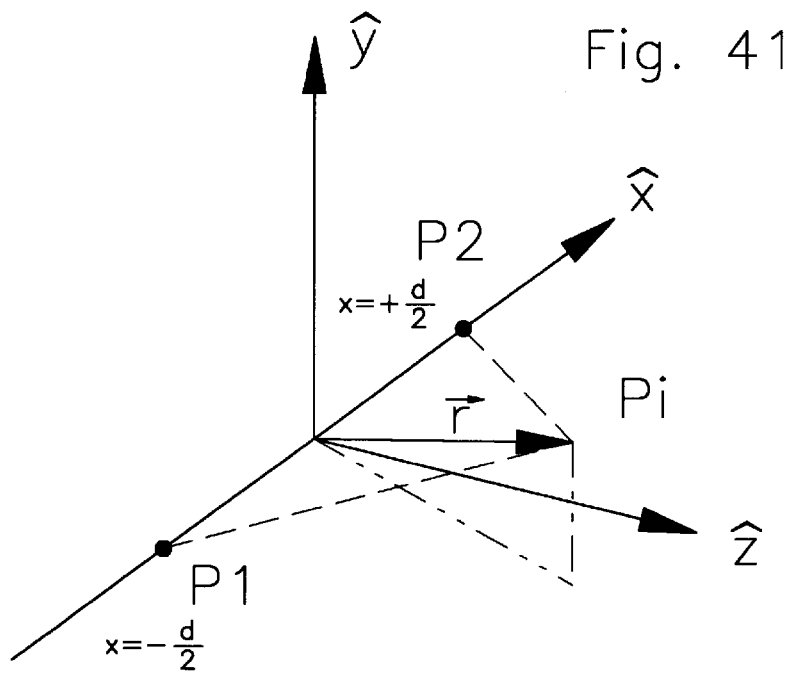
FIG. 41 depicts the change in perspective when viewing a point in space from two different positions.

The change in perspective in viewing a point in space from two different positions is depicted in FIG. 41. A right handed global Cartesian coordinate system is defined by the unit vectors $\hat{x}$, $\hat{y}$, and $\hat{z}$. A particular point of interest, $P_i$, at $\vec{r} = x\,\hat{x} + y\,\hat{y} + z\,\hat{z}$, is viewed first from position P1, then from position P2. The coordinate system has been defined so that these viewing positions are located on the x axis, equally spaced on either side of the coordinate origin. I call the distance d between the viewing positions the perspective baseline, and I call the vector $\vec{d} = d\,\hat{x}$ the perspective displacement.

Viewing coordinate systems are set up at P1 and P2, and these coordinate systems are taken to be aligned parallel to the global coordinates defined in FIG. 41.

Figure 42:
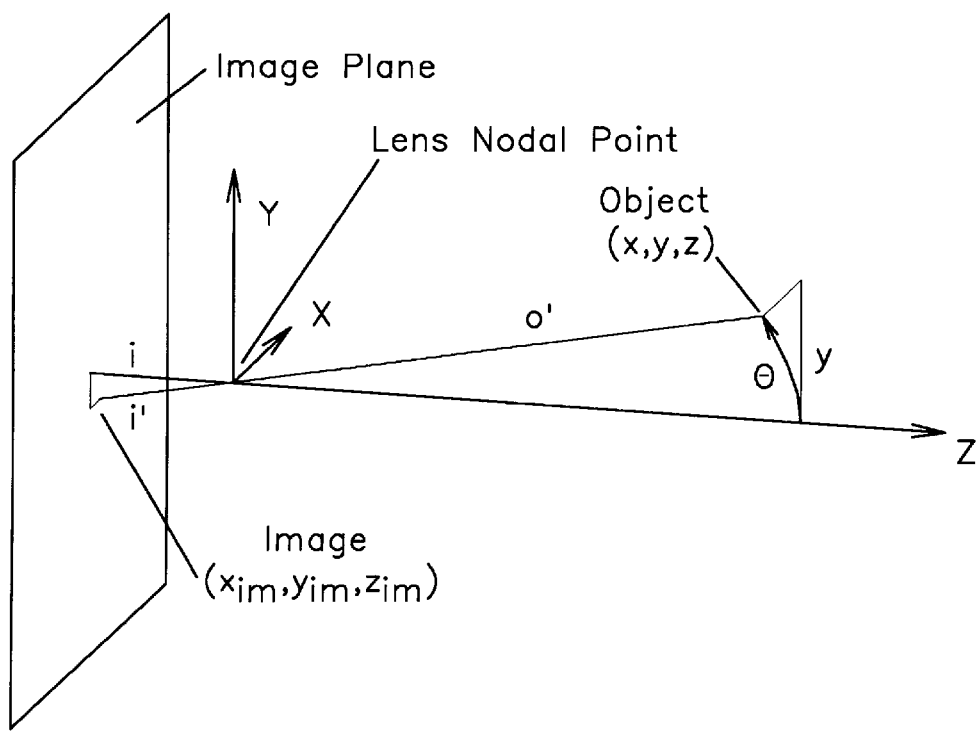
FIG. 42 depicts the imaging of a point in space with a camera.

The point of interest is imaged onto the flat focal plane of a camera. FIG. 42 shows schematically the imaging of a point in space with a camera. Here, I represent the effect of the camera lens by considering the lens as a paraxial thin lens. According to paraxial optics, rays that strike the nodal point of the lens pass through it undeviated. It is important to realize that any imaging optical system, including that of a video borescope, can be represented as a camera as shown in FIG. 42.

In FIG. 42 an image plane is set up behind the nodal point, with the distance from the plane to the nodal point being denoted as i. This distance is measured along a perpendicular to the image plane. The nodal point is taken as the origin of a Cartesian coordinate system, where the z axis is defined as that perpendicular to the image plane that passes through the nodal point.

For an object point at (x, y, z) one can write these coordinates in standard spherical polar coordinates about the nodal point as:

$$x = o'\sin\theta\cos\phi \quad y = o'\sin\theta\sin\phi \quad z = o'\cos\phi \tag{61}$$

where o' is the distance from the object point to the nodal point, and the polar angle $\theta$ is shown in FIG. 42.

By the properties of the nodal point, the angles will remain the same and one can write the image point location as:

$$x_{im} = -i'\sin\theta\cos\phi \quad y_{im} = -i'\sin\theta\sin\phi \quad z_{im} = -i \tag{62}$$

But $i = i'\cos\theta$ so that:

$$x_{im} = -\frac{i\sin\theta\cos\phi}{\cos\theta} = -\frac{ix}{o'\cos\theta} = -\frac{ix}{z} \tag{63}$$

$$y_{im} = -\frac{i\sin\theta\sin\phi}{\cos\theta} = -\frac{iy}{o'\cos\theta} = -\frac{iy}{z} \tag{64}$$

That is, the coordinates of the image point $(x_{im}, y_{im})$, are directly proportional to the transverse coordinates of the object point.

When considering the performance of a real optical system, as opposed to a paraxial model, the image of an object point will be blurred by what are called point aberrations and it will be displaced by what are called field aberrations. I define the location of the image point to be the location of the centroid of the blur spot, and I refer to the extent to which Equations (63) and (64) do not hold for the image point centroid as the distortion of the optical system. Clearly, consideration of the distortion of the optical system is important for making accurate measurements, and this was recognized in some of the prior art. I have previously shown how to determine the distortion and how to take it into account.

Considering the view from position P1 in FIG. 41, one may write:

$$x_{im1} = -\frac{ix_{v1}}{z_{v1}}; \quad y_{im1} = -\frac{iy_{v1}}{z_{v1}} \tag{65}$$

where $(x_{v1}, y_{v1}, z_{v1})$ are the coordinates of the point of interest in the viewing coordinate system at P1. Similar expressions in terms of $(x_{v2}, y_{v2}, z_{v2})$ hold for the view at P2. Using the facts that $x_{v1}=x+d/2$, $x_{v2}=x-d/2$, $y_{v1}=y_{v2}=y$, and $z_{v1}=z_{v2}=z$, the solution of the four equations for the position of the point $P_i$ in global coordinates is:

$$z = \frac{-id}{x_{im1} - x_{im2}} \tag{66}$$

$$x = \left(\frac{-z}{2i}\right)(x_{im1} + x_{im2})$$

$$y = \left(\frac{-z}{i}\right)(y_{im1}) = \left(\frac{-z}{i}\right)(y_{im2})$$

To make a measurement of the true, three dimensional distance between two points in space, one has simply to measure the three dimensional position (x, y, z) of each point according to (66) and then to calculate the distance between them by the well known Pythagorean formula (Equation (1)).

C. The advisability of the use of a "guide line"

In Equations (66), there is a redundant pair of equations because with the four measurements there are four equations, but there are only three unknowns. Referring again to FIG. 41, it is clear that no matter how the coordinate system is defined, the three points P1, P2 and $P_i$ are confined to a plane. This is the source of the redundancy. Nonami and Sonobe (U.S. Pat. No. 4,935,810) use this redundancy to create the idea of a "guide line". Their "guide line" idea states that once the apparent y position of point $P_i$ is measured at P1, then the thing to do is to require the measurement at point P2 to have the same value. That is, they enforce $y_{im2}=y_{im1}$. But this assumes that there are no errors. For instance, this assumes that there is no error in the measurement of $y_{im1}$, and that there are no errors in the relative orientations, magnifications, or distortions of the cameras between the views at P1 and P2. But in real life there will be such errors, and enforcing $y_{im2}=y_{im1}$ not only throws away any information that might have been provided by the measurement of y at P2, but in some cases can actually cause an error that would not otherwise occur.

As a general principle, in the presence of errors, using all of the information available is important to achieve the best measurement results. Heuristically, then, one would think that it would be appropriate to average the two measurements of y, rather than simply to discard one of them. I will discuss this issue further below.

D. Introduction to the General Theory

The simple theory assumes that the viewing camera optical axis is oriented perpendicular to the perspective displacement, that is, along the z axis in FIG. 41. It also assumes that the horizontal and vertical axes of the camera are oriented along the x and y directions. Clearly, in view of FIG. 40, these assumptions are not adequate for my system, because in the first two embodiments of my invention I propose to use any substantially side-looking borescope without any specific alignment between the optical axis and the perspective displacement. I also intend that my third and fourth embodiments have a similar flexibility in camera alignment.

The assumptions of the basic theory are also inadequate when considering any practical prior art system, that is any system which is not assumed to have been built to geometric perfection.

I begin by assuming that the motion of the camera between the two viewing positions consists of a perfect translation, but that there is no special alignment between that translation and the optical axes of the camera. As I will show, this generalization also leads to strong conclusions about how best to use the available measurement data.

I then generalize the theory further to allow rotation as well as translation of the camera in the motion between the two viewing positions. This extension allows the measurement to be performed with any motion of the camera, and it also allows the correction of motion errors, as I described previously.

FIG. 43 shows a generalized perspective measurement situation. Here, two viewing coordinate systems are set up, each of which is determined by the x and y axes of the camera focal plane, and their mutual perpendicular $\hat{z}=\hat{x}\times\hat{y}$.

In FIG. 43 a first coordinate system has its origin at the first observation point, P1, and a second coordinate system has its origin at the second observation point, P2. Because there may be a rotation of the camera in moving between P1 and P2, the coordinate axes at P1 and P2 are not parallel, in general. These coordinate systems are denoted by the subscripts 1 and 2. That is, the P1 coordinates of a point are expressed as $(x_1, y_1, z_1)$ while the coordinates of the same point, as expressed in the P2 system, are $(x_2, y_2, z_2)$. The P2 coordinate system has its originated in the P1 system.

To accomplish the perspective measurement, the arbitrary point $P_i$ is viewed first in the P1 coordinate system, then in the P2 coordinate system.

E. The case of pure translation

Assume now that there is no rotation of the camera in the translation between P1 and P2. In this case, the coordinate axes of the two systems are parallel. The partial generalization here is that the perspective displacement between P1 and P2, d, can be at any arbitrary orientation with respect to the coordinate axes.

In the sub-section B. above, I derived the following relationships between the camera image plane coordinates and the corresponding object point coordinates:

$$x_{im} = -\frac{ix}{z}; \quad y_{im} = -\frac{iy}{z} \tag{67}$$

where i is the distance from the nodal point of the optical system to the image plane. Similar equations hold for the observations at both camera positions. These image point data can be written in vector form as:

$$r_{im} = \begin{bmatrix} x_{im} \\ y_{im} \\ z_{im} \end{bmatrix} = \begin{bmatrix} x_{im} \\ y_{im} \\ -i \end{bmatrix} = -\frac{i}{z}\begin{bmatrix} x \\ y \\ z \end{bmatrix} = -\frac{i}{z}r \tag{68}$$

-continued $$r = -\frac{z}{i} r_{im} = z \begin{bmatrix} -\frac{x_{im}}{i} \\ -\frac{y_{im}}{i} \\ 1 \end{bmatrix} = z a_v \qquad (69)$$

The vector $a_v$, which I call the visual location vector, contains the image point location data for the measurement of the apparent location of a point $P_i$ from a given viewing position. These data, of course, are assumed to have been corrected for distortion as was previously explained in the section entitled "Calibration". The distance, z, is unknown. When one measures the apparent locations of $P_i$ from two viewing positions, separated by a vector d, one has two vector equations:

$$r_1 = r_2 + d = z_2 a_{v2} + d \quad r_1 = z_1 a_{v1} \qquad (70)$$

where $r_1$ is the location of a point as expressed in the coordinate system which has its origin at P1, and $r_2$ is the location of the same point as expressed in the coordinate system tied to P2.

Expressions (70) represent 6 equations 4 unknowns. The four unknowns are the three components of $r_1$ (or $r_2$) and $z_2$ (or $z_1$).

Subtracting the two Equations (70), I obtain:

$$z_1 a_{v1} - z_2 a_{v2} = d \qquad (71)$$

which can be written as:

$$[a_{v1} \quad -a_{v2}] \begin{bmatrix} z_1 \\ z_2 \end{bmatrix} = d \qquad (72)$$

Expression (72) represents three equations in two unknowns. When there are more equations than unknowns, the system of equations is called over-determined, and there is in general no exact solution. However, because the coefficients of the equations are experimentally determined quantities that contain noise, one wouldn't want an exact solution, even if one happened to be available. What one wants is a solution that "best fits" the data in some sense. The standard criterion for "best" is that the sum of the squares of the deviations of the solution from the measured data is minimized. This is the so-called least squares solution.

I have found a convenient reference for the mathematics related to this subject to be *Optimal Control and Estimation*, by Robert F. Stengel, republished by Dover in 1994. This same book was originally published by Wiley in 1986 as *Stochastic Optimal Control*.

The least squares solution of the over determined system of Equations (72) can be simply expressed by introducing the left pseudo-inverse of the data matrix:

$$\begin{bmatrix} z_1 \\ z_2 \end{bmatrix} = [a_{v1} \quad -a_{v2}]^{LI} d \qquad (73)$$

Adding the two Equations (70), I get:

$$2r_1 - d = [a_{v1} \quad a_{v2}] \begin{bmatrix} z_1 \\ z_2 \end{bmatrix} \qquad (74)$$

Substituting (73) into (74) I find:

$$r_1 = \frac{1}{2}[[a_{v1} \quad a_{v2}][a_{v1} \quad -a_{v2}]^{LI} + I_3] d \qquad (75)$$

where $I_3$ is the identity matrix of dimension 3. Equation (75) gives the least squares solution to the location of the point of interest, $P_i$, as expressed in the coordinate system at viewing position P1, for the visual location vectors $a_{v1}$ and $a_{v2}$ measured at viewing positions P1 and P2 respectively.

To aid in the comparison of expressions (75) to the simple theory result (66), I introduce an auxiliary coordinate system into expression (75). Recall that (66) refers to a coordinate system which is defined such that the origin lies exactly half way between the two observation positions. Therefore, I define:

$$r_m = r_1 - \frac{1}{2}d \qquad (76)$$

Then:

$$r_m = \frac{1}{2}[a_{v1} \quad a_{v2}][a_{v1} \quad -a_{v2}]^{LI} d \qquad (77)$$

This is the simple, general expression for the location of a point of interest, given experimentally determined apparent positions, when the perspective displacement d is oriented in some arbitrary direction. Expression (77) is correct as long as the motion of the camera between the two viewing positions is a pure translation.

To compare (77) to my previous result, I note that the left pseudo-inverse of a matrix can be written as:

$$\text{i } A^{LI} = (A^T A)^{-1} A^T \qquad (78)$$

Now, the inverse of the 2×2 matrix $A^T A$ can be calculated explicitly because:

$$\begin{bmatrix} a & b \\ c & d \end{bmatrix}^{-1} = \begin{bmatrix} d & -b \\ -c & a \end{bmatrix} \frac{1}{ad - bc} \qquad (79)$$

so that, after quite a bit of manipulation, (77) becomes:

$$r_m = \frac{1}{2}\left(\frac{a_{v1} a_{v2}^T a_{v2} a_{v1}^T - a_{v1} a_{v1}^T a_{v2} a_{v2}^T + a_{v2} a_{v2}^T a_{v1} a_{v1}^T - a_{v2} a_{v1}^T a_{v1} a_{v2}^T}{a_{v1}^T a_{v1} a_{v2}^T a_{v2} - a_{v1}^T a_{v2} a_{v2}^T a_{v1}}\right) d \qquad (80)$$

The numerator of the fraction in (80) is a 3×3 matrix, while the denominator is a scalar. The denominator can be expanded and written reasonably compactly as:

$$\text{denom} = \frac{i^2((x_{im1} - x_{im2})^2 + (y_{im1} - y_{im2})^2) + (x_{im1} y_{im2} - x_{im2} y_{im1})^2}{i^4} \qquad (81)$$

while the numerator matrix is much too lengthy to reproduce here. To compare result (80) with (66), I will specify d as being directed along the x axis, as was assumed in the derivation of (66). Then only the terms in the first column of the matrix in (80) will appear in the result for $r_m$ and it is practical to write this result down:

$$r_m = \frac{1}{2\,\text{denom}} \begin{bmatrix} \dfrac{d(i^2(x_{im1}^2 - x_{im2}^2) + x_{im1}^2 y_{im2}^2 - x_{im2}^2 y_{im1}^2)}{i^4} \\ \dfrac{d(i^2(x_{im1} - x_{im2})(y_{im1} + y_{im2}) + 2y_{im1}y_{im2}(x_{im1}y_{im2} - x_{im2}y_{im1}))}{i^4} \\ \dfrac{-d(2i^2(x_{im1} - x_{im2}) + (y_{im1} + y_{im2})(x_{im1}y_{im2} - x_{im2}y_{im1})}{i^3} \end{bmatrix} \quad (82)$$

When I recall that result (66) also assumed that $y_{im1}=y_{im2}$, I find from (81) and (82) that $$r_m = \frac{d}{2(x_{im2} - x_{im1})} \begin{bmatrix} -(x_{im1} + x_{im2}) \\ -2y_{im1} \\ 2i \end{bmatrix} \quad (83)$$

for that case. Clearly, (83) is identical to (66).

Recall also that above I introduced the notion of averaging the two measurements in y, to get a better overall estimate in the presence of noise. I compare this concept to the result (82) by assuming that $y_{im1}=y_0+y_1$ and $y_{im2}=y_0-y_1$ and then taking the limit as $y_1$ gets small. Plugging into (82) I find:

$$r_m = \frac{d}{2(x_{im2} - x_{im1})} \begin{bmatrix} -(x_{im1} + x_{im2}) \\ -(y_{im1} + y_{im2}) \\ 2i \end{bmatrix} \quad (84)$$

Expression (84) shows that averaging the two y measurements gives the same answer as the full least squares formalism when the two measurements are close together.

The optimum way to use the four measurements, according to the least squares criterion, is given by (77). This reduces to (84) for the case when d is directed exactly along the x axis. According to the least squares formalism, the guideline idea of Nonami and Sonobe, which I have discussed above, is less than optimal. In addition, the guideline in its simple form as taught by those inventors, can be applied only to the system geometry assumed by them.

Another important conclusion from expression (77) is that the determination of the position of a point, r, from the measured data requires only the knowledge of the perspective displacement vector d, as expressed in the P1 coordinate system, and the image distance or effective focal length, i (from (69)). Of course, the image point position data incorporated in visual location vectors $a_{v1}$ and $a_{v2}$ must have been corrected for the distortion of the optical system before being used in (77), as was previously explained.

F. General motion between camera positions

I now consider the case where the camera does undergo a rotation as well as a translation between viewing positions P1 and P2.

Considering again FIG. 43, an arbitrary vector $r_1$ can be expressed as:

$$r_1 = d + r_2 \quad (85)$$

where the vector $r_2$ is drawn from the origin of the P2 coordinate system to the end of vector $r_1$. Any or all of these vectors could be expressed in either coordinate system. I choose to define them as being expressed in P1 coordinates. Then $r_2 = r_1 - d$ can be re-expressed in the P2 coordinate system by using the transformation that the coordinates of a point undergo when a coordinate system is rotated about its origin.

It is a fact that there is no single set of coordinates that can be defined that will uniquely represent the general rotation of an object in three dimensional space. That is, for any coordinate system one might choose, the order in which various sub-rotations are applied will affect the final orientation of the object. Thus, one must make a specific choice of elemental rotations, and the order in which they are applied, to define a general rotation.

The way that coordinate system rotations are most often defined is to begin with the two coordinate systems in alignment. Then one system is rotated about each of its coordinate axes in turn, to produce the final alignment of the rotated coordinate system. I define the recipe for rotating coordinate system P2, beginning with it aligned with P1, to obtain the rotated coordinate system P2 as the following:

1. Rotate P2 about $\hat{x}_2$ by an angle $\theta_x$.
2. Rotate P2 about $\hat{y}_2$ by an angle $\theta_y$.
3. Rotate P2 about $\hat{z}_2$ by an angle $\theta_z$.

This recipe means that the effect of this rotation of the P2 coordinate system with respect to the P1 coordinate system on the coordinates of a point in space can be expressed in the P2 system as the product of a rotation matrix with the vector from the origin to the point. That is:

$$v_2 = R v_1 \quad (86)$$

or $$v_2 = R_z(\theta_z) R_y(\theta_y) R_x(\theta_x) v_1 \quad (87)$$

where $$R_z(\theta_z) = \begin{bmatrix} \cos\theta_z & \sin\theta_z & 0 \\ -\sin\theta_z & \cos\theta_z & 0 \\ 0 & 0 & 1 \end{bmatrix} \quad (88)$$

$$R_y(\theta_y) = \begin{bmatrix} \cos\theta_y & 0 & -\sin\theta_y \\ 0 & 1 & 0 \\ \sin\theta_y & 0 & \cos\theta_y \end{bmatrix}$$

$$R_x(\theta_x) = \begin{bmatrix} 1 & 0 & 0 \\ 0 & \cos\theta_x & \sin\theta_x \\ 0 & -\sin\theta_x & \cos\theta_x \end{bmatrix}$$

and where $v_1$ is the vector between the origin of the P2 coordinate system and the point as expressed in the unrotated P1 coordinate system and $v_2$ is the same vector as expressed in the rotated P2 coordinate system.

The transformation to go the other way, that is, to change coordinates as measured in the rotated P2 system to coordinates measured in the P1 system is:

$$v_1 = R^{-1} v_2 v_1 = R_x^{-1}(\theta_x) R_y^{-1}(\theta_y) R_z^{-1}(\theta_z) v_2 v_1 = R_x(-\theta_x) R_y(-\theta_y) R_z(-\theta_z) v_2 \quad (89)$$

Consider again the perspective measurement process. At viewing position P1, visual coordinate location measurements are made in a coordinate system which depends on the orientation of the camera at that position. When nodal point of the camera is moved to position $d_{v1}$ as measured in the P1 coordinate system, the camera will rotate slightly, so that the visual coordinate system at position P2 is not the same as it was at position P1. I refer to the rotation matrix, which transforms coordinates measured in the visual coordinate system at P1 to coordinates measured in the visual coordinate system at P2, as $R_{12}$. Clearly this rotation matrix is a product of three simple rotations, as detailed in (87) and (88). But, I have shown how to express measurements made in the P2 coordinate system in terms of the P1 coordinate system:

$$r_{v1} = R_{12}^{-1} r_{v2} \tag{90}$$

so that I can now express Equations (70) as:

$$r_{v1} = z_{v1} a_{v1} r_{v1} = R_{12}^{-1} z_{v2} a_{v2} + d_{v1} \tag{91}$$

and these can be solved as above to get:

$$r_{vI} = \frac{1}{2} \left[ [a_{vI} \ R_{12}^{-1} \ a_{v2}][a_{vI} - R_{12}^{-1} a_{v2}]^{LI} + I_3 \right] d_{vI} \tag{92}$$

where, to repeat, $d_{v1}$ is the translation of the camera nodal point between positions P1 and P2 as expressed in the P1 coordinate system.

In analogy with (76) and (77) I define a new coordinate system:

$$r_m = r_{vI} - \frac{1}{2} d_{vI} \tag{93}$$

Then:

$$r_m = \frac{1}{2} [a_{vI} \ R_{12}^{-1} \ a_{v2}][a_{vI} - R_{12}^{-1} a_{v2}]^{LI} d_{vI} \tag{94}$$

Comparing (94) to (77) shows that any camera rotation between viewing positions P1 and P2 is easily taken into account in the perspective measurement, as long as that rotation is known.

Error Analysis; How to Achieve the Best Measurement Precision

A. Introduction

In the prior art no-one has adequately examined the errors in the perspective measurement. As a result, there are several important system design considerations that have not been taught by the prior art. Taking proper account of these considerations is key to the development of a truly accurate metrology system.

In this section, I determine the major source of random errors in the measurements, and examine the effects of these random errors. This error analysis uncovers several important things; these include not only how precisely the measurement can be made, but also how to arrange the system to get the best results. The most important result is that one must adjust the perspective baseline to be proportional to the distance between the object and the camera(s), in order to minimize the random error.

If one were able to compare the measurement results obtained with any practical instrument to the (somehow known) true value of the quantity being measured, one would find that there are two types of error made by the instrument.

An error component which varies randomly from measurement to measurement is called random error or noise, and the effect of it is to limit the precision or repeatability of the measurement. The mean squared deviation from the average value in a measured (constant) quantity over a large number of trials is called the variance. The square root of the variance is known as the root—mean—square (RMS) error.

Other error components, which are either constant from measurement to measurement, or which vary in some deterministic (i.e., non-random) way are called systematic errors. Depending on their characteristics systematic errors are sometimes referred to by terms such as offset, bias, and drift.

To make an accurate measurement means both that the measurement is precise (that is, the random error variance is small) and that the systematic errors in the measurement are small.

Random errors are generally the more fundamental limits to system performance because they can never be entirely eliminated, but only minimized. Systematic errors can, in principle, be eliminated (or, more correctly, brought to any level as small as one requires) by appropriate calibration and error compensation processes. The limit to how well one can reduce systematic errors is set by the random error in the calibration measurements. This means that it is the minimization of random measurement errors which is the key to obtaining the best measurement system performance.

Random errors can usually be reduced by repeating the measurement a number of times and averaging the results. Fundamentally, this means that the more time that is spent making the measurement, the more precise the measurement can be. This is an important concept for instrument calibration, because generally there will be relatively much more time available to make calibration measurements than there is to make individual production measurements. Accordingly, calibration measurements can be made much more precisely than can production measurements. The other requirement for calibration is that there be available primary standards to which the output of the instrument can be compared. For mechanical metrology, such standards are commonly available in a wide range of accuracies The sources of error in the perspective measurement can be understood by examining the measurement Equation (94) and the geometry of a given system. The sources of random error in the measurement will be the user alignment or "pointing error" and random errors in the motion of the camera. The pointing error enters the measurement through $a_v$, while errors in the motion enter the measurement through $R_{12}$ and $d_{v1}$. I will show that the pointing error will usually be the dominant source of random error in my preferred embodiments.

B. Pointing Error

The preferred embodiments of the perspective measurement process I am teaching requires the user to align fiducial marks ("cross-hairs" or "cursors") with specific points on the video image of the object under inspection. This alignment must be done twice, from different viewing positions. As the user attempts to locate a specific point on the edge of an object feature he or she must judge when the fiducial is coincident with a specific brightness level on the edge.

There are three sources of uncertainty which limit the precision to which the user can perform this task. These are video noise, the psychological limit to the ability of the user to detect differences in illumination levels, and the quantized nature of motion of the cursor.

One can make a simple estimate of the random alignment error which will be made by the user by considering only the quantized nature of the motion of the video cursor. For the moment I ignore the alignment variance caused by video noise and the psycho-physical limitations to the user's performance. The fact that standard video systems have a finite number of scan lines will in itself lead to a significant limit to the precision to which the user can align the cursor to the image of the object.

My purpose here is to make a representative calculation of the level of the pointing error the user will make in order to help the reader understand the invention and its relationship to the prior art. It is not my purpose to predict the exact error level of any particular embodiment of my system.

The error due to a quantized measurement is well known. The error has an equal probability of being anywhere within the range $-w/2$, $w/2$ where w is the width of the measurement quantization, i.e., the distance between the allowed values of the output. As is well known, and easily calculated, the variance of a uniformly distributed random variable with a distribution w wide is:

$$\sigma^2_{quantization} = \frac{w^2}{12} \tag{95}$$

Thus, the variance of the cursor alignment is:

$$\sigma^2_p = \frac{w^2_p}{12} \tag{96}$$

where $w_p$ is the quantization width of the cursor position.

Now as was shown in FIG. 5, the field of view of the borescope or camera will appear as a circle more or less centered on the video screen. I assume that the camera FOV covers a fraction K of the video field height. Standard NTSC or EIA video contains approximately 480 lines per frame. Therefore, in the video vertical direction, the width of the cursor position uncertainty is:

$$w_{pv} = \frac{1}{480k} \tag{97}$$

in units of the camera FOV. Using (96), the RMS deviation in the alignment of the cursor along the video vertical direction is then:

$$\sigma_{cv} = \frac{w_{pv}}{\sqrt{12}} \tag{98}$$

or approximately 1/1300 of the field of view for K of about 0.8. The RMS angular deviation of the cursor location in the video vertical direction is then just the field of view of the camera multiplied by $\sigma_{cv}$.

Since the field of view of standard borescopes is in the range of 30 to 90 degrees, the RMS pointing error will be approximately 0.4 to 1.2 milliradian. The angular errors of commercial translation stages range from ten to several hundred microradians, so that the pointing error will be the dominant random error source for most embodiments of my invention.

In the video horizontal direction, there is not necessarily any similar restriction on the number of possible cursor positions. If there are $N_{cursor}$ positions for the cross-hair across the horizontal extent of the frame, this is equivalent to 3/4$N_{cursor}$ positions in one video field height. The horizontal cursor position uncertainty will be:

$$w_{ph} = \frac{4}{3\kappa N_{cursor}} \tag{99}$$

in units of camera FOV. The higher resolution possible for horizontal cursor positioning compared to the vertical direction will be valuable in achieving the best system performance, as explained further below. The measurement system could, of course, use high resolution video rather than the standard video I have just discussed. In this case, not only would the number of video lines be higher, but there may not be a difference in resolution between vertical and horizontal. Use of such video will not change any of the conclusions below, except that there would then be no reason for a particular alignment of the horizontal video axis. However, I have found that the optical quality of standard rigid borescopes is not sufficient to justify the use of high resolution video.

C. The effects of pointing error

The effects of pointing error can be conveniently analyzed by reference to FIG. 44. In FIG. 44 a point $P_i$ is being viewed from two camera positions P1 and P2. The x axis is defined to lie along the line joining points P1 and P2, and the origin of the coordinate system is placed at the midpoint of this line. The plane y=0 is defined to be the plane containing the three points, P1, P2, and $P_i$. The z axis is then defined by $\hat{z}=\hat{x}\times\hat{y}$.

I call this coordinate system the error analysis coordinate system. Comparing FIG. 44 with FIG. 41 shows that the difference here is that the (x, z) plane of the error analysis coordinate system is always defined to contain the two observation positions and the point being observed. If a viewing position or the point being observed move, this coordinate system moves to follow them. Unlike previous coordinate systems I have defined, this error analysis coordinate system has no inherent relationship to the internal coordinate system of the camera.

The viewing angles $\xi_x$ are measured from the z axis. Angles are defined as positive if the rotation about the y axis is counterclockwise. The angle subtended by the two observation positions at the point being observed is defined as $\Theta=\xi_{x1}-\xi_{x2}$.

The location of the point $P_i$ in these coordinates in terms of the viewing angles measured from the camera positions is:

$$z_{ea} = \frac{d}{\tan(\xi_{x1}) - \tan(\xi_{x2})} \tag{100}$$

$$x_{ea} = \left(\frac{z}{2}\right)(\tan(\xi_{x1}) + \tan(\xi_{x2}))$$

$$y_{ea} = \left(\frac{z}{2}\right)(\tan(\xi_{y1}) + \tan(\xi_{y2}))$$

Of course, $y_{ea}$ has just been defined to be zero, but the expression given above is needed to consider the effects of errors in the measurement of the angles.

Since the position measurement depends on four angular measurements, there are four angular errors, which will be denoted as $d\xi_{x1}$, $d\xi_{x2}$, and $d\xi_{y2}$. For small errors, a linear model is appropriate, so the position error can be defined as:

$$\Delta r \equiv \begin{bmatrix} dx \\ dy \\ dz \end{bmatrix} = \begin{bmatrix} \frac{\partial x}{\partial \xi_{x1}} & \frac{\partial x}{\partial \xi_{x2}} & \frac{\partial x}{\partial \xi_{y1}} & \frac{\partial x}{\partial \xi_{y2}} \\ \frac{\partial y}{\partial \xi_{x1}} & \frac{\partial y}{\partial \xi_{x2}} & \frac{\partial y}{\partial \xi_{y1}} & \frac{\partial y}{\partial \xi_{y2}} \\ \frac{\partial z}{\partial \xi_{x1}} & \frac{\partial z}{\partial \xi_{x2}} & \frac{\partial z}{\partial \xi_{y1}} & \frac{\partial z}{\partial \xi_{y2}} \end{bmatrix} \begin{bmatrix} d\xi_{x1} \\ d\xi_{x2} \\ d\xi_{y1} \\ d\xi_{y2} \end{bmatrix} \equiv S\Delta t \quad (101)$$

where the sensitivity matrix S can be calculated from expressions (100).

I assume that the random angle errors $\Delta t$ have zero mean, that is $$\langle \Delta t \rangle \equiv \begin{bmatrix} \langle d\xi_{x1} \rangle \\ \langle d\xi_{x2} \rangle \\ \langle d\xi_{y1} \rangle \\ \langle d\xi_{y2} \rangle \end{bmatrix} = \begin{bmatrix} 0 \\ 0 \\ 0 \\ 0 \end{bmatrix} \equiv 0 \quad (102)$$

where the individual angular measurement errors are characterized by random variables $d\xi_{x1}$, etc. and angle brackets are used to indicate the mean of a random variable. Clearly expressions (101) and (102) imply that $\langle \Delta r \rangle = 0$ as well.

The variance of the position error is:

$$\langle |\Delta r|^2 \rangle = \langle \Delta r \Delta r \rangle = \langle \Delta t^T S^T \Delta t \rangle = \langle \Delta t^T G \Delta t \rangle \quad (103)$$

Using the mathematical facts that the trace of a scalar is equal to the scalar, and that the trace of any permutation of a square matrix product is unchanged, one has:

$$\langle \Delta t^T G \Delta t \rangle = \langle Tr(\Delta t^T G \Delta t) \rangle = \langle tr(G \Delta t \Delta t^T) \rangle = Tr(G \langle \Delta t \Delta t^T \rangle) \quad (104)$$

The quantity $(\Delta t \, \Delta t^T)$ is called the covariance matrix of the random variables $\Delta t$. If one assumes that the individual random angular error variables are uncorrelated (this is a much less restrictive condition than assuming that they are statistically independent), then the off diagonal elements of the covariance matrix are zero.

Thus, for uncorrelated angular measurement errors, the variance of the position error can be written as $$\langle |\Delta r|^2 \rangle + G_{22} \langle (d\xi_{x2})^2 \rangle + G_{33} \langle (d\xi_{y1})^2 \rangle + G_{44} \langle (d\xi_{y2})^2 \rangle \quad (105)$$

where $G = S^T S$, and S is the sensitivity matrix defined in Equation (101).

Because my instrument is meant to measure the distance between two points in space, rather than the absolute position of a single point, what one really cares about is the quantity:

$$\delta r = \Delta r_b - \Delta r_a \quad (106)$$

where points a and b are the two points whose positions are determined by the perspective measurement. That is, errors in the absolute positions of points are less important than the error in the difference between the positions of two points. If one further assumes that the angular measurement errors made for point b are uncorrelated with the errors made for point a, then the variance of $\delta r$ is:

$$\langle |\delta r|^2 \rangle = \langle |\Delta r_a|^2 \rangle + \langle |\Delta r_b|^2 \rangle \quad (107)$$

i.e., the variance of the position difference is just equal to the sum of the variances of the two position determinations.

Expression (107) implies that one can usefully study the effects of pointing errors by simply looking at the variance of $\Delta r$. If two object points are measured with equal error variance, then the variance of the distance between the two points, given by (107), will be just twice the variance of $\Delta r$. If the variance of the measurement of one point is much larger than the other, then it will dominate the sum in (107). Thus, the variance in the distance determined between two points ranges from the larger variance of the two individual point positions to, at most, twice this value.

D. Sensitivity of the Measurement in Error Analysis Coordinates

Using (100) and (101), one finds that $$S = \begin{bmatrix} \frac{\left(\frac{d}{2}-x\right)\left(\left(x+\frac{d}{2}\right)^2+z^2\right)}{dz} & \frac{\left(\frac{d}{2}+x\right)\left(\left(x-\frac{d}{2}\right)^2+z^2\right)}{dz} & 0 & 0 \\ 0 & 0 & \frac{z}{2} & \frac{z}{2} \\ -\frac{\left(x+\frac{d}{2}\right)^2+z^2}{d} & \frac{\left(x-\frac{d}{2}\right)^2+z^2}{d} & 0 & 0 \end{bmatrix} \quad (108)$$

where expressions in terms of the angles have been replaced by equivalent expressions in terms of the coordinates of the unknown point $(x_{ea}, y_{ea}, z_{ea})$. The subscript denoting that these are error analysis coordinates has been dropped in (108) for clarity.

Using Equation (103) one finds:

$$G_{11} = \frac{1}{d^2 z^2}\left(\left(x+\frac{d}{2}\right)^2+z^2\right)^2\left(\left(\frac{d}{2}-x\right)^2+z^2\right) \quad (109)$$

$$G_{22} = \frac{1}{d^2 z^2}\left(\left(x-\frac{d}{2}\right)^2+z^2\right)^2\left(\left(\frac{d}{2}+x\right)^2+z^2\right)$$

$$G_{33} = G_{44} = \frac{z^2}{4}$$

where the subscripts have been dropped again. I will drop the subscripts in the discussion below, except where there is a possibility of confusion with other expressions that apply to other coordinate systems.

First, notice that according to (105) and (109), when z is large with respect to x and d, the position error variance is proportional to $$z^2 \left(\frac{z^2}{d^2}\right)$$

for angular errors in $\xi_x$, while it is proportional to $z^2$ for errors in $\xi_y$. The position error depends much more strongly on errors in the $\xi_x$ direction than it does errors made in the $\xi_y$ direction.

This is important for the design of the measurement system, because most video systems have a higher resolution in one direction (horizontal) than they do in the other (vertical). Also, as I have already mentioned, my system is not necessarily restricted to any particular value of cursor resolution along the video horizontal direction. For both of these reasons then, it is important for best results to arrange the perspective displacement to lie along the high resolution direction of the video camera.

This is more important than it might appear at first. For my electronic measurement borescope (third preferred embodiment) and for my electronic measurement endoscope (fourth preferred embodiment) it is straightforward to orient the camera so that the high resolution direction is aligned along the perspective displacement. However, for my first two (BPA) embodiments, the requirement to align the perspective displacement along the video horizontal direction means that there must be a specific rotation of video camera back or video sensor 134 with respect to borescope 120 (FIG. 1) in order to obtain the smallest measurement error. This specific alignment can be most simply defined as aligning the high resolution axis of the video sensor to lie parallel to the projection of the perspective displacement into the field of view of the borescope, as seen at the position of the video sensor. This definition allows for the possibility that there may be a rotation of the image about the optical axis within borescope 120, so that the external view in FIG. 1 may not show the entire geometrical relationship between field of view 122 and camera back 134.

Secondly, note that the position error variance when d is small is proportional to $$\frac{z^4}{d^2}.$$

For a fixed perspective baseline, d, the RMS position error is then proportional to $z^2$. However, if the baseline is made proportional to z, then the RMS error will be proportional to z/c where c is the constant of proportionality. Thus, making the perspective baseline variable, according to the distance of the point to be located, can produce a dramatically smaller measurement error.

I will assume for further analysis that $<(d\xi_{x1})^2> = <(d\xi_{x2})^2>$, i.e., the variance of the error in the measurement of $\xi_x$ is the same at either viewing location. I will also assume that the variance of $\xi_y$ has the same property. Further, I will assume that the variances do not depend on the angles at which the point is being viewed.

These assumptions put requirements on the characteristics of the camera, if they are to apply to the actual measurement. I will later examine the effects of camera characteristics and camera orientation on the measurement results.

With the assumptions given one can write:

$$<|\Delta r|^2> = (G_{11}+G_{22})<(d\xi_x)^2> + (G_{33}+G_{44})<(d\xi_y)^2> \quad (110)$$

To minimize the position variance requires minimizing both terms in (110) separately. From Equation (109) it is clear that there is nothing that can be done to minimize the term multiplying $d\xi_y$. However, when $x_{ea}=0$, one finds:

$$G_{11} + G_{22} = \frac{(4z_{ea}^2 + d^2)^3}{32 d^2 z_{ea}^2} \quad (111)$$

The error coefficient (111) grows large as d approaches zero and also as d gets large. Thus, there is an optimum value for the perspective baseline. The value of d which minimizes (111) is:

$$d_{opt} = \sqrt{2}\, z_{ea} \quad (112)$$

At the optimum baseline, the position error variance (110) is:

$$\langle |\Delta r|^2 \rangle = \left[\frac{27}{8}\langle(d\xi_x)^2\rangle + \frac{1}{2}\langle(d\xi_y)^2\rangle\right] z_{ea}^2 \quad (113)$$

Note that even though the effect of $d\xi_x$ has been minimized, the coefficient that multiplies it is still much larger than the coefficient of $d\xi_y$.

FIG. 45 depicts the measurement being made when the optimum perspective baseline is used and $x_{ea}$ is zero. At the optimum baseline, the measurement error due to pointing angle errors is as low as it can be, given the assumption that the errors are the same at both camera viewing positions, and independent of angle. This optimum measurement geometry can be described simply as requiring that the angle subtended at the object point by the perspective baseline be approximately 70 degrees, regardless of the distance between the object point and the camera positions.

Figure 46:
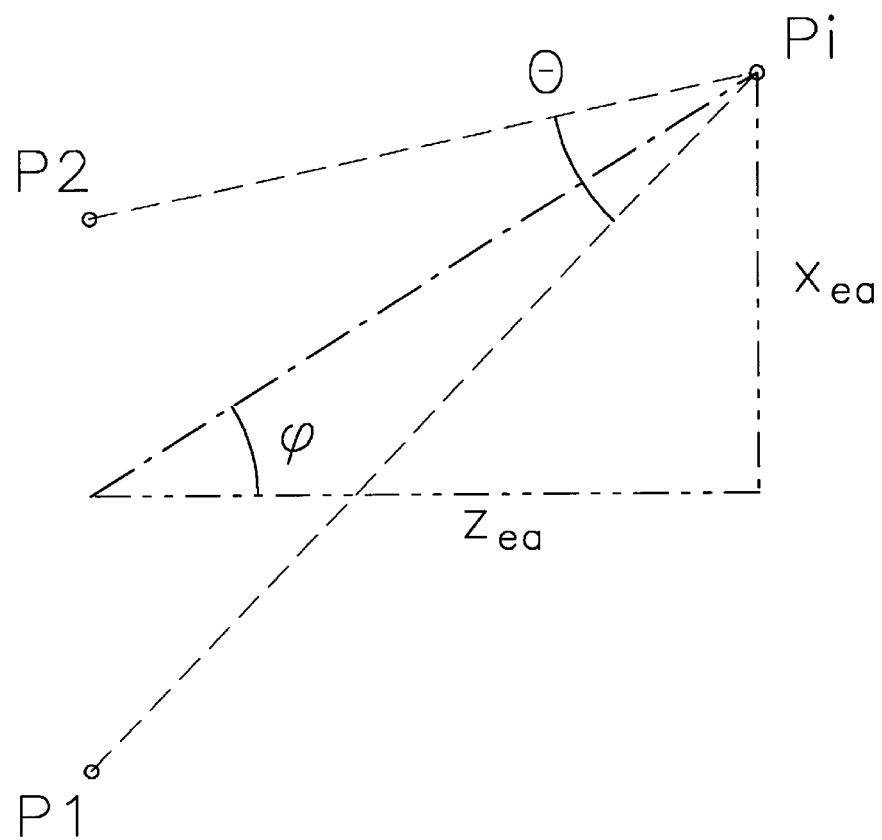
FIG. 46 depicts the perspective measurement in error analysis coordinates when the point of interest does not lie equally distant from the two viewing positions.
Figure 47:
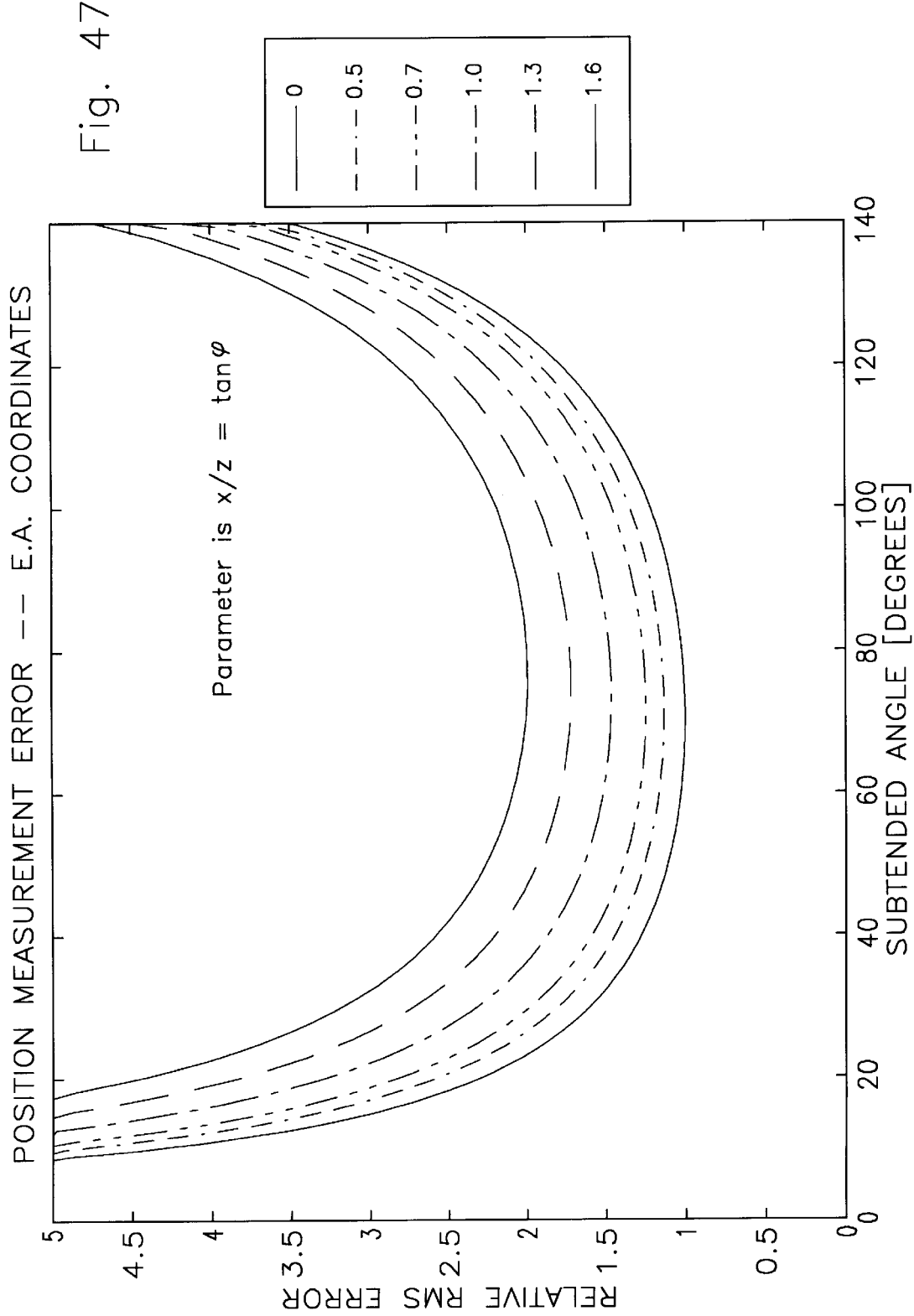
FIG. 47 shows the relative position error made in the perspective measurement as a function of the angle subtended by the perspective baseline at the point of interest.

FIG. 46 depicts the measurement being performed when $x_{ea}$ is not zero. Here the off-axis angle $\phi$ is defined by $\tan(\phi) = x_{ea}/z_{ea}$. Using (109) and (110) the optimum baseline for a given combination of $x_{ea}$ and $z_{ea}$ can be determined, as can the angle subtended at the object point by the perspective baseline when it is optimum. These results cannot be expressed by simple equations, but they can be calculated numerically. One finds that the optimum subtended angle, $\Theta_{opt}$, slowly increases as $x_{ea}$ increases, from 70.53 degrees at $x_{ea}$ equals zero towards a value of 90 degrees as $x_{ea}$ gets infinitely large.

FIG. 47 shows the relative measurement error as a function of the subtended angle with the off-axis position as a parameter. It is clear that there is a broad minimum in the error centered at approximately 70 to 80 degrees subtended angle for a large range of object point locations. It is also clear that one can achieve good measurement results over a range of subtended angle, $\Theta$, between approximately 40 degrees and 100 degrees. This means that it is much less important to use the optimum value of the subtended angle than it is to use a constant subtended angle, or at least one that remains in the optimum range, as the distance of the object varies.

Also, from FIG. 47 one can see that the error for a point at $\phi=45$ degrees (i.e., $x_{ea}/z_{ea}=1$) is about 50% greater than the error for a point on axis. Thus, the perspective measurement can be used with good results for object points at least this far off axis.

To give one example, the measurement will be made with $x_{ea}$ not equal to zero when the camera is a rigid borescope as in my first two embodiments, and when the viewing angle, VA, is not equal to 90 degrees. See FIGS. 9 and 40. I have just shown that the level of increased error when the perspective measurement is not made at a viewing angle of exactly 90 degrees is small enough that the measurement technique is useful for a wide range of borescope fields of view and viewing angles.

To summarize, the key to making a perspective measurement with the smallest random error is to keep the angle subtended by the perspective baseline at the object point constant with distance. The subtended angle should be chosen to be at least 40 degrees, and preferably as close to 70 degrees as practical. If the subtended angle is constant with distance, the perspective baseline will necessarily be proportional to the distance to the object point, and the random error in the measurement due to pointing error will be proportional to the distance between the object point and the camera positions, rather than proportional to the square of that distance as is the case when the perspective baseline is fixed. An additional important consideration is that if the camera has a higher resolution in one direction than the other, then the high resolution direction should be aligned with the perspective displacement for best measurement results.

All of these results are based on the assumptions that $d\xi$ is independent of $\xi$ and is the same at both P1 and P2. I now examine these assumptions.

E. The Effects of Camera Characteristics and Orientation

What is measured experimentally is the position of image points on the focal plane of the camera. These measurements are corrected for distortion and interpreted in terms of angle as shown in Equations (2) and (3) and Equations (41) and (42). The analysis of pointing error in sub-section B. above estimates the error in the image position measurement, $\Delta x_{im}$. The relationship between this error and the angular error of the measurement, $d\xi$, depends on the characteristics as well as the orientation of the camera.

The characteristics of the camera that determine the relationship between the image position error and the angular error are distortion and aberrations. My previous estimate of $\Delta x_{im}$ was constant throughout the field of the camera. However, $\Delta x_{im}$ will be a function of the position of the point in the field of view if there are significant aberrations in the camera's optical system that vary with field angle. This is because the noise sources which were neglected previously, video noise and the psychological limit to the ability of the user to detect differences in illumination levels, determine a minimum resolution in illumination. Any error in the illumination level judged by the user as the position of the edge of the object feature of interest will become a corresponding error in the image position. The proportionality between the error in illumination level and the image position error is the slope of the illumination at the edge of the image of the object feature. This image illumination edge slope depends on the level of aberrations in the optical system.

Consider first a perfect camera, such as that shown in FIG. 42. In this case, perfect means no distortion and no aberration. As discussed previously, the relationship between image position and field angle for this camera is:

$$x_{im} = f \tan(\phi_x)$$
$$y_{im} = f \tan(\phi_y) \qquad (114)$$

where $f$ is the equivalent focal length. The angular measurement error due to image position measurement error will be:

$$\Delta \phi_x = \frac{\partial \phi_x}{\partial x_{im}} \Delta x_{im} \qquad (115)$$

But from (114):

$$\frac{\partial \phi_x}{\partial x_{im}} = \frac{1}{f(1 + \tan^2(\phi_x))} \qquad (116)$$

so that the angular error decreases dramatically as the field angle gets large. Thus, for the perfect camera it makes a great deal of difference what the orientation of the camera is when the perspective measurement is made.

In fact, if a perfect camera is assumed to be used for the measurement, and if the camera coordinate axes are assumed to be aligned with the error analysis coordinates defined in FIG. 44, one finds that there is no optimum perspective baseline. The measurement error will decrease continuously as d increases, without limit. This, of course is not a realistic situation, since no camera can cover an infinitely large focal plane, which is what it must do to maintain relationship (114).

As a second example, consider a camera which has a particular kind and amount of distortion called "f-theta" distortion. For this camera the relationship between image position and angle is:

$$x_{im} = f \phi_z$$
$$y_{im} = f \phi_y \qquad (117)$$

In this case, the angular error is:

$$\Delta \phi_x = \frac{1}{f} \Delta x_{im} \qquad (118)$$

which is independent of field angle. Thus, for a camera that has "f-theta" distortion it does not matter how the camera is oriented when the angular location of an object point is determined. In this case, the optimum baseline (112) and the rest of the analysis of the previous sub-section applies, without modification, to the perspective measurement.

One can take into account the effect of aberrations by generalizing (115) as:

$$\Delta \phi_x(\phi_x) = \frac{\partial \phi_x}{\partial x_{im}} \Delta x_{im}(\phi_x) \qquad (119)$$

where aberrations partially determine $\Delta x_{im}(\phi_z)$.

Real cameras will have distortion and aberrations. They will also have a limited field of view. This means that a real camera may well have an optimum field angle, that is, a field angle at which the angular error $\Delta \phi_x(\phi_x)$ is minimized.

Figure 48:
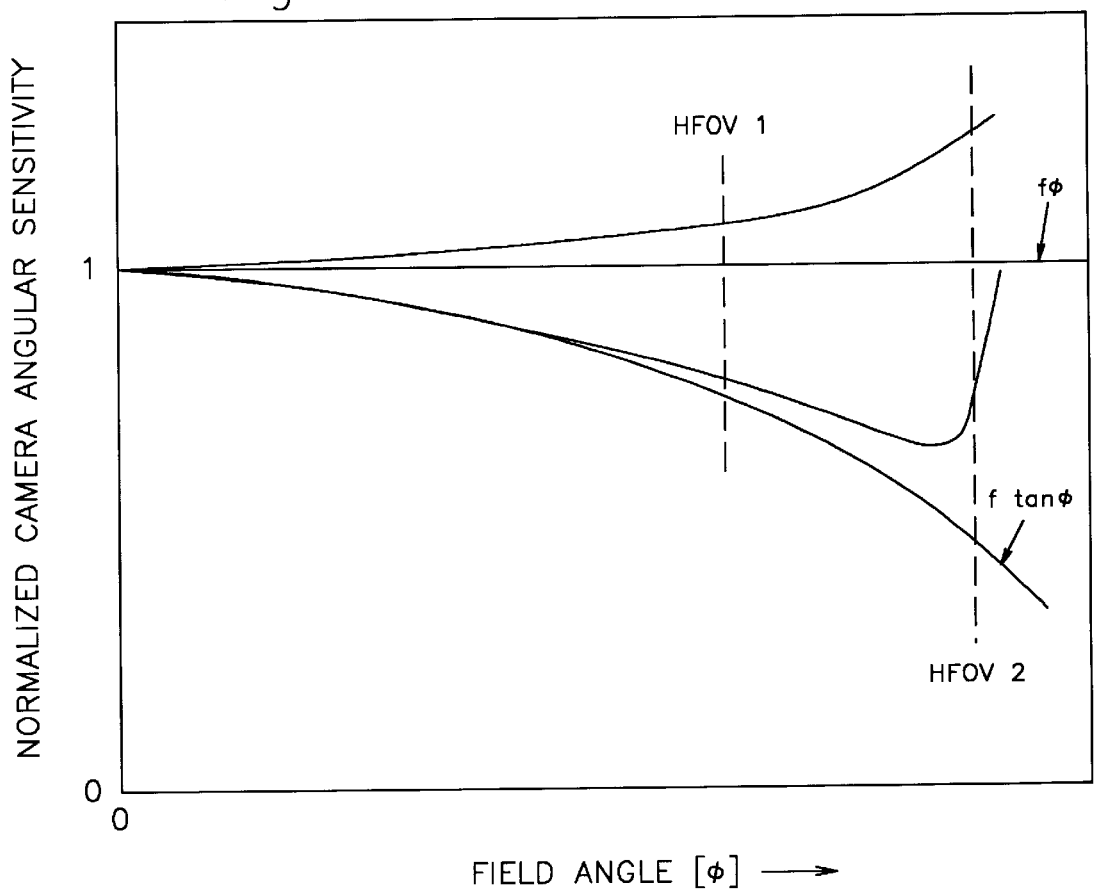
FIG. 48 shows four possible camera angular sensitivity functions.

The normalized camera angular sensitivity, which is the angular error (119) divided by the angular error at zero field angle, is depicted schematically in FIG. 48. In the Figure, four possible camera sensitivity functions are shown, as are two different possible camera half fields of view.

FIG. 48 shows qualitatively the types of sensitivity functions which are possible, assuming that the characteristics of the camera are symmetric about the optical axis. It is clear that there are three classes of camera angular sensitivity characteristics. These are:

(C1) Camera sensitivity is essentially independent of field angle.

(C2) Camera sensitivity has a distinct minimum at or near zero field angle.

(C3) Camera sensitivity has a distinct minimum at a significant distance away from zero field angle.

Camera sensitivity characteristic C1 can occur when the camera has a narrow field of view with small aberrations and small distortion, or when the distortion is "f-theta" (here, $f\phi$) or when the camera has large aberrations which are independent of field angle.

Camera sensitivity characteristic C2 can occur if the camera has a large amount of barrel distortion (that is, more than "f-theta") or if the camera has large aberrations which increase strongly with field angle which outweigh the effect of any distortion.

Camera sensitivity characteristic C3 can occur if the camera has either low distortion or pincushion distortion. If the camera has low aberrations as well, the minimum sensitivity will occur at the edge of the field of view. If the camera has large aberrations which increase with field angle, the minimum sensitivity will occur at an angle which is less than the full field angle. I call the field angle where the camera sensitivity is optimized $FA_{opt}$. Note that for cameras with characteristic C3, it will almost always be the case that the minimum sensitivity will not be exactly at the edge of the field, because almost all optical systems have rapidly increasing aberrations near the edge of the field of view.

Considering now the effect of the orientation of the camera in the perspective measurement, I will treat three cases. I now present rules for moving the camera to make the overall optimum measurement in each case.

A little thought will convince one that the overall optimum way to make the perspective measurement is to move the camera to the optimum positions in error analysis coordinates as shown in FIG. 45 and then to rotate the camera so as to make the measurement at the optimum field angle, if camera sensitivity characteristic is either C2 or C3. If camera characteristic is C1, then it doesn't matter what the camera orientation is when the measurements are made. This overall optimum measurement can be made with the two degree of freedom linear camera motion embodiment which was discussed in the section entitled "Embodiments Using Other Camera Motions" and which was depicted in FIG. 33.

My preferred embodiments also have straight line camera motion, but the camera orientation is constrained to be the same at P1 and P2. In this case the angle subtended at the object by the perspective baseline, $\Theta$, is directly visible to the user during the measurement The angle $\Theta$ is simply equal to the change in the apparent angular position of the point of interest between the views at P1 and P2. (Throughout the remainder of this discussion, I will be speaking of the true, i.e., distortion corrected, angles.)

In fact, any camera motion in which the camera orientation is fixed (i.e., the camera doesn't rotate as it moves) has the characteristic that the angle subtended at the object point of interest by the perspective baseline will be exactly the same as the apparent change in angular location of the point as viewed from the two positions.

The rules for making an optimum perspective measurement with my preferred embodiments, or with any camera motion in which the camera does not rotate, are the following:

Rule L1

If the camera characteristic is C1, that is, if the sensitivity is independent of field angle, and if the camera FOV is less than $\Theta_{opt}$, one simply moves the camera until the point of interest is viewed at either edge of the field of view. If the FOV is greater than $\Theta_{opt}$, then one moves the camera between two locations from which the apparent angular locations of the point of interest differ by $\Theta_{opt}$.

Rule L2

If the camera characteristic is C2, that is, if the camera sensitivity is minimized at the center of the field of view, then the optimum subtended angle for the measurement will be somewhat less than $\Theta_{opt}$. I call the value of this optimum subtended angle $\Omega_{opt}$. If the camera FOV is less than $\Omega_{opt}$, then one moves the camera until the object point is viewed at first one edge, then the other, of the FOV. If the camera FOV is larger than $\Omega_{opt}$, then one moves the camera between positions where the object point is viewed at $\pm\Omega_{opt}/2$. I call the angle $\Omega_{opt}/2$ the optimum measurement angle.

Rule L3

If the camera characteristic is C3, then the camera has an optimum field angle, $FA_{opt}$. This may be either smaller or larger than $\Theta_{opt}/2$. If $FA_{opt}$ is larger than $\Theta_{opt}/2$, then the overall optimum subtended angle will be somewhat smaller than $2\,FA_{opt}$ and somewhat larger than $\Theta_{opt}$. If $FA_{opt}$ is smaller than $\Theta_{opt}/2$, then the overall optimum subtended angle will be somewhat larger than $2\,FA_{opt}$ and somewhat smaller than $\Theta_{opt}$. I call the value of this optimum subtended angle $\Omega_{opt}$. In either case, for camera characteristic C3 one makes the optimum measurement by moving the camera between positions where the object point of interest is viewed at $\pm\Omega_{opt}/2$, that is at an optimum measurement angle.

Clearly, use of these rules requires detailed knowledge of the characteristics of the camera. In terms of my BPA embodiments, where the camera is a standard borescope, one can make some additional general statements. Borescopes have a large amount of barrel distortion, so that rules L1 or L2 will apply. How these rules are used depends on the field of view of the scope, and this varies widely between models, with most scopes having fields of view in the range of 30 to 90 degrees. However, standard borescopes also have, in general, a large increase in aberration near the edge of the field of view, so that one can be fairly sure that viewing a point exactly at the edge of the field of view will not result in an optimum measurement. This means that rule L2 applies.

For the vast majority of borescopes, the simple rule given earlier, which was to move the point of interest to somewhere near the edge of the field of view, will give good results in nearly all cases. To be more specific requires that one be more specific about the characteristics of the scope.

For use with a particular borescope, or in my EMB and EME embodiments, one could place a pair of fiducial marks inside the camera so that they appear within the field of view to indicate the optimum measurement angles of this specific camera. Additional marks could also be used to indicate an optimum range of measurement angles if this were useful for a particular case. Probably a more efficient thing to do is simply to indicate to the user by example diagrams approximately where the points of interest should be placed within the field of view of a specific camera to obtain an optimum measurement.

As a final note on the optimum use of fixed camera orientation embodiments, it is important to understand that FIG. 47 does not by itself allow one to compare the use of cameras of different fields of view in making the perspective measurement. Clearly, a narrow field of view camera cannot make the perspective measurement with a large subtended angle at the object point in a fixed camera orientation embodiment. But, the narrow field of view camera will have a smaller noise than will a large field of view camera when using the same solid stage imager. Whether one particular camera will give better measurement results than another can only be determined by careful consideration of the combined effects of the camera sensitivity functions, FIG. 48, and the dependence of measurement error on subtended angle, FIG. 47.

For circular camera motion, where the camera is constrained so that its optical axis lies in the plane of the circular path as shown in FIG. 34, the orientation of the camera changes between P1 and P2 so that the optical axis of the camera always passes through the center of curvature of the circular path. As a result, the apparent angular motion of the point being observed depends on the location of the point relative to the center of curvature. The apparent angular motion of the point is, for instance, zero when the point is located at the center of curvature. Note that this means that the perspective measurement of distance can be accomplished even when one of the points of interest exhibits no parallax.

Figure 49:
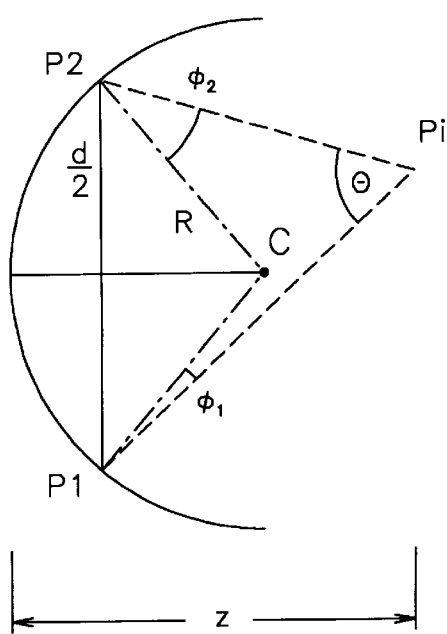
FIG. 49 depicts the relationship between the angle subtended at the point of interest by the perspective baseline to the apparent angles at which the point is viewed, for circular camera motion, when the optical axis of the camera lies in the plane of the path of motion.

Although the apparent angular motion of a point as the camera moves depends on the location of the point, the actual angle subtended at the point by the perspective baseline can be easily determined from the following equation, which can be understood from FIG. 49:

$$\Theta = \phi_1 - \phi_2 + 2\arcsin\left[\frac{d}{2R}\right] \qquad (120)$$

Equation (120) allows one to determine the angle subtended at the point of interest by the perspective baseline using only the information that is available during the measurement.

If the distance, z, is less than the radius of curvature, R, then this distance is minimized if the midpoint between P1 and P2 lies along the line which contains the center of curvature, C, and the point of interest. This will be the optimum measurement situation for this camera motion, and it is easily obtained if one begins the measurement by first moving the camera until the point is observed to be coincident with the optical axis of the camera. (If the point of interest is near the center of motion, then it will always remain near the optical axis. In this case, one simply moves to the center of the range of motion.) One then moves the camera equal distances in both directions from this starting position, and calculates the resulting subtended angle at the point of interest by use of (120).

Note that Equation (120) applies to linear motion as well; one simply takes $R \to \infty$. Equation (120) is a specific example of a more general equation which applies to the general camera motion embodiment:

$$\Theta = \phi_1 - \phi_2 - \phi_R \tag{121}$$

where $\phi_R$ is the rotation of the camera between positions P1 and P2 in the $(x_{ea}, z_{ea})$ plane.

For this circular camera motion, the rules for making an optimum perspective measurement depend on the position of the object within the primary operating range of this system which was previously defined to be ($0 \leq z \leq 2R$). The rules can be best summarized in the form of a table, which is provided here as Table 1.

TABLE 1

Optimum Perspective Measurement for Circular Camera Motion, Optical Axis Constrained to Plane of Motion

| Camera Sensitivity Class | C1 | C2 | C3 |
|---|---|---|---|
| Distance $z \ll R$ | Use Rule L1 | Use Rule L2 | Use Rule L3 |
| $z \approx R$ | | Move to positions Where $\Theta = \pm \frac{\Theta_{opt}}{2}$ | |
| $z \approx 2R$ | Use Rule L1 | Use Rule L2 | Use Rule L3 |

For the second and third rows of Table 1, one uses the rule in the table if it is feasible. If there is not sufficient range of camera motion, then it may not be possible to move the camera as far as called for by these rules, and one then moves as far as possible. In the case of the third row of the table, it is possible that one could be limited by the field of view of the camera. In that case, one also moves as far as feasible.

F. The Random Error in Variable and Fixed Baseline Linear Camera Motion Systems

Figure 50:
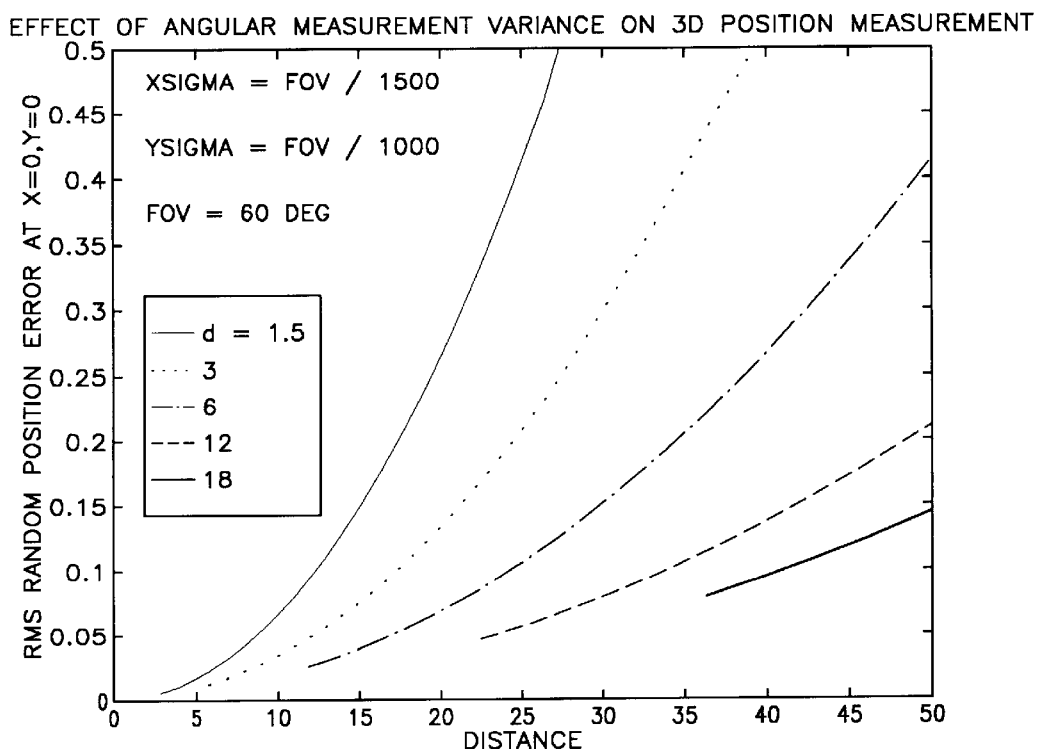
FIG. 50 shows the RMS position error determined for a point as a function of distance, with the fixed perspective baseline as a parameter.

The primary driver of the position error is the distance, z. For a fixed perspective baseline, d, the error increases rapidly with distance as shown by expression (109) and the discussion following it. To make this more clear, FIG. 50 shows the position error of a measured point as a function of distance for several values of the perspective baseline, when the camera is aligned with the error analysis coordinate system. In FIG. 50, it is assumed that the RMS deviation of the angular measurement is FOV/1000 along the y axis and FOV/1500 along the x axis. It is also assumed that the camera has no distortion and that the aberrations do not vary with field angle, as in Equations (114). Note that there are no distance units given in FIG. 50 because the Figure holds for any distance units one might want to use, provided that all distances are expressed in the same units.

All prior art has taught the use of a fixed perspective baseline. Thus, any system contemplated by the prior art has an error performance given by one of the curves shown in FIG. 50, or some other curve of the same family, depending on the value of the perspective baseline built into the hardware, or into the data processing in the case of the complicated system of Tsujiuchi, et. al. (U.S. Pat. No. 4,895,431) and Hasegawa, et. al. (U.S. Pat. No. 5,432,543).

In the description of operation of the first embodiment, I showed that for any fixed perspective baseline, there is a minimum distance at which a point can be viewed within the camera field of view at both positions P1 and P2. Object points closer than this distance simply cannot be measured, because such points cannot be viewed at both camera positions. This was shown in FIG. 15. The absolute minimum distance for perspective measurements with a fixed perspective baseline is:

$$z_{min} = \frac{d}{2 \tan(HFOV)} \tag{122}$$

where it is implicitly assumed that the borescope or camera has been rotated about the x axis before the measurement to insure that the point is being viewed at y=0. (It is also assumed that the viewing angle is 90 degrees.) In this case, the point of interest appears at the extreme edge of the camera FOV at P1 and at the extreme opposite edge of the FOV at P2.

Figure 51:
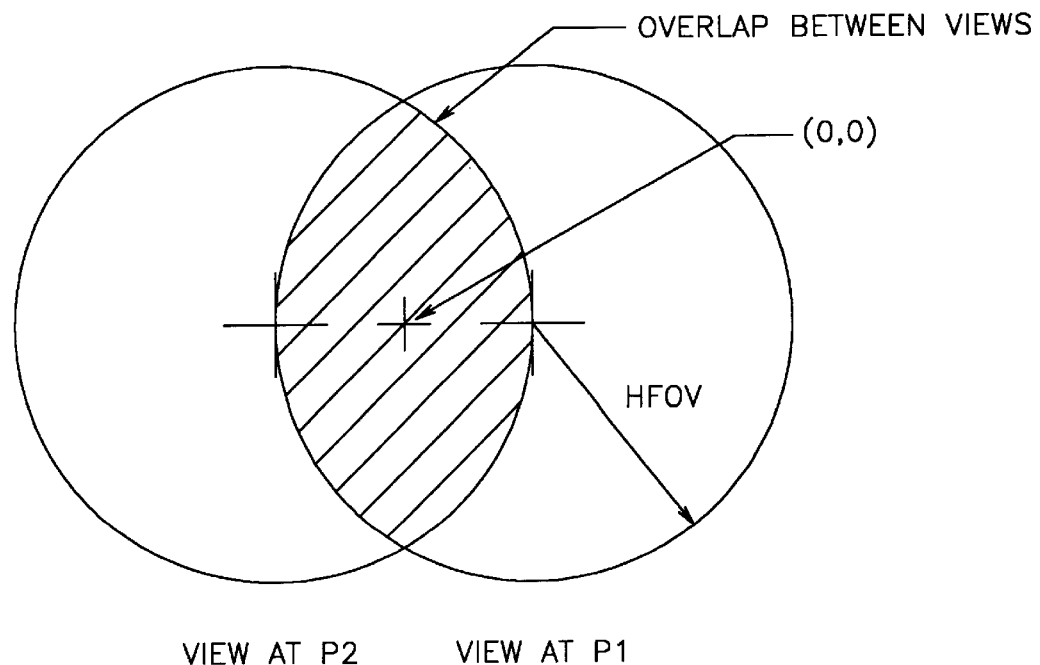
FIG. 51 shows the relationship between the two views for a particular value of the ratio between the distance to the object and the perspective baseline.

FIG. 51 shows the relationship between the two views seen through a camera for a particular value of the ratio d/z. In FIG. 51, the shaded region shows the region of the plane z=constant, that can be seen from both viewing positions. For a fixed perspective baseline d, if z is increased, the apparent overlap region will get larger (see FIG. 15). That is, a larger portion of the camera FOV can be viewed from both position P1 and position P2. Likewise, as z is decreased, the apparent overlap region will get smaller. At $z=z_{min}$ the two apparent fields of view will not overlap at all, but instead will be tangent at a single point.

Of course, it is only those points which lie within the region of overlap between the two views shown in FIG. 51 which can be located with the perspective technique.

For the prior art systems, to measure the positions of two points, and thus the distance between them, requires that both points be visible at both of the viewing positions. Clearly, this can only be the case with a fixed perspective baseline if at least one of the points is further than the minimum distance given by (122). In addition, it is clear that the apparent angle between the two points to be measured must become small as the distance between the points and the camera approaches $z_{min}$.

As was explained above, the error in the distance measurement is determined by the larger of the two position errors, which in this case, is the position error of the point further from the camera. Thus, (122) does not express a feasible situation, in that the error in the distance measurement must be taken to be the error at a distance somewhat larger than that defined in (122), and in that the necessary geometrical relationship between the two points to be measured becomes very restricted as the distance decreases toward $z_{min}$.

To provide a consistent basis for comparison of the performance of the prior art with measurement mode 1 of my system, I define a standard baseline as:

$$d_{std} = z \tan(HFOV) \tag{123}$$

or, to put it another way, a standard distance for a fixed baseline system is taken to be twice the minimum distance defined by (122).

FIG. 51 is drawn for the situation expressed by (123), so that, for instance, the point at (x,y)=(0,0) is viewed at approximately ¼ the FOV in one direction at P1, and at approximately ¼ the FOV in the other direction at P2.

At the standard distance about 39% of the camera's FOV is available for dimensional measurement with a fixed baseline system. That is, for a fixed baseline system, the relationship between the views is as shown in FIG. 51 for a distance of z=2 $z_{min}$. For greater distances, there is more overlap between the views and at smaller distances there is less overlap. As discussed above, as the overlap gets smaller, there is less likelihood that a feasible measurement of distance between two points can be made.

Now, with my technique, the baseline is not fixed, and thus there is no minimum measurement distance. Using the standard baseline as defined in (123), FIG. 51 shows the relationship between the perspective views in my system. However, since the perspective baseline is adjustable in my system and can be made arbitrarily small, the view shown in FIG. 51 applies to my system at any distance. (At large distances, where the hardware of my system can no longer produce a perspective baseline large enough to satisfy (123), the overlap between the two views increases from that shown in FIG. 51.) Thus, a feasible measurement can be made with my system at any distance.

A comparison of the performance of my system to the prior art is shown in FIG. 52. Given my assumptions, which are convenient for comparing the two systems on an even footing, FIG. 52 depicts the two advantages of my system discussed here. The fixed baseline system has a minimum useable distance, shown in FIG. 52 by the solid curve starting at a distance of about 17. My system has no minimum useable distance. At the minimum useable distance, the noise of the prior art is equivalent to the noise of my system. For larger distances, however, the noise of my system increases much more slowly with distance than does the noise of the prior art. Thus, my system is superior to the prior art system at every distance.

Of course, any implementation of my system will have some maximum perspective baseline. For distances larger than $d_{max}/\tan(HFOV)$ the error in my system will also become proportional to $z^2$. However, the error will remain smaller than any fixed baseline system which has a perspective baseline of $d_{max}$ or less, for all greater distances.

Changing the definition of the standard baseline (123) will not change these conclusions. If both systems are used with the same criterion on required overlap for a feasible measurement, at the minimum distance, my system will have the same noise as the prior art system. For larger distances, my system will have less noise, and, of course, my system will have no minimum measurement distance.

It is also the case that the comparison between the performance of my system and the prior art does not depend on the source or size of the alignment errors. That is, the fact that I have used only limited cursor resolution to estimate the size of the errors does not affect the comparison. If both my system and a prior art system are used with the same video and optical parameters, under the same viewing conditions, my system will be superior, in the manner I have explained.

FIG. 52 also shows another advantage of my system of perspective measurement. My measurement mode 2 allows one to optimize the measurement of each of the points of interest on the object individually, as taught in sub-section D. above. This means that measurement mode 2 can have lower error than does measurement mode 1, since mode 1 is necessarily a compromise between what would be optimum for the various points of interest. In FIG. 52 the error when a point is located by moving it between apparent positions at 90% of the camera HFOV is indicated.

Conclusion, Ramifications, and Scope

Accordingly, the reader will see that the dimensional measurement system of this invention has many advantages over the prior art. My system provides more accurate measurements than hitherto available, because I show how to arrange the measurement to minimize the inherent random errors, and because I show how to determine and take into account the actual geometry of and any systematic errors in the hardware. My system provides measurements at lower cost than previously available because I teach how to add the measurement capability to current, widely available, visual inspection hardware. In addition, my system provides a more flexible measurement technique than previously known, in that I teach how to make measurements that are simply impossible with the prior art. Using my invention, it is possible to build special purpose measurement systems to meet any number of specific measurement requirements that are currently not being adequately addressed.

Although the invention has been described with reference to particular embodiments, it will be understood by those skilled in the art that the invention is capable of a variety of alternative embodiments within the spirit and scope of the appended claims.

I claim:

1. A method of perspective measurement of the three-dimensional distances between individual user selected points on a remote object using a camera having an angular field of view and an internal coordinate system, said camera being translated along a substantially straight line from a first viewing position to a second viewing position, with there existing a distance between said first and second viewing positions, wherein the improvement comprises the steps of selecting said first and second camera viewing positions such that said distance between said first and second viewing positions is variable, said first and second viewing positions being selected by the user to be appropriate for each individual measurement being made, thereby obtaining the advantages of lower random error in the perspective measurement and ability to make the measurement in a wider range of situations.

2. The method of claim 1 wherein the measurement result is determined with a least squares estimation procedure.

3. The method of claim 1 wherein the orientation of said camera internal coordinate system with respect to said substantially straight line is determined in a calibration process and wherein said orientation is taken into account in the measurement result.

4. The method of claim 3 wherein errors in the motion of the camera are determined in a calibration process and wherein these errors are taken into account in the measurement result.

5. The method of claim 1 wherein the first and second viewing positions are selected so that a single point on the object is viewed at an apparent angular position near one edge of the field of view at the first viewing position, and at substantially the same apparent angle on the other side of the field of view at the second viewing position.

6. The method of claim 5 wherein said apparent angular position is chosen to correspond to an optimum measurement angle, thereby making measurements with the smallest feasible random errors.

7. An electronic measurement borescope apparatus for measuring three-dimensional distances between selected points on an inaccessible object, comprising:

(a) a video camera, including an imaging lens and a solid state imager, for producing video images of the object, and a video monitor, for displaying said video images;

(b) a linear translation means, for moving the video camera with a substantially constant orientation along a substantially straight line, said linear translation means and camera being disposed at the distal end of a rigid probe, and said linear motion means also having a range of travel;

(c) an actuating means, for moving the linear translation means to any position within its range of travel;

(d) a position measurement means, for determining the position of the linear translation means within said range of travel, whereby the position of the video camera is also determined, said position measurement means also producing position measurement data, said position measurement means also having a first data transfer means for supplying the camera position data to a computing means;

(e) a video cursor means, for displaying variable position cursors on said video image, said video cursor means having a second data transfer means for supplying the spatial positions of said variable position cursors to the computing means; and (f) said computing means having a user interface, said user interface being in communication with said video cursor means and said second data transfer means such that a user can manipulate said video cursor means until said variable position cursors are aligned with the images of said selected points on said inaccessible object, and further such that said spatial positions of said variable position cursors are supplied to the computing means at user command, and further such that said computing means receives the camera position data through said first data transfer means, and further such that said computing means calculates and displays the three-dimensional distances between the selected points on said inaccessible object.

8. The apparatus of claim 7 wherein the actuating means is a motorized micrometer driving a positioning cable, said cable being looped around a pair of idler pulleys and being attached to the linear translation means.

9. The apparatus of claim 7 wherein the actuating means is a motorized micrometer located at the distal end of said rigid probe, said motorized micrometer being attached to the linear translation means.

10. The apparatus of claim 7 wherein said video camera has a field of view, and wherein an illumination means for illuminating said field of view is being carried by the linear translation means, such that the illumination of said field of view remains substantially constant as said camera is moved.

11. An electronic measurement endoscope apparatus for measuring three-dimensional distances between selected points on an inaccessible object, comprising:

(a) a video camera, including an imaging lens and a solid state imager, for producing video images of the object, and a video monitor, for displaying said video images;

(b) a linear translation means, for moving the video camera with a substantially constant orientation along a substantially straight line, said linear translation means also having a range of travel, and said linear translation means and camera being disposed internally into a rigid housing, said rigid housing being disposed at the distal end of a flexible endoscope housing;

(c) an actuating means, for moving the linear translation means to any position within its range of travel;

(d) a position measurement means, for determining the position of the linear translation means within said range of travel, whereby the position of the video camera is also determined, said position measurement means also producing position measurement data, said position measurement means also having a first data transfer means for supplying the position measurement data to a computing means;

(e) a video cursor means, for displaying variable position cursors on said video image, said video cursor means having a second data transfer means for supplying the spatial positions of said variable position cursors to the computing means; and (f) said computing means having a user interface, said user interface being in communication with said video cursor means and said second data transfer means such that a user can manipulate said video cursor means until said variable position cursors are aligned with the images of said selected points on said inaccessible object, and further such that said spatial positions of said variable position cursors are supplied to the computing means at user command, and further such that said computing means receives the camera position data through said first data transfer means, and further such that said computing means calculates and displays the three dimensional distances between the selected points on said inaccessible object.

12. The apparatus of claim 11 wherein the actuating means is a positioning wire encased in a sheath, which is driven by a motorized micrometer.

13. The apparatus of claim 11 wherein the actuating means is a motorized micrometer located at the distal end of the apparatus, said motorized micrometer being attached to the linear translation means.

14. The apparatus of claim 11 wherein said video camera has a field of view, and wherein an illumination means for illuminating said field of view is being carried by the linear translation means, such that the illumination of said field of view remains substantially constant as said camera is moved.

15. A method of determining a set of three-dimensional coordinates for at least one point on an inaccessible object, thereby determining a location vector for each of said at least one point, comprising the steps of:

(a) providing one or more cameras, each of which has an internal coordinate system and an effective focal length, and providing motion means for moving at least one of said one or more cameras with respect to the inaccessible object, and further providing a plurality of relative camera positions for each of said cameras, wherein each of said cameras has a spatial orientation at each of said relative positions, and wherein said relative positions and said spatial orientations are determined in an external coordinate system;

(b) choosing first and second camera viewing positions, each of which corresponds to one of said relative camera positions, wherein there exists a distance between said first and second camera viewing positions, and wherein there exists a midpoint between said first and second camera viewing positions, and wherein there exists an angle subtended by the distance between said first and second camera viewing positions at any particular one of said at least one point on the inaccessible object, and wherein the distance between said first and second camera viewing positions is chosen to adjust said angle subtended at said particular one point to be substantially the same, independent of the distance between said particular one point on the inaccessible object and said midpoint between said viewing positions, whereby the random errors in the location vectors determined for said at least one point are minimized;

(c) acquiring a set of first images of said at least one point with one of said one or more cameras located at said first viewing position, said camera having a first spatial orientation at said first viewing position, thereby defining a first measurement coordinate system which is coincident with the internal coordinate system of said camera at said first viewing position;

(d) measuring the coordinates of each of said first images of said at least one point in said first measurement coordinate system;

(e) acquiring a set of second images of said at least one point with one of said one or more cameras located at said second viewing position, said camera having a second spatial orientation at said second viewing position, thereby defining a second measurement coordinate system which is coincident with the internal coordinate system of said camera at said second viewing position;

(f) measuring the coordinates of each of said second images of said at least one point in said second measurement coordinate system;

(g) correcting the measured coordinates of each of said first images of said at least one point to adjust for any distortion of the camera located at the first viewing position, and correcting the measured coordinates of each of said second images of said at least one point to adjust for any distortion of the camera located at the second viewing position, thereby producing sets of first and second final point image coordinates for said first and second viewing positions in said first and second measurement coordinate systems; and (h) computing three dimensional coordinates for each of said at least one point using said first and second final point image coordinates, the effective focal length of the camera located at the first viewing position, and the effective focal length of the camera located at the second viewing position, and also using the relationships between said first and second viewing positions and said first and second spatial orientations determined in said external coordinate system, thereby computing a location vector for each of said at least one point.

16. The method of claim 15 in which step (h) comprises the steps of:

(h) multiplying the first final point image coordinates by the mathematical inverse of the effective focal length of the camera located at the first viewing position and multiplying the second final point image coordinates by the mathematical inverse of the effective focal length of the camera located at the second viewing position, to determine the mathematical tangents of the angles at which each of said at least one point is viewed in said first and second measurement coordinate systems; and (i) forming least squares estimates of the three dimensional coordinates for each of said at least one point in a third measurement coordinate system using said mathematical tangents of the viewing angles for each of said at least one point in said first and second measurement coordinate systems and the relationships between said first and second camera viewing positions and said first and second camera spatial orientations determined in said external coordinate system, thereby forming a least squares estimate of the location vector for each of said at least one point in said third measurement coordinate system.

17. The method of claim 16 wherein the third measurement coordinate system is the same as the first measurement coordinate system.

18. The method of claim 15 wherein said angle subtended by the distance between said first and second camera viewing positions is calculated during the selection of at least one of said viewing positions using the changes in the coordinates of the image of said particular one point between one or more preliminary first views and one or more preliminary second views, the effective focal length of the camera used for the first views, the effective focal length of the camera used for the second views, and the relationships between the camera viewing positions and orientations.

19. The method of claim 16 for determining the three-dimensional distances between the points of each pair of any set of pairs of points in a plurality of points on an inaccessible object, comprising the steps of:

(i) performing steps (h) through (i) of claim 16 for said plurality of points;

(k) determining a difference vector between the location vectors of a first pair of said set of pairs of points by subtracting the location vector of a first point of said pair from the location vector of the second point of said pair;

(l) determining the length of the difference vector by calculating the square root of the sum of the squares of the components of the difference vector; and (m) repeating steps (k) and (l) as necessary to determine the distances between the points of all remaining pairs in said set of pairs of points.

20. A method of determining the three-dimensional distance between a pair of points on an object, comprising the steps of:

(a) providing one or more cameras, each of which has an internal coordinate system and an effective focal length, and further providing a plurality of relative camera positions for each of said cameras, wherein each of said cameras has a spatial orientation at each of said relative positions, wherein said relative positions and said spatial orientations are determined in an external coordinate system, such that said camera positions form camera location vectors in said external coordinate system;

(b) acquiring a first image of a first point of said pair of points on the object with one of said one or more cameras located at a first viewing position, said camera having a first spatial orientation at said first viewing position, thereby defining a first measurement coordinate system which is coincident with the internal coordinate system of said camera at said first viewing position;

(c) acquiring a second image of said first point of said pair of points on the object with one of said one or more cameras located at a second viewing position, said camera having a second spatial orientation at said second viewing position, thereby defining a second measurement coordinate system which is coincident with the internal coordinate system of said camera at said second viewing position;

(d) measuring the coordinates of said first image of said first point in said first measurement coordinate system and measuring the coordinates of said second image of said first point in said second measurement coordinate system;

(e) correcting the measured coordinates of the first image of said first point to adjust for any distortion of the camera located at the first viewing position, and correcting the measured coordinates of the second image of said first point to adjust for any distortion of the camera located at the second viewing position, thereby producing first and second final first point image coordinates for said first and second viewing positions in said first and second measurement coordinate systems;

(f) multiplying the first final first point image coordinates by the mathematical inverse of the effective focal length of the camera located at the first viewing position and multiplying the second final first point image coordinates by the mathematical inverse of the effective focal length of the camera located at the second viewing position, to determine the mathematical tangents of the angles at which said first point is viewed in said first and second measurement coordinate systems;

(g) forming a least squares estimate of the three dimensional coordinates of said first point in a first temporary measurement coordinate system, thereby forming an estimate of the vector location of said first point in said first temporary measurement coordinate system, using said mathematical tangents of the viewing angles of said first point in said first and second measurement coordinate systems and the relationships between said first and second camera viewing positions and said first and second camera spatial orientations determined in said external coordinate system, wherein said first temporary coordinate system has an origin and wherein said origin has a vector location in said external coordinate system;

(h) calculating a vector location of said first point in said external coordinate system by adjusting the vector location of said first point in said first temporary measurement coordinate system according to said first and second camera spatial orientations;

(i) acquiring a first image of a second point of said pair of points on the object with one of said one or more cameras located at a third viewing position, said camera having a third spatial orientation at said third viewing position, thereby defining a third measurement coordinate system which is coincident with the internal coordinate system of said camera at said third viewing position;

(j) acquiring a second image of said second point of said pair of points on the object with one of said one or more cameras located at a fourth viewing position, said camera having a fourth spatial orientation at said fourth viewing position, thereby defining a fourth measurement coordinate system which is coincident with the internal coordinate system of said camera at said fourth viewing position, and wherein at least one of said third and fourth viewing positions is different from either of said first and second viewing positions;

(k) measuring the coordinates of said first image of said second point in said third measurement coordinate system and measuring the coordinates of said second image of said second point in said fourth measurement coordinate system;

(l) correcting the measured coordinates of the first image of said second point to adjust for any distortion of the camera located at the third viewing position, and correcting the measured coordinates of the second image of said second point to adjust for any distortion of the camera located at the fourth viewing position, thereby producing first and second final second point image coordinates for said third and fourth viewing positions in said third and fourth measurement coordinate systems;

(m) multiplying the first final second point image coordinates by the mathematical inverse of the effective focal length of the camera located at the third viewing position and multiplying the second final second point image coordinates by the mathematical inverse of the effective focal length of the camera located at the fourth viewing position, to determine the mathematical tangents of the angles at which said second point is viewed in said third and fourth measurement coordinate systems;

(n) forming a least squares estimate of the three dimensional coordinates of said second point in a second temporary measurement coordinate system, thereby forming an estimate of the vector location of said second point in said second temporary measurement coordinate system, using said mathematical tangents of the viewing angles of said second point in said third and fourth measurement coordinate systems and the relationships between said third and fourth camera viewing positions and said third and fourth camera spatial orientations determined in said external coordinate system, wherein said second temporary coordinate system has an origin and wherein said origin has a vector location in said external coordinate system;

(o) calculating a vector location of said second point in said external coordinate system by adjusting the vector location of said second point in said second temporary measurement coordinate system according to said third and fourth camera spatial orientations;

(p) calculating the vector location of the origin of the first temporary coordinate system by forming the average of the camera location vectors for the first and second camera viewing positions;

(q) calculating the vector location of the origin of the second temporary coordinate system by forming the average of the camera location vectors for the third and fourth camera viewing positions;

(r) calculating a vector from the origin of the second temporary coordinate system to the origin of the first temporary coordinate system by subtracting the vector location of the origin of the second temporary coordinate system from the vector location of the origin of the first temporary coordinate system;

(s) calculating the vector from the second point of said pair of points to the first point of said pair of points with the equation $$r = d_{AB} + r_{AG} - r_{BG}$$

wherein $d_{AB}$ is the vector from the origin of the second temporary coordinate system to the origin of the first temporary coordinate system, $r_{AG}$ is said vector location of said first point in said external coordinate system, and $r_{BG}$ is said vector location of said second point in said external coordinate system; and (t) calculating the distance between said pair of points by calculating the length of the vector r.

21. An apparatus for measuring three-dimensional distances between individual user selected points on an inaccessible object, comprising:

(a) a rigid borescope, having a length, being substantially side-looking and having an imaging means for producing images of said points on said object;

(b) linear motion means, for moving the borescope with a substantially constant orientation along a substantially straight line, said linear motion means also having a range of travel;

(c) position measurement means, for determining the position of the linear motion means within said range of travel, said position measurement means also producing position measurement data;

(d) clamping means, for clamping the borescope to the linear motion means at a desired position along said length of said borescope, whereby the position of the borescope is determined by the position of the linear motion means, and whereby said position measurement data also represents the position of the borescope;

(e) image measurement means, for measuring the positions of said images of said points, said image measurement means also producing position data of said images of said points; and (f) computing means for receiving said borescope position data said position data of said images of said points, said computing means being adapted to calculate the three-dimensional distances between said points on said inaccessible object.

22. The apparatus of claim 21 wherein the position measurement means is a micrometer, and the linear motion means is a linear translation stage being driven by said micrometer.

23. The apparatus of claim 21 wherein the linear motion means is a linear translation stage being driven by an actuator, and the position measurement means is a linear position transducer attached to said translation stage.

24. The apparatus of claim 21 wherein said linear motion means is selected from the group consisting of crossed roller slides and ball slides and air bearing slides and dovetail slides.

25. The apparatus of claim 21 wherein said borescope has a field of view, and wherein said imaging means is comprised in part of a video sensor optically coupled to said borescope, and wherein said video sensor has different spatial resolutions along its two sensing axes, further wherein said video sensor is rotationally oriented with respect to said borescope such that a high spatial resolution axis thereof is aligned parallel to the projection of the linear motion of the borescope as observed in the field of view, thereby obtaining the highest precision in the distance measurement.

26. An apparatus for measuring three-dimensional distances between individual user selected points on an inaccessible object, comprising at least one probe body and additionally comprising:

(a) one or more cameras located near the distal ends of said at least one probe body, said cameras forming images of said selected points on said object;

(b) motion means for moving at least one of said one or more cameras with respect to its probe body, said motion means providing a plurality of relative camera positions for each of said cameras;

(c) orientation means for providing a relative spatial orientation for each of said cameras at each of said relative positions;

(d) position determination means, for determining the relative positions of each of said one or more cameras, said position determination means also producing camera position data;

(e) orientation determination means, for determining the relative orientations of each of said one or more cameras, said orientation determination means also producing camera orientation data;

(f) image measurement means, for measuring the positions of said images of said user selected points on said object, said image measurement means also producing position data of said images of said user selected points; and (g) computing means for receiving said camera position data and said camera orientation data and said position data of said images of said user selected points, said computing means being adapted to calculate the three-dimensional distances between said user selected points on said inaccessible object.

27. The apparatus of claim 26 wherein the orientation means is combined with the motion means such that said relative orientations are predetermined functions of said relative positions, thereby making it possible to eliminate the use of said orientation determination means except during calibration.

28. The apparatus of claim 26 wherein said plurality of relative camera positions constitutes a set of fixed relative positions, thereby making it possible to eliminate the use of said position determination means except during calibration.

29. The apparatus of claim 26 wherein said relative camera positions all lie along a substantially straight line.

30. The apparatus of claim 26 wherein said relative camera spatial orientations are all substantially the same.

31. The apparatus of claim 26 wherein said relative camera positions all lie along a substantially circular arc.

32. The apparatus of claim 31 wherein said circular arc has a center of curvature, and wherein each of said cameras has an optical axis, and wherein the orientation of each of said one or more cameras is coupled to its position along the arc so that said optical axis is always substantially aligned with said center of curvature of the arc.

33. The apparatus of claim 31 wherein said arc is contained in a plane, and wherein each of said cameras has an optical axis, wherein the orientation of each of said one or more cameras is such that said optical axis is aligned substantially perpendicular to the plane containing the arc.

34. The apparatus of claim 21 wherein said imaging means is comprised in part of a video sensor and a video monitor, and wherein said image measurement means is comprised in part of an analog video cursor controller connected between said video sensor and said video monitor.

35. The apparatus of claim 23 wherein the actuator is an air cylinder.

\* \* \* \* \*

UNITED STATES PATENT AND TRADEMARK OFFICE
CERTIFICATE OF CORRECTION

PATENT NO. : 6,009,189            Page 1 of 4
DATED       : December 28, 1999
INVENTOR(S) : David F. Schaack It is certified that error appears in the above-identified patent and that said Letters Patent is hereby corrected as shown below:

In column 18, line 42, insert --, $y'_{im1}$-- after "$x'_{im1}$".

In column 19, line 52, replace "$f_{Dz}$" with --$f_{Dx}$--.

In column 19, line 53, replace "$f_{Dz}$" with --$f_{Dx}$--.

In column 20, Equation (4), replace "$\alpha_{z1}$" with --$\alpha_{x1}$-- and replace "$\alpha_{z2}$" with --$\alpha_{x2}$--.

In column 20, Equation (6), replace the subscript "2" with --z-- and replace "$R_b$" with --$d_b$--.

In column 21, Equation (12), delete "$- A$".

In column 24, line 9, replace "mode I" with --mode 1--.

In column 35, line 15, replace "arc" with --are--.

In column 46, Equation (28), delete the second opening parenthesis.

UNITED STATES PATENT AND TRADEMARK OFFICE
CERTIFICATE OF CORRECTION

PATENT NO. : 6,009,189
DATED : December 28, 1999
INVENTOR(S) : David F. Schaack

It is certified that error appears in the above-identified patent and that said Letters Patent is hereby corrected as shown below:

In column 50, Equation (41), replace "$f_{Dz}$" with --$f_{Dx}$--.

In column 51, Equation (49), there are two separate equations. Separate the equations before "$r_{0k2}$".

In column 52, Equation (52), there are two separate equations. Separate the equations before "$A_{v2}$".

In column 52, Equation (53), insert space between the terms "$A_{v1}$" and "$A_{v2}$", between the terms "$r_{cal}$" and "$r_{cal}$" and between the terms "$r_c(\eta_1)1_k$" and "$r_c(\eta_2)1_k$".

In column 53, Equation (57), there are two separate equations. Separate the equations before "$r_{0k2}$".

In column 53, Equation (57), replace "$R(\eta)$" with --$R(\eta_2)$--.

In column 53, Equation (58), there are two separate equations. Separate the equations before "$A_{v2}$".

In column 53, Equation (59), insert space between the terms "$A_{v1}$" and "$A_{v2}$", between the terms "$R(\eta_1)r_{cal}$" and "$R(\eta_2)r_{cal}$" and between the terms "$R(\eta_1)r_c(\eta_1)1_k$" and "$R(\eta_2)r_c(\eta_2)1_k$".

In column 56, Equation (61) there are three separate equations. Separate the equations before "$y =$" and before "$z =$".

In column 56, Equation (62) there are three separate equations. Separate the equations before "$y_{im} =$" and before "$z_{im} =$".

In column 56, Equation (62) delete " $-$ " following the first occurrence of "$i$" and delete " $- 1$" following the second occurrence of "$i$".

In column 58, line 39, change "originated" to --origin at d--.

UNITED STATES PATENT AND TRADEMARK OFFICE
CERTIFICATE OF CORRECTION

PATENT NO. : 6,009,189   Page 3 of 4
DATED : December 28, 1999
INVENTOR(S) : David F. Schaack It is certified that error appears in the above-identified patent and that said Letters Patent is hereby corrected as shown below:

In column 60, Equation (78), delete "i".

In column 62, Equation (86), replace "$R_{v1}$" with --$R\ v_1$--.

In column 62, Equation (89) there are three separate equations. Separate the equations before "$v_1 =$".

In column 63, Equation (91) there are two separate equations. Separate the equations before "$r_{v1}$".

In column 63, Equation (92), delete space between the first occurrence of "$R_{12}^{-1}$" and "$a_{v2}$".

In column 63, Equation (92), add space between " − " and "$a_{v1}$" and delete space between the second occurrence of "$R_{12}^{-1}$" and "$a_{v2}$".

In column 63, Equation (94), delete space between the first occurrence of "$R_{12}^{-1}$" and "$a_{v2}$".

In column 63, Equation (94), add space between " − " and "$a_{v1}$" and delete space between the second occurrence of "$R_{12}^{-1}$" and "$a_{v2}$".

In column 65, line 13, insert an opening parenthesis before " − w/2".

In column 66, line 66, insert -- $d\zeta_{y1}$,-- before "and".

In column 67, Equation (103), insert --)-- before the first occurrence of " = ".

In column 67, Equation (103), insert a superscript --T-- after the first occurrence of "$\Delta r$".

In column 67, Equation (103), insert --S-- after "$S^T$".

In column 67, line 34, replace "$(\Delta t\, \Delta t^T)$" with --$\langle \Delta t\, \Delta t^T \rangle$--.

UNITED STATES PATENT AND TRADEMARK OFFICE
CERTIFICATE OF CORRECTION

PATENT NO. : 6,009,189
DATED : December 28, 1999
INVENTOR(S) : David F. Schaack

It is certified that error appears in the above-identified patent and that said Letters Patent is hereby corrected as shown below:

In column 67, Equation (105), insert -- $= G_{11} \langle (d\xi_{x1})^2 \rangle$ -- after "$\langle |\Delta r|^2 \rangle$".

In column 67, Equation (103), insert --)-- before " = ".

In column 71, Equation (117), replace subscript "$z$" with --$x$--.

In column 72, line 19, replace subscript "$z$" with --$x$--.

In column 82, line 21, replace the first occurrence of "(i)" with --(j)--.

In column 85, line 21, insert --and-- after the first occurrence of "data".

In column 86, lines 37, 38, 42, 43, 44, and 48, change "are" to --arc--.

Signed and Sealed this

Ninth Day of January, 2001

Attest:

Attesting Officer

Q. TODD DICKINSON
Commissioner of Patents and Trademarks